(12) United States Patent
Woolf et al.

(10) Patent No.: US 12,359,197 B2
(45) Date of Patent: Jul. 15, 2025

(54) COMPOSITIONS AND METHODS FOR EDITING NUCLEIC ACIDS IN CELLS UTILIZING OLIGONUCLEOTIDES

(71) Applicant: Etagen Pharma, Inc., Sudbury, MA (US)

(72) Inventors: Tod M. Woolf, Sudbury, MA (US); Alexandre V. Lebedev, Sudbury, MA (US); Richard I. Hogrefe, San Diego, CA (US)

(73) Assignee: Etagen Pharma, Inc., Sudbury, MA (US)

( * ) Notice: Subject to any disclaimer, the term of this patent is extended or adjusted under 35 U.S.C. 154(b) by 224 days.

(21) Appl. No.: 15/533,965

(22) PCT Filed: Dec. 11, 2015

(86) PCT No.: PCT/US2015/065348
§ 371 (c)(1),
(2) Date: Sep. 27, 2017

(87) PCT Pub. No.: WO2016/094845
PCT Pub. Date: Jun. 16, 2016

(65) Prior Publication Data
US 2021/0395729 A1    Dec. 23, 2021

Related U.S. Application Data

(60) Provisional application No. 62/252,693, filed on Nov. 9, 2015, provisional application No. 62/180,175, filed on Jun. 16, 2015, provisional application No. 62/091,027, filed on Dec. 12, 2014, provisional application No. 62/141,077, filed on Mar. 31, 2015.

(51) Int. Cl.
*C12N 15/11* (2006.01)
*C12N 15/10* (2006.01)

(52) U.S. Cl.
CPC .......... *C12N 15/111* (2013.01); *C12N 15/102* (2013.01); *C12N 2310/11* (2013.01); *C12N 2310/315* (2013.01); *C12N 2310/333* (2013.01); *C12N 2310/335* (2013.01); *C12N 2310/344* (2013.01); *C12N 2310/351* (2013.01); *C12N 2320/34* (2013.01)

(58) Field of Classification Search
CPC .......... C12N 15/102; C12N 15/113; C12N 2310/11; C12N 2310/31; C12N 2310/32; C12N 2310/33
See application file for complete search history.

(56) References Cited

U.S. PATENT DOCUMENTS

| | | | |
|---|---|---|---|
| 2002/0119570 A1* | 8/2002 | Yoon | C12N 15/102 435/455 |
| 2004/0014057 A1* | 1/2004 | Kmiec | A61P 7/04 435/6.16 |
| 2004/0175722 A1* | 9/2004 | Kmiec | C12N 15/102 435/6.13 |
| 2005/0095710 A1 | 5/2005 | Cowsert et al. | |
| 2006/0031946 A1 | 2/2006 | Bizemont et al. | |
| 2008/0227104 A1 | 9/2008 | Hayashizaki et al. | |
| 2008/0287379 A1* | 11/2008 | Tabatadze | C12N 15/113 536/23.1 |
| 2009/0307805 A1 | 12/2009 | De Both et al. | |
| 2011/0077285 A1* | 3/2011 | Hedtjarn | A61P 9/00 435/375 |
| 2011/0301218 A1 | 12/2011 | Bozzoni et al. | |
| 2012/0165228 A1 | 6/2012 | Liu et al. | |
| 2013/0281684 A1* | 10/2013 | Freier | A61P 25/28 536/24.5 |
| 2014/0273226 A1 | 9/2014 | Wu | |

(Continued)

FOREIGN PATENT DOCUMENTS

JP    2015/523856 A    8/2015
WO    WO-2013/176772 A1    11/2013
(Continued)

OTHER PUBLICATIONS

Knowles et al. Cold Spring Harb Perspect Med 2:a009548, 1-13 (Year: 2012).*

(Continued)

*Primary Examiner* — Brian Whiteman
(74) *Attorney, Agent, or Firm* — Foley Hoag LLP; Susan M. Abelleira; Mohanad Mossalam

(57) ABSTRACT

The present invention includes compositions and methods for the treatment of a medical condition or disease utilizing editing oligonucleotides. The editing oligonucleotides contain an oligonucleotide strand of about 10 to about 50 nucleotides on each side of the editing moiety which may contain a sugar or linker that positions the active editing moiety in the proper location for hybridization to the target nucleic acid. The editing oligonucleotides may also contain at least one nucleotide sequence change from the targeted sequence in the genome. The method includes modifying a genomic sequence within a cell utilizing an editing oligonucleotide without additional proteins or nucleic acids to assist in the editing process. The editing oligonucleotide may comprise backbone modifications that increase the nuclease stability of the oligonucleotide as compared to unmodified oligonucleotides or oligonucleotides having three phosphorothioates on each terminus.

18 Claims, 35 Drawing Sheets
Specification includes a Sequence Listing.

(56) References Cited

U.S. PATENT DOCUMENTS

| | | | | |
|---|---|---|---|---|
| 2015/0166980 A1* | 6/2015 | Liu | ......................... | A61P 21/00 435/227 |
| 2016/0108369 A1 | 4/2016 | Kuno et al. | | |
| 2017/0233762 A1 | 8/2017 | Zalatan et al. | | |
| 2019/0218552 A1* | 7/2019 | Turunen | .................. | A61P 25/28 |
| 2019/0300872 A1* | 10/2019 | Woolf | .................. | C12N 15/102 |
| 2022/0267806 A1 | 8/2022 | Jin et al. | | |

FOREIGN PATENT DOCUMENTS

| | | | | |
|---|---|---|---|---|
| WO | WO-2013173599 A1 * | 11/2013 | ......... | A61K 31/7088 |
| WO | WO-2014011053 A1 * | 1/2014 | ......... | A61K 31/7088 |
| WO | WO-2014/144951 A1 | 9/2014 | | |
| WO | WO-2014/172458 A1 | 10/2014 | | |
| WO | WO-2015/089406 A1 | 6/2015 | | |
| WO | WO-2015/133554 A1 | 9/2015 | | |
| WO | WO-2015/139008 A1 | 9/2015 | | |
| WO | WO-2015/161276 A2 | 10/2015 | | |
| WO | WO-2016/033246 A1 | 3/2016 | | |
| WO | WO-2016094845 A2 * | 6/2016 | ............. | A61K 48/00 |

OTHER PUBLICATIONS

Radecke et al. The Journal of Gene Medicine 8: 217-228 (Year: 2006).*
Friedman et al. JBC 274, pp. 36193-36199 (Year: 1999).*
Written Opinion of the International Searching Authority, PCT/NL2013/050534 Proqr Therapeutics B.V., pp. 1-8 (Year: 2015).*
Sargent et al. Oligonucleotides vol. 21, pp. 55-75 (Year: 2011).*
Engstrom et al., "Regulation of targeted gene repair by intrinsic cellular processes" Bioessays, 31: 159-168 (2009).
Extended European Search Report for EP Application No. 21210808.8 dated Jun. 7, 2022.
International Search Report and Written Opinion for International Application No. PCT/US15/65348 dated Apr. 12, 2017.
International Search Report and Written Opinion for International Application No. PCT/US2017/031381 dated Sep. 29, 2017.
Radecke et al., "Physical incorporation of a single-stranded oligodeoxynucleotide during targeted repair of a human chromosomal locus", The Journal of Gene Medicine: A cross-disciplinary journal for research on the science of gene transfer and its clinical applications 8(2): 217-228 (2006).
Hendel et al., "Chemically modified guide RNAs enhance CRISPR-Cas genome editing in human primary cells", Nature biotechnology 33.9: 985-989 (2015).
Ali et al., "Sequence- and base-specific delivery of nitric oxide to cytidine and 5-methylcytidine leading to efficient deamination." Journal of the American Chemical Society 126.29 (2004): 8864-8865.
Bialk et al., "Regulation of Gene Editing Activity Directed by Single-Stranded Oligonucleotides and CRISPR/Cas9 Systems," PLoS One 10.6 (2015): 1-19.
Eckstein et al., "Phosphorothioates, Essential Components of Therapeutic Oligonucleotides," Nucleic Acid Therapeutics, 24.6 (2014): 374-387.
Extended European Search Report for EP Application No. EP24153079.9 dated Jun. 28, 2024.
Falgowski et al., "Strand bias influences the mechanism of gene editing directed by single-stranded DNA oligonucleotides," Nucleic Acids Rsearch 39.11 (2011): 4783-4794.
Karvelis et al., "crRNA and tracrRNA guide Cas9-mediated DNA interference in *Streptococcus thermophilus*", RNA Biology 10.5 (2013): 841-851.
Livingston et al., "Oligonucleotide delivery by nucleofection does not rescue the reduced proliferation phenotype of gene-edited cells," Nucleic Acid Therapeutics 22.6 (2012): 405-413.
O'Reilly et al., "Extensive CRISPR RNA modification reveals chemical compatibility and structure-activity relationships for Cas9 biochemical activity," Nucleic Acids Research (2018): 1-13.
Rivera-Torres et al., "The Position of DNA Cleavage by TALENs and Cell Synchronization Influences the Frequency of Gene Editing Directed by Single-Stranded Oligonucleotides," PLoS One 9.5 (2014): e96483.
Zhao et al., "Oligonucleotide-based targeted gene editing in C. elegans via the CRISPR/Cas9 system," Cell Research—Xibao Yanjiu 24.2 (2014): 247-250.

* cited by examiner

FIGURE 10
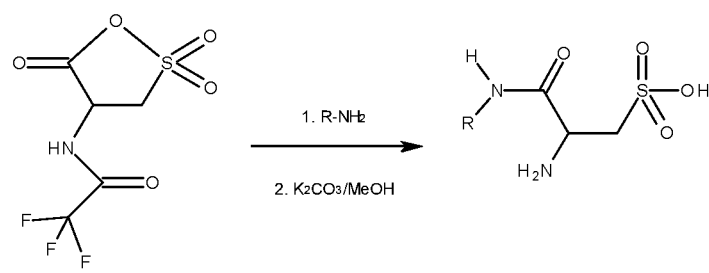
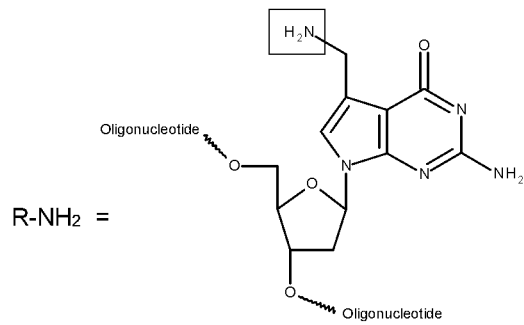
R-NH2 =
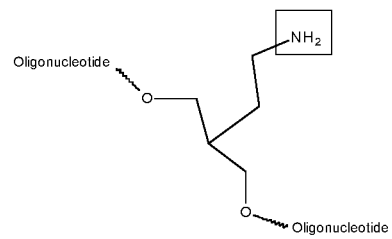

FIGURE 13
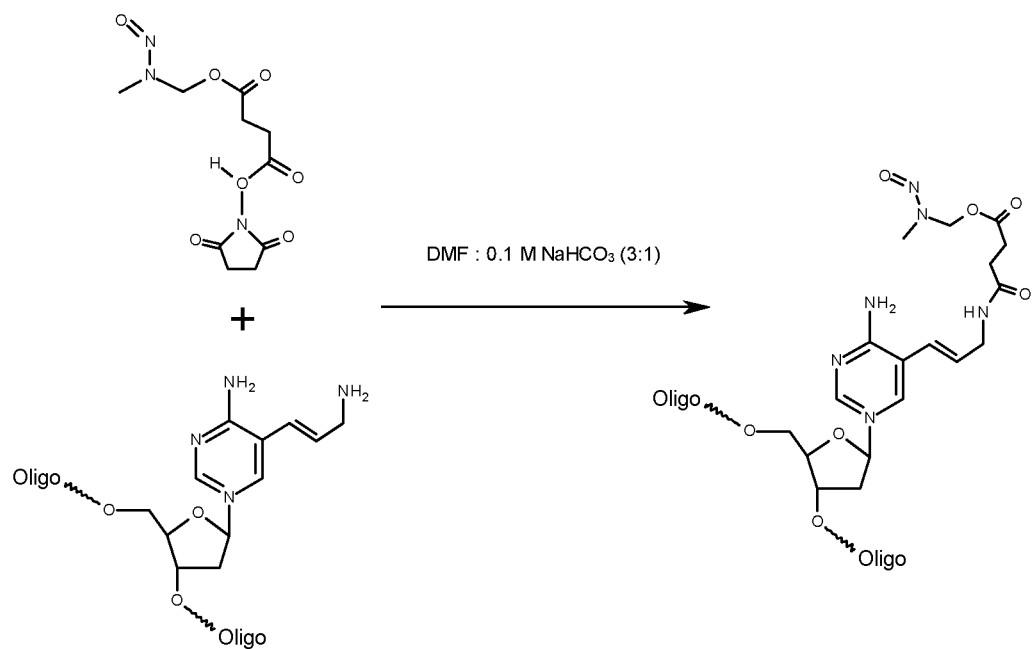
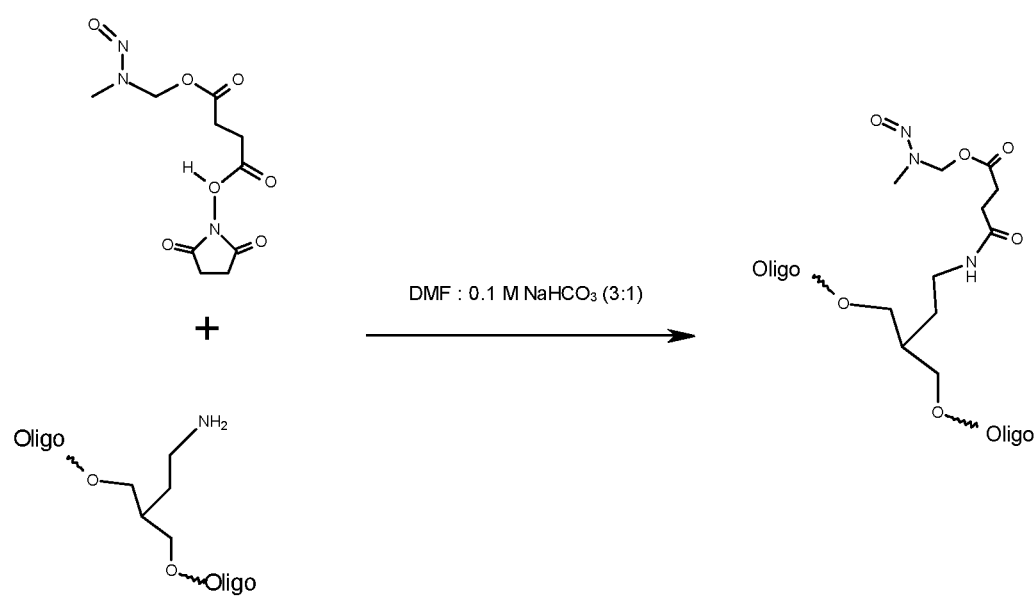

FIGURE 20

BACKBONE MODIFICATIONS

Methylene formacetyl backbone

Methylenehydrazino backbones

Methyleneimino backbone

Methylphosphonate nucleotides (include chirally enriched methyphonsponates).

Moranophosphate

Morpholino

Non-bridging dialkylphosphoramidate

P-Boronated

Xanthine

Phosphoramidate

Phosphorothioate nucleotides (including chirally enriched phosphorothioate nucleotides)

Phosphotriester (alkyl, aryl, heteroalkyl, heteroaryl)

PNA including gamma PNAs

Reversible charge-neutralizing phosphophotriester backbone modifications

Siloxane backbones

Sulfamate backbones

Sulfide, sulfoxide

Sulfonamide backbones

Sulfonate backbone

Sulfone backbones

UNA (unlocked nucleic acid)

Thioformacetyl backbones

FIGURE 21

NUCLEOBASE MODIFICATIONS 2-thiothymine 2-thiouracil 3-deazaadenine 3-deazaguanine 4-thiouracil C-5 Propyne 5-halo particularly 5-bromo, 5-trifluoromethyl and other 5-substituted uracils and cytosines 5-halouracil and cytosine 5-hydroxymethyl cytosine 5-methylcytosine (5-me-C)

5-propynyl uracil and cytosine 5-uracil (also know as pseudouracil)

6-azo uracil, cytosine and thymine 6-methyl and other alkyl derivatives of adenine and guanine 7-deazaadenine 7-deazaguanine 7-methyladenine 7-methylguanine 8-azaadenine 8-azaguanine 8-halo, 8-amino, 8-thiol, 8-thioalkyl, 8-hydroxyl and other 8-substituted adenines and guanines Biotinylated bases 9-(aminoethoxy)phenoxazine (G-clamp)

Fluorescent labeled bases

Hypoxanthine

Pseudo complementary bases

Universal bases (bind all for complementary bases (A, T(or U), C and G)

FIGURE 22

SUGAR MODIFICATIONS

2' amino

2' fluoro

2' methoxyethoxy

2'-O-substuted Alklyl

2'-O-X (where X is a modification known in the art to result in a hybridization capable oligonucleotide 2'ribose bridged to the 4'ribose position (i.e., often referred to as constrained or locked nucleotides) including but not limited to LNAs and cET-BNAs, a bridging 3'-CH2- or 5'-CH2-, a bridging 3'-amide (-C(O)-NH-) or 5'-amide (-C(O)-NH-) or any combination thereof.

2'-O-allyl

2'-O-aminoalkyl

2'-O-aminoalkyl, 2'-O-allyl

2'-O-ethyl

2'-O-methyl

2'-O-propyl

Alpha anomers

Beta anomers

FIGURE 23

| Disorder | Mutated Genes | Preferred Edit Class |
| --- | --- | --- |
| Alzheimer's Disease | APP | Repair and/or Edit to Protective |
| Alzheimer's Disease | APOE4 | Edit to Neutral or Protective |
| Beta-thalassemia | Beta Globin (HBB) | Repair |
| Cystic fibrosis | CFTR | Repair |
| Duchenne muscular dystrophy | Dystrophin | Repair directly or by exon skipping |
| Hemophilia A (Haemophilia) | Factor XIII (F8) | Repair |
| Hemophilia B (Haemophilia) | Factor IX (F9) | Repair |
| Sickle Cell Anemia (drepanocytosis) | HgbS | Repair |
| TTR Amyloidosis (FAP) | Dominant Mutation in transthyretin gene (TTR) (e.g. R333Q) | Repair, modulate or Knockout |
| Alpha-1 Antitrypsin Deficiency | Alpha-1 Antitrypsin | Repair |
| Alzheimer's Disease | Tau, PSEN1, PSEN2, Beta-Secretase, TTR | Repair or modulate activity |
| Becker Muscular Dystrophy | Dystrophin | Repair |
| Breast and ovarian cancer predisposition mutations | BRCA1 and BRCA2 | Repair |
| Cardiovascular disease | Apoa, CRP | Knockout |
| Diabetes | GCGR (glucagon receptor) | Knockout or modulate |
| Fabry disease | alpha-galactosidase A | Repair |
| Familial dysautonomia | IKBKAP | Repair |
| Familial Hypercholesterolemia | APOB, LDLR, LDLRAP1, and PCSK9 | Repair or edit to protective |
| Hemophilia and Rare Bleeding Disorders | AT (Antithrombin) | Knockout |
| Hereditary Blindness | Rhodopsin, RP1 RP2, rd1, CEP290 and others | Repair |
| Hereditary tyrosinemia | Fumarylacetoacetate hydrolase (FAH) | Repair |
| HIV Infection | CCR5 | Knockout or edit in protective variant |
| Hypercholesterolemia | PCSK9,ApoB-100 | Knockout |
| Hypertriglyceridemia | Apolipoprotein C-III | Knockout |
| Mucopolysaccharidosis (MPS I) (Hurler syndrome) | IDUA | Repair |

FIGURE 23 cont.

| Disorder | Mutated Genes | Preferred Edit Class |
| --- | --- | --- |
| Obesity | RIP140, FGFR4 | Knockout |
| Retinoblastoma | rb | Repair |
| Senile Systemic Amyloidosis | TTR | Knockout, or modulate activity |
| Spinal muscular atrophy (SMA) | SMN1, UBA1, DYNC1H1, SMN2 and VAPB | Repair |
| Type 1 Diabetes (caused by insulin receptor mutations) | Insulin Receptor | Repair |
| Type 2 diabetes | GCC, PTP-1B | Knockout or modulate |
| Wilson's disease | ATP7B, H1069Q, R778L | Repair |
| Achromatopsia | CNGB Gene | Repair |
| Acromegaly | Growth hormone receptor | Knockout |
| Acute intermittent porphyria | porphobilinogen deaminase | Repair |
| Adenosine deaminase deficiency (ADA) | Adenosine Deaminase | Repair |
| Alanine-glyoxylate transaminase defect | Alanine-glyoxylate transaminas | Repair |
| Albinism | tyrosinase | Repair |
| Alexander disease | glial fibrillary acidic protein (GFAP) | Repair |
| Aminoacylase 2 deficiency | Alanine-glyoxylate transaminase | Repair |
| Autoimmune Diseases | TNF-alpha, ICAM-1 | Knockout or modulate |
| Color blindness | M-opsin, L-opsin | Repair |
| Complement-Mediated Diseases | | Repair |
| Crigler-Naijar | UGT1A1 | Repair |
| Factor V Leiden thrombophilia | a 1691G | Repair |
| Familial adenomatous polyposis | APC | Repair |
| Familial Chylomicronemia Syndrome (FCS) | ApoC-III | Repair |
| Familial combined hypolipidemia, or hyperlipidemia | ANGPTL3 | Edit to Protective or modulate |
| Fibrosis | CTGF | Knockout or edit in protective variant |
| Friedreich's ataxia | FXN | Repair |
| Gangliosidosis | GM2 | Repair |
| Gaucher disease type I and II | GBA | Repair |
| Glycogen storage disease type II (Pompe disease) | GAA | Repair |

FIGURE 23 cont.

| Disorder | Mutated Genes | Preferred Edit Class |
|---|---|---|
| Hemochromatosis (Haemochromatosis) | HFE | Repair |
| Hemophilia C (Haemophilia) | Factor XI | Repair |
| Hereditary coproporphyria | CPOX | Repair |
| Hereditary deafness | | Repair |
| Iron-overload Disorders | Tmprss6 | Repair |
| Lesch-Nyhan syndrome (Nyhan's syndrome, Kelley-Seegmiller syndrome, and juvenile gout) | HPRT gene | Repair |
| Mixed Hyperlipidemia and HypertriglyceridemiaANGPTL3 | ANGPTL3 | Repair |
| MS and other autoimmune disorders | VLA-4 | Repair or edit to protective |
| Muscular dystrophy (other than becker and dusch, including limb-girdle, congenital, facioscapulohumeral, myotonic, oculopharyngeal, distal, and Emery-Dreifuss muscular dystrophy) | | Repair |
| Myotonic Dystrophy Type 1 | DMPK | Knockout or edit in protective variant |
| NASH | DGAT2 | Knockout or edit in protective variant |
| Neurofibromatosis type I | | Repair |
| Phenylketonuria | phenylalanine hydroxylase (PAH) | Repair |
| Prion disease | PRNP | Repair |
| Smith-Lemli-Opitz syndrome | DHCR7, amino acid position 93 | Repair |
| Spinocerebellar ataxia (SCA) | ATXN1 | Repair |
| Tay–Sachs disease (also known as GM2 gangliosidosis or hexosaminidase A deficiency ) | HEXA | Repair |
| Type 2 tyrosinemia | TAT | Repair |
| alkaptonuria | homogentisic dioxygenase | Repair |
| Biotinidase deficiency | Biotinidase | Repair |
| CADASIL syndrome | NOTCH3 | Repair |

FIGURE 23 cont.

| Disorder | Mutated Genes | Preferred Edit Class |
|---|---|---|
| Canavan disease (Canavan-Van Bogaert-Bertrand disease, aspartoacylase deficiency or aminoacylase 2 deficiency) | ASPA | Repair |
| Carbamyl phosphate synthetase deficiency; ornithine transcarbamylase deficiency, citrullinemia, argininosuccinic aciduria | Carbamyl phosphate synthetase | Repair |
| Charcot–Marie–Tooth disease | Diverse gene/mutations, | Repair |
| Cockayne syndrome Cockayne syndrome (also called Weber-Cockayne syndrome, or Neill-Dingwall syndrome) | ERCC6 and ERCC8 genes | Repair |
| Erythropoietic protoporphyria | | Repair |
| G6PD deficiency | G6PD | Repair |
| Harlequin type ichthyosis | | Repair |
| Hepatic Porphyrias | | Repair |
| Hereditary nonpolyposis colorectal cancer (Lynch syndrome (HNPCC or hereditary nonpolyposis colorectal cancer ) is an) | | Repair |
| Hexoaminindase A Deficieny | | Repair |
| High Blood Pressure | | Modulate activity |
| Homocystinuria | | Repair |
| HTT | | Edit to Protective |
| Hypochondroplasia | | Repair |
| Incontinentia pigmenti "Bloch-Siemens syndrome | | Repair |

FIGURE 23 cont.

| Disorder | Mutated Genes | Preferred Edit Class |
|---|---|---|
| Kniest dysplasia | | Repair |
| Krabbe disease | | Repair |
| Lipoprotein lipase deficiency, familial (Burger-Grutz syndrome, Familial fat-induced hypertriglyceridemia, Familial LPL deficiency, Hyperchylomicronemia, Familial, Hyperlipoproteinemia Type I, Lipase D deficiency, LIPD deficiency, Lipoprotein Lipase Deficiency, Familial) | | Repair |
| Malignant PKU | | Repair |
| Maple Syrup Urine disease | | Repair |
| Maroteaux-Lamy syndrome mucopolysaccharidosis type VI, MPS VI, or polydystrophic dwarfism) | | Repair |
| McLeod syndrome | | Repair |
| Osteogenesis imperfecta (brittle bone disease, or "Lobstein syndrome) | | Repair |
| OTCase Deficiency | | Repair |
| PKK | | Repair |
| Plazomicin Aminoglycoside | | Repair |
| Polycystic kidney disease | PKD-1 | Repair |
| Propionic acidemia | | Repair |
| Pseudo-Gaucher disease (Gaucher-like disease | | Repair |
| Refsum disease | | Repair |
| Sitosterolemia | | Repair |
| Usher syndrome syndrome, Usher-Hallgren syndrome, retinitis pigmentosa-dysacusis syndrome, and dystrophia retinae dysacusis syndrome | | Repair |
| Variegate porphyria | | Repair |

FIGURE 24

| Primary Indication | Target | Editing Oligonucleotide Sequence | Primary Result of Edit | Length | Strand |
|---|---|---|---|---|---|
| Alzheimer's Disease | APP | TCAAGACGGAGGAGATCTCTGAAGTGAAGATGGATgCAGAATTCCGACATGACTCAGGATATGAAGTTCAT (SEQ ID NO. 62) | Ala673 | 71 | Sense |
| Alzheimer's Disease | APP | ATGAACTTCATATCCTGAGTCATGTCGGAATTCTGcATCCATCTTCACTTCAGAGATCTCCTCCGTCTTGA (SEQ ID NO. 63) | Ala673 | 71 | Antisense |
| Alzheimer's Disease | APP | TCTCTGAAGTGAAGATGGATgCAGAATTCCGACATGACTCA (SEQ ID NO. 64) | Ala673 | 41 | Sense |
| Alzheimer's Disease | APP | TGAGTCATGTCGGAATTCTGcATCCATCTTCACTTCAGAGA (SEQ ID NO. 65) | Ala673 | 41 | Antisense |
| Alzheimer's Disease | APP | TCAAGACGGAGGAGATCTCTGAAGTGAAGATGGATaCAGAATTCCGACATGACTCAGGATATGAAGTTCAT (SEQ ID NO. 66) | Thr673 | 71 | Sense |
| Alzheimer's Disease | APP | ATGAACTTCATATCCTGAGTCATGTCGGAATTCTGtATCCATCTTCACTTCAGAGATCTCCTCCGTCTTGA (SEQ ID NO. 67) | Thr673 | 71 | Antisense |
| Alzheimer's Disease | APP | TCTCTGAAGTGAAGATGGATaCAGAATTCCGACATGACTCA (SEQ ID NO. 68) | Thr673 | 41 | Sense |
| Alzheimer's Disease | APP | TGAGTCATGTCGGAATTCTGtATCCATCTTCACTTCAGAGA (SEQ ID NO. 69) | Thr673 | 41 | Antisense |

FIGURE 24 Cont.

| | | | | | |
|---|---|---|---|---|---|
| Alzheimer's Disease | APOE | CGCAGGCCCGGCTGGG CGCGGACATGGAGGAC GTGtGCGGCCGCCTGG TGCAGTACCGCGGCGA GGTGCAG (SEQ ID NO. 70) | Cys130 | 71 | Sense |
| Alzheimer's Disease | APOE | CTGCACCTCGCCGCGG TACTGCACCAGGCGGC CGCaCACGTCCTCCAT GTCCGCGCCCAGCCGG GCCTGCG (SEQ ID NO. 71) | Cys130 | 71 | Antisense |
| Alzheimer's Disease | APOE | GCGCGGACATGGAGGA CGTGtGCGGCCGCCTG GTGCAGTAC (SEQ ID NO. 72) | Cys130 | 41 | Sense |
| Alzheimer's Disease | APOE | GTACTGCACCAGGCGG CCGCaCACGTCCTCCA TGTCCGCGC (SEQ ID NO. 73) | Cys130 | 41 | Antisense |
| Alzheimer's Disease | APOE | AGCGGCTCCTCCGCGA TGCCGATGACCTGCAG AAGcGCCTGGCAGTGT ACCAGGCCGGGGCCCG CGAGGGC (SEQ ID NO. 74) | Arg176 | 71 | Sense |
| Alzheimer's Disease | APOE | GCCCTCGCGGGCCCCG GCCTGGTACACTGCCA GGCgCTTCTGCAGGTC ATCGGCATCGCGGAGG AGCCGCT (SEQ ID NO. 75) | Arg176 | 71 | Antisense |
| Alzheimer's Disease | APOE | ATGCCGATGACCTGCA GAAGcGCCTGGCAGTG TACCAGGCC (SEQ ID NO. 76) | Arg176 | 41 | Sense |
| Alzheimer's Disease | APOE | GGCCTGGTACACTGCC AGGCgCTTCTGCAGGT CATCGGCAT (SEQ ID NO. 77) | Arg176 | 41 | Antisense |
| Alzheimer's Disease | APOE | AGCGGCTCCTCCGCGA TGCCGATGACCTGCAG AAGtGCCTGGCAGTGT ACCAGGCCGGGGCCCG CGAGGGC (SEQ ID NO. 78) | Cys176 | 71 | Sense |

FIGURE 24 Cont.

| Alzheimer's Disease | APOE | GCCCTCGCGGGCCCCG GCCTGGTACACTGCCA GGCaCTTCTGCAGGTC ATCGGCATCGCGGAGG AGCCGCT (SEQ ID NO. 79) | Cys176 | 71 | Antisense |
|---|---|---|---|---|---|
| Alzheimer's Disease | APOE | ATGCCGATGACCTGCA GAAGtGCCTGGCAGTG TACCAGGCC (SEQ ID NO. 80) | Cys176 | 41 | Sense |
| Alzheimer's Disease | APOE | GGCCTGGTACACTGCC AGGCaCTTCTGCAGGT CATCGGCAT (SEQ ID NO. 81) | Cys176 | 41 | Antisense |
| Alzheimer's Disease | APOE | GCGCGGACATGGAGGA CGTGtGCGGCCGCCTG GTGCAGTACCGCGGCG AGGTGCAGGCCATGCT CGGCCAGAGCACCGAG GAGCTGCGGGTGCGCC TCGCCTCCCACCTGCG CAAGCTGCGTAAGCGG CTCCTCCGCGATGCCG ATGACCTGCAGAAGcG CCTGGCAGTGTACCAG GCC (SEQ ID NO. 82) | Cys130, Arg176 | 179 | Sense |
| Alzheimer's Disease | APOE | GGCCTGGTACACTGCC AGGCgCTTCTGCAGGT CATCGGCATCGCGGAG GAGCCGCTTACGCAGC TTGCGCAGGTGGGAGG CGAGGCGCACCCGCAG CTCCTCGGTGCTCTGG CCGAGCATGGCCTGCA CCTCGCCGCGGTACTG CACCAGGCGGCCGCaC ACGTCCTCCATGTCCG CGC (SEQ ID NO. 83) | Cys130, Arg176 | 179 | Antisense |

FIGURE 24 Cont.

| | | | | | |
|---|---|---|---|---|---|
| Alzheimer's Disease | APOE | GCGCGGACATGGAGGA CGTGtGCGGCCGCCTG GTGCAGTACCGCGGCG AGGTGCAGGCCATGCT CGGCCAGAGCACCGAG GAGCTGCGGGTGCGCC TCGCCTCCCACCTGCG CAAGCTGCGTAAGCGG CTCCTCCGCGATGCCG ATGACCTGCAGAAGtG CCTGGCAGTGTACCAG GCC (SEQ ID NO. 84) | Cys130, Arg176 | 179 | Sense |
| Alzheimer's Disease | APOE | GGCCTGGTACACTGCC AGGCaCTTCTGCAGGT CATCGGCATCGCGGAG GAGCCGCTTACGCAGC TTGCGCAGGTGGGAGG CGAGGCGCACCCGCAG CTCCTCGGTGCTCTGG CCGAGCATGGCCTGCA CCTCGCCGCGGTACTG CACCAGGCGGCCGCaC ACGTCCTCCATGTCCG CGC (SEQ ID NO. 85) | Cys130, Arg176 | 179 | Antisense |
| Hemophilia A | F8 | ACCGAAGCTGGTACCT CACAGAGAATATACAA cGCTTTCTCCCCAATC CAGCTGGAGTGCAGCT TGAGGA (SEQ ID NO. 86) | Repair mutation | 70 | Sense |
| Hemophilia A | F8 | TCCTCAAGCTGCACTC CAGCTGGATTGGGGAG AAAGCgTTGTATATTC TCTGTGAGGTACCAGC TTCGGT (SEQ ID NO. 87) | Repair mutation | 70 | Antisense |
| Hemophilia A | F8 | ACCTCACAGAGAATAT ACAAcGCTTTCTCCCC AATCCAGC (SEQ ID NO. 88) | Repair mutation | 40 | Sense |
| Hemophilia A | F8 | GCTGGATTGGGGAGAA AGCgTTGTATATTCTC TGTGAGGT (SEQ ID NO. 89) | Repair mutation | 40 | Antisense |

FIGURE 24 Cont.

| | | | | | |
|---|---|---|---|---|---|
| Hemophilia B | F9 | AGTTCTTCAGTACCTTAGAGTTCCACTTGTTGACCgAGCCACATGTCTTCGATCTACAAAGTTCACCATCT<br>(SEQ ID NO. 90) | Arg379 | 71 | Sense |
| Hemophilia B | F9 | AGATGGTGAACTTTGTAGATCGAAGACATGTGGCTcGGTCAACAAGTGGAACTCTAAGGTACTGAAGAACT<br>(SEQ ID NO. 91) | Arg379 | 71 | Antisense |
| Hemophilia B | F9 | TAGAGTTCCACTTGTTGACCgAGCCACATGTCTTCGATCTA<br>(SEQ ID NO. 92) | Arg379 | 41 | Sense |
| Hemophilia B | F9 | TAGATCGAAGACATGTGGCTcGGTCAACAAGTGGAACTCTA<br>(SEQ ID NO. 93) | Arg379 | 41 | Antisense |
| Sickle cell anemia | HBB | AACCTCAAACAGACACCATGGTGCATCTGACTCCTGaGGAGAAGTCTGCCGTTACTGCCCTGTGGGGCAAGG<br>(SEQ ID NO. 94) | Glu7 or beta thal corr. | 72 | Sense |
| Sickle cell anemia | HBB | CCTTGCCCCACAGGGCAGTAACGGCAGACTTCTCCtCAGGAGTCAGATGCACCATGGTGTCTGTTTGAGGTT<br>(SEQ ID NO. 95) | Glu7 or beta thal corr. | 72 | Antisense |
| Sickle cell anemia | HBB | CATGGTGCATCTGACTCCTGaGGAGAAGTCTGCCGTTACT<br>(SEQ ID NO. 96) | Glu7 or beta thal corr. | 40 | Sense |
| Sickle cell anemia | HBB | AGTAACGGCAGACTTCTCCtCAGGAGTCAGATGCACCATG<br>(SEQ ID NO. 97) | Glu7 or beta thal corr. | 40 | Antisense |
| TTR Amyloidosis | TTR | ATGCTGTCCGAGGCAGTCCTGCCATCAATGTGGCCgTGCATGTGTTCAGAAAGGCTGCTGATGACACCTGG<br>(SEQ ID NO. 98) | Val30 | 71 | Sense |

FIGURE 24 Cont.

| | | | | | |
|---|---|---|---|---|---|
| TTR Amyloidosis | TTR | CCAGGTGTCATCAGCA GCCTTTCTGAACACAT GCAcGGCCACATTGAT GGCAGGACTGCCTCGG ACAGCAT (SEQ ID NO. 99) | Val30 | 71 | Antisense |
| TTR Amyloidosis | TTR | GTCCTGCCATCAATGT GGCCgTGCATGTGTTC AGAAAGGCT (SEQ ID NO. 100) | Val30 | 41 | Sense |
| TTR Amyloidosis | TTR | AGCCTTTCTGAACACA TGCAcGGCCACATTGA TGGCAGGAC (SEQ ID NO. 101) | Val30 | 41 | Antisense |
| Duchenne Musc. Dys. | Dystrop hin | CAAAAACCCAAAATAT TTTgGCTCCTACTCAG ACTGTTAC (SEQ ID NO. 102) | Skip Exon 51 | 40 | Sense |
| Duchenne Musc. Dys. | Dystrop hin | GTAACAGTCTGAGTAG GAGCcAAAATATTTTG GGTTTTTG (SEQ ID NO. 103) | Skip Exon 51 | 40 | Antisense |
| Duchenne Musc. Dys. | Dystrop hin | CTTTTTTCCTTTTTGC AAAAACCCAAAATATT TTgGCTCCTACTCAGA CTGTTACTCTGGTGAC ACAACC (SEQ ID NO. 104) | Skip Exon 51 | 70 | Sense |
| Duchenne Musc. Dys. | Dystrop hin | GGTTGTGTCACCAGAG TAACAGTCTGAGTAGG AGCcAAAATATTTTGG GTTTTTGCAAAAGGA AAAAG (SEQ ID NO. 105) | Skip Exon 51 | 70 | Antisense |
| Cystic Fibrosis | CFTR | GGATTATGCCTGGCAC CATTAAAGAAAATATC ATctTTGGTGTTTCCT ATGATGAATATAGATA CAGAAGC (SEQ ID NO. 106) | Repair DeltaF508 | 71 | Sense |
| Cystic Fibrosis | CFTR | GCTTCTGTATCTATAT TCATCATAGGAAACAC CAaagATGATATTTTC TTTAATGGTGCCAGGC ATAATCC (SEQ ID NO. 107) | Repair DeltaF508 | 71 | Antisense |

FIGURE 24 Cont.

| Cystic Fibrosis | CFTR | CCATTAAAGAAAATAT CATcttTGGTGTTTCC TATGATGAA (SEQ ID NO. 108) | Repair DeltaF508 | 41 | Sense |
|---|---|---|---|---|---|
| Cystic Fibrosis | CFTR | TTCATCATAGGAAACA CCAaagATGATATTTT CTTTAATGG (SEQ ID NO. 109) | Repair DeltaF508 | 41 | Antisense |
| Cystic Fibrosis | CFTR | TTCTGTATCTATATTC ATCATAGGAAACACCA aagATAATGTTCTCCT TAATGGTGCCAGG (SEQ ID NO. 110) | Repair DeltaF508 | 61 | Antisense |

3' terminal segment

3' proximal segment

3' editing segment editing site

5' editing segment

5' proximal segment

5' terminal segment

SEQUENCE LISTING

```
<160> NUMBER OF SEQ ID NOS: 110

<210> SEQ ID NO 1
<211> LENGTH: 72
<212> TYPE: DNA
<213> ORGANISM: Artificial Sequence
<220> FEATURE:
<223> OTHER INFORMATION: Synthetic oligonucleotide (ETAGEN Serial Number
      100001)
<220> FEATURE:
<221> NAME/KEY: misc_feature
<222> LOCATION: (1)..(72)
<223> OTHER INFORMATION: Base modification: 3 phosphorothioates
      end-blocks on each terminus

<400> SEQUENCE: 1
catgtggtcg gggtagcggc tgaagcactg cacgccgtag gtcagggtgg tcacgagggt    60
gggccagggc ac                                                        72

<210> SEQ ID NO 2
<211> LENGTH: 72
```

```
<212> TYPE: DNA
<213> ORGANISM: Artificial Sequence
<220> FEATURE:
<223> OTHER INFORMATION: Synthetic oligonucleotide (ETAGEN Serial Number
      100002)
<220> FEATURE:
<221> NAME/KEY: misc_feature
<222> LOCATION: (1)..(72)
<223> OTHER INFORMATION: Base modification: 3 phosphorothioates
      end-blocks on each terminus

<400> SEQUENCE: 2
catgtggtcg gggtagcggc tgaagcactg cacgccctag gtcagggtgg tcacgagggt    60
gggccagggc ac                                                       72

<210> SEQ ID NO 3
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100003)

<400> SEQUENCE: 3
cggctgaagc actgcacgcc gtaggtcagg gtggtcacga                         40

<210> SEQ ID NO 4
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100004)

<400> SEQUENCE: 4
cggctgaagc actgcacgcc ctaggtcagg gtggtcacga                         40

<210> SEQ ID NO 5
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100005)
<220> FEATURE:
<221> NAME/KEY: misc_feature
<222> LOCATION: (1)..(40)
<223> OTHER INFORMATION: Base modification: 3 phosphorothioates
      end-blocks on each terminus (Parent)

<400> SEQUENCE: 5
cggctgaagc actgcacgcc gtaggtcagg gtggtcacga                         40

<210> SEQ ID NO 6
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100006)
<220> FEATURE:
<221> NAME/KEY: misc_feature
<222> LOCATION: (1)..(40)
<223> OTHER INFORMATION: Base modification: 3 phosphorothioates
      end-blocks on each terminus

<400> SEQUENCE: 6
cggctgaagc actgcacgcc ctaggtcagg gtggtcacga                         40
```

<210> SEQ ID NO 7
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number 100007)
<220> FEATURE:
<221> NAME/KEY: misc_feature
<222> LOCATION: (1)..(40)
<223> OTHER INFORMATION: Base modification: half phosphorothioates positive 40 mer (9s-20o-10s) with unmodified editing region

<400> SEQUENCE: 7
cggctgaagc actgcacgcc gtaggtcagg gtggtcacga                          40

<210> SEQ ID NO 8
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number 100008)
<220> FEATURE:
<221> NAME/KEY: misc_feature
<222> LOCATION: (1)..(40)
<223> OTHER INFORMATION: Base modification: half phosphorothioates positive 40 mer (9s-20o-10s) with unmodified editing region

<400> SEQUENCE: 8
cggctgaagc actgcacgcc ctaggtcagg gtggtcacga                          40

<210> SEQ ID NO 9
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number 100009)
<220> FEATURE:
<221> NAME/KEY: misc_feature
<222> LOCATION: (1)..(40)
<223> OTHER INFORMATION: Base modification: half phosphorothioates positive 40 mer (9s-20o-10s) with unmodified editing region

<400> SEQUENCE: 9
ctgcgagatc gcggcagcgc catgctgagg ctcgtacaga                          40

<210> SEQ ID NO 10
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number 100010)
<220> FEATURE:
<221> NAME/KEY: misc_feature
<222> LOCATION: (1)..(40)
<223> OTHER INFORMATION: Base modification: Majority phosphorothiotes except in editing region (16s-6o-17s)

<400> SEQUENCE: 10
cggctgaagc actgcacgcc gtaggtcagg gtggtcacga                          40

<210> SEQ ID NO 11
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number 100011)
<220> FEATURE:
<221> NAME/KEY: misc_feature
<222> LOCATION: (1)..(40)
<223> OTHER INFORMATION: Base modification: Majority phosphorothiotes
      except in editing region (16s-6o-17s)

<400> SEQUENCE: 11
cggctgaagc actgcacgcc ctaggtcagg gtggtcacga                         40

<210> SEQ ID NO 12
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100012)
<220> FEATURE:
<221> NAME/KEY: misc_feature
<222> LOCATION: (1)..(40)
<223> OTHER INFORMATION: Base modification: Majority phosphorothiotes
      except in editing region (16s-6o-17s)

<400> SEQUENCE: 12
ctgcgagatc gcggcagcgc catgctgagg ctcgtacaga                         40

<210> SEQ ID NO 13
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100013)
<220> FEATURE:
<221> NAME/KEY: misc_feature
<222> LOCATION: (1)..(40)
<223> OTHER INFORMATION: Base modification: 3' 8x2'F high affinity arms
      with s end-blocks

<400> SEQUENCE: 13
cggctgaagc actgcacgcc gtaggtcagg gtggtcacga                         40

<210> SEQ ID NO 14
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100014)
<220> FEATURE:
<221> NAME/KEY: misc_feature
<222> LOCATION: (1)..(40)
<223> OTHER INFORMATION: Base modification: 3' 8x2'F high affinity arms
      with s end-blocks

<400> SEQUENCE: 14
cggctgaagc actgcacgcc ctaggtcagg gtggtcacga                         40

<210> SEQ ID NO 15
<211> LENGTH: 42
<212> TYPE: DNA
<213> ORGANISM: Artificial Sequence
<220> FEATURE:
<223> OTHER INFORMATION: Synthetic oligonucleotide (ETAGEN Serial Number
      100015)
<220> FEATURE:
<221> NAME/KEY: misc_feature
<222> LOCATION: (1)..(42)
<223> OTHER INFORMATION: Base modification: 5' non-phosphorothioate
      end-block (methyphosphonate), 3' 3s end-blocks

```
<400> SEQUENCE: 15
ttcggctgaa gcactgcacg ccgtaggtca gggtggtcac ga          42

<210> SEQ ID NO 16
<211> LENGTH: 42
<212> TYPE: DNA
<213> ORGANISM: Artificial Sequence
<220> FEATURE:
<223> OTHER INFORMATION: Synthetic oligonucleotide (ETAGEN Serial Number
      100016)
<220> FEATURE:
<221> NAME/KEY: misc_feature
<222> LOCATION: (1)..(42)
<223> OTHER INFORMATION: Base modification: 5' non-phosphorothioate
      end-block (methyphosphonate), 3' 3s end-blocks

<400> SEQUENCE: 16
ttcggctgaa gcactgcacg ccctaggtca gggtggtcac ga          42

<210> SEQ ID NO 17
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100017)
<220> FEATURE:
<221> NAME/KEY: misc_feature
<222> LOCATION: (1)..(40)
<223> OTHER INFORMATION: Base modification: C's replaced with 5' methyl
      C to fool repair machinery, as to which strand is nascent

<400> SEQUENCE: 17
cggctgaagc actgcacgcc gtaggtcagg gtggtcacga              40

<210> SEQ ID NO 18
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100018)
<220> FEATURE:
<221> NAME/KEY: misc_feature
<222> LOCATION: (1)..(40)
<223> OTHER INFORMATION: Base modification: C's replaced with 5' methyl
      C to fool repair machinery, as to which strand is nascent

<400> SEQUENCE: 18
cggctgaagc actgcacgcc ctaggtcagg gtggtcacga              40

<210> SEQ ID NO 19
<211> LENGTH: 13
<212> TYPE: RNA
<213> ORGANISM: Artificial Sequence
<220> FEATURE:
<223> OTHER INFORMATION: Synthetic oligonucleotide (ETAGEN Serial Number
      100019)
<220> FEATURE:
<221> NAME/KEY: misc_feature
<222> LOCATION: (1)..(13)
<223> OTHER INFORMATION: Base modification: 2'-O-methyl "protector"
      oligo complimentary to positions 1-13 of editing oligo

<400> SEQUENCE: 19
agugcuucag ccg                                           13

<210> SEQ ID NO 20
<211> LENGTH: 14
```

-continued

```
<212> TYPE: RNA
<213> ORGANISM: Artificial Sequence
<220> FEATURE:
<223> OTHER INFORMATION: Synthetic oligonucleotide (ETAGEN Serial Number
      100020)
<220> FEATURE:
<221> NAME/KEY: misc_feature
<222> LOCATION: (1)..(14)
<223> OTHER INFORMATION: Base modification: 2' -O-methyl "protector"
      oligo complimentary to positions 14-27 of editing oligo

<400> SEQUENCE: 20
gaccuacggc gugc                                                         14

<210> SEQ ID NO 21
<211> LENGTH: 13
<212> TYPE: RNA
<213> ORGANISM: Artificial Sequence
<220> FEATURE:
<223> OTHER INFORMATION: Synthetic oligonucleotide (ETAGEN Serial Number
      100021)
<220> FEATURE:
<221> NAME/KEY: misc_feature
<222> LOCATION: (1)..(13)
<223> OTHER INFORMATION: Base modification: 2' -O-methyl "protector"
      oligo complimentary to positions 28-40 of editing oligo

<400> SEQUENCE: 21
ucgugaccac ccu                                                          13

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide (ETAGEN Serial Number
      100022)
<220> FEATURE:
<221> NAME/KEY: misc_feature
<222> LOCATION: (1)..(25)
<223> OTHER INFORMATION: Base modification: 25mer all phosphorothioate
      DNA

<400> SEQUENCE: 22
gcactgcacg ccctaggtca gggtg                                             25

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide (ETAGEN Serial Number
      100023)
<220> FEATURE:
<221> NAME/KEY: misc_feature
<222> LOCATION: (1)..(25)
<223> OTHER INFORMATION: Base modification: 25mer all phosphorothioate
      DNA

<400> SEQUENCE: 23
gcactgcacg ccgtaggtca gggtg                                             25

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide (ETAGEN Serial Number
      100024)
<220> FEATURE:
<221> NAME/KEY: misc_feature
```

```
<222> LOCATION: (1)..(25)
<223> OTHER INFORMATION: Base modification: 25mer all phosphorothioate
      DNA

<400> SEQUENCE: 24
tcgcggcagc gccatgctga ggatc                                           25

<210> SEQ ID NO 25
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100031)
<220> FEATURE:
<221> NAME/KEY: misc_feature
<222> LOCATION: (1)..(40)
<223> OTHER INFORMATION: Base modification: 3 phosphorothioates
      end-blocks on each terminus (PARENT)

<400> SEQUENCE: 25
cggctgaagc actgcacgcc gtaggtcagg gtggtcacga                           40

<210> SEQ ID NO 26
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100032)
<220> FEATURE:
<221> NAME/KEY: misc_feature
<222> LOCATION: (1)..(40)
<223> OTHER INFORMATION: Base modification: 40mers (with 3
      phosphorothioates on each terminus)

<400> SEQUENCE: 26
cggctgaagc actgcacgcc ctaggtcagg gtggtcacga                           40

<210> SEQ ID NO 27
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100033)
<220> FEATURE:
<221> NAME/KEY: misc_feature
<222> LOCATION: (1)..(40)
<223> OTHER INFORMATION: Base modification: 5' and 3' 8x2'F high
      affinity arms with s end-blocks

<400> SEQUENCE: 27
cggctgaagc actgcacgcc ctaggtcagg gtggtcacga                           40

<210> SEQ ID NO 28
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100034)
<220> FEATURE:
<221> NAME/KEY: misc_feature
<222> LOCATION: (1)..(40)
<223> OTHER INFORMATION: Base modification: 5' and 3' 8x2'F high
      affinity arms with s end-blocks

<400> SEQUENCE: 28
cggctgaagc actgcacgcc gtaggtcagg gtggtcacga                           40
```

```
<210> SEQ ID NO 29
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100035)
<220> FEATURE:
<221> NAME/KEY: misc_feature
<222> LOCATION: (1)..(40)
<223> OTHER INFORMATION: Base modification: 3' 8x2'-O-methyl high
      affinity arms with s end-blocks

<400> SEQUENCE: 29
cggctgaagc actgcacgcc gtaggtcagg gtggtcacga                              40

<210> SEQ ID NO 30
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100036)
<220> FEATURE:
<221> NAME/KEY: misc_feature
<222> LOCATION: (1)..(40)
<223> OTHER INFORMATION: Base modification: 3' 8x2'-O-methyl high
      affinity arms with s end-blocks

<400> SEQUENCE: 30
cggctgaagc actgcacgcc ctaggtcagg gtggtcacga                              40

<210> SEQ ID NO 31
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100037)
<220> FEATURE:
<221> NAME/KEY: misc_feature
<222> LOCATION: (1)..(40)
<223> OTHER INFORMATION: Base modification: 5' 8x2'-O-methyl high
      affinity arms with s end-blocks

<400> SEQUENCE: 31
cggctgaagc actgcacgcc gtaggtcagg gtggtcacga                              40

<210> SEQ ID NO 32
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100038)
<220> FEATURE:
<221> NAME/KEY: misc_feature
<222> LOCATION: (1)..(40)
<223> OTHER INFORMATION: Base modification: 5' 8x2'-O-methyl high
      affinity arms with s end-blocks

<400> SEQUENCE: 32
cggctgaagc actgcacgcc ctaggtcagg gtggtcacga                              40

<210> SEQ ID NO 33
<211> LENGTH: 40
<212> TYPE: DNA
<213> ORGANISM: Artificial Sequence
<220> FEATURE:
```

```
<223> OTHER INFORMATION: Synthetic oligonucleotide (ETAGEN Serial Number
      100039)
<220> FEATURE:
<221> NAME/KEY: misc_feature
<222> LOCATION: (1)..(40)
<223> OTHER INFORMATION: Base modification: 5' and 3' 8x2'-O-methyl high
      affinity arms with s end-blocks

<400> SEQUENCE: 33
cggctgaagc actgcacgcc ctaggtcagg gtggtcacga                            40

<210> SEQ ID NO 34
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100040)
<220> FEATURE:
<221> NAME/KEY: misc_feature
<222> LOCATION: (1)..(40)
<223> OTHER INFORMATION: Base modification: 5' and 3' 8x2'-O-methyl high
      affinity arms with s end-blocks

<400> SEQUENCE: 34
cggctgaagc actgcacgcc gtaggtcagg gtggtcacga                            40

<210> SEQ ID NO 35
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100041)
<220> FEATURE:
<221> NAME/KEY: misc_feature
<222> LOCATION: (1)..(40)
<223> OTHER INFORMATION: Base modification: Central C's replaced with 5'
      methyl C to fool repair machinery as to which strand is nascent

<400> SEQUENCE: 35
cggctgaagc actgcacgcc ctaggtcagg gtggtcacga                            40

<210> SEQ ID NO 36
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100042)
<220> FEATURE:
<221> NAME/KEY: misc_feature
<222> LOCATION: (1)..(40)
<223> OTHER INFORMATION: Base modification: Central C's replaced with 5'
      methyl C to fool repair machinery as to which strand is nascent

<400> SEQUENCE: 36
cggctgaagc actgcacgcc gtaggtcagg gtggtcacga                            40

<210> SEQ ID NO 37
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100043)
<220> FEATURE:
<221> NAME/KEY: misc_feature
<222> LOCATION: (1)..(40)
<223> OTHER INFORMATION: Base modification: Central C replaced with 5'
      methyl C to fool repair machinery as to which strand is nascent
```

```
<400> SEQUENCE: 37
cggctgaagc actgcacgcc gtaggtcagg gtggtcacga                        40

<210> SEQ ID NO 38
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100044)
<220> FEATURE:
<221> NAME/KEY: misc_feature
<222> LOCATION: (1)..(40)
<223> OTHER INFORMATION: Base modification: Central C replaced with 5'
      methyl C to fool repair machinery as to which strand is nascent

<400> SEQUENCE: 38
cggctgaagc actgcacgcc ctaggtcagg gtggtcacga                        40

<210> SEQ ID NO 39
<211> LENGTH: 44
<212> TYPE: DNA
<213> ORGANISM: Artificial Sequence
<220> FEATURE:
<223> OTHER INFORMATION: Synthetic oligonucleotide (ETAGEN Serial Number
      100045)
<220> FEATURE:
<221> NAME/KEY: misc_feature
<222> LOCATION: (1)..(44)
<223> OTHER INFORMATION: Base modification: Phosphorothiote-free
      methylphosphonoate end-blocks, 5 methyl C's and 2'F arms

<400> SEQUENCE: 39
ttcggctgaa gcactgcacg ccgtaggtca gggtggtcac gatt                   44

<210> SEQ ID NO 40
<211> LENGTH: 42
<212> TYPE: DNA
<213> ORGANISM: Artificial Sequence
<220> FEATURE:
<223> OTHER INFORMATION: Synthetic oligonucleotide (ETAGEN Serial Number
      100047)
<220> FEATURE:
<221> NAME/KEY: misc_feature
<222> LOCATION: (1)..(42)
<223> OTHER INFORMATION: Base modification: 5' methylphosphonoate
      end-blocks, 3' s-end-blocks, 5 methyl C's and 3' 2'F arm

<400> SEQUENCE: 40
ttcggctgaa gcactgcacg ccgtaggtca gggtggtcac ga                     42

<210> SEQ ID NO 41
<211> LENGTH: 42
<212> TYPE: DNA
<213> ORGANISM: Artificial Sequence
<220> FEATURE:
<223> OTHER INFORMATION: Synthetic oligonucleotide (ETAGEN Serial Number
      100048)
<220> FEATURE:
<221> NAME/KEY: misc_feature
<222> LOCATION: (1)..(42)
<223> OTHER INFORMATION: Base modification: 5' methylphosphonoate
      end-blocks, 3' s-end-blocks, 5 methyl C's and 3' 2'F arm

<400> SEQUENCE: 41
ttcggctgaa gcactgcacg ccctaggtca gggtggtcac ga                     42

<210> SEQ ID NO 42
```

```
<211> LENGTH: 44
<212> TYPE: DNA
<213> ORGANISM: Artificial Sequence
<220> FEATURE:
<223> OTHER INFORMATION: Synthetic oligonucleotide (ETAGEN Serial Number
      100049)
<220> FEATURE:
<221> NAME/KEY: misc_feature
<222> LOCATION: (1)..(44)
<223> OTHER INFORMATION: Base modification: Phosphorothioate-free 5' and
      3' methylphosphonate end-blocks

<400> SEQUENCE: 42
ttcggctgaa gcactgcacg ccctaggtca gggtggtcac gatt             44

<210> SEQ ID NO 43
<211> LENGTH: 44
<212> TYPE: DNA
<213> ORGANISM: Artificial Sequence
<220> FEATURE:
<223> OTHER INFORMATION: Synthetic oligonucleotide (ETAGEN Serial Number
      100050)
<220> FEATURE:
<221> NAME/KEY: misc_feature
<222> LOCATION: (1)..(44)
<223> OTHER INFORMATION: Base modification: Phosphorothioate-free 5' and
      3' methylphosphonate end-blocks

<400> SEQUENCE: 43
ttcggctgaa gcactgcacg ccgtaggtca gggtggtcac gatt             44

<210> SEQ ID NO 44
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100058)
<220> FEATURE:
<221> NAME/KEY: misc_feature
<222> LOCATION: (1)..(40)
<223> OTHER INFORMATION: Base modification: 5' 8x2'-O-methyl and 8x3'
      2'F high affinity arms with s end-blocks

<400> SEQUENCE: 44
cggctgaagc actgcacgcc gtaggtcagg gtggtcacga                  40

<210> SEQ ID NO 45
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100060)
<220> FEATURE:
<221> NAME/KEY: misc_feature
<222> LOCATION: (1)..(40)
<223> OTHER INFORMATION: Base modification: 5' 8x2'-O-methyl and 3'
      8x2'F high affinity arms with s end-blocks, with central 5 Methyl
      Cs

<400> SEQUENCE: 45
cggctgaagc actgcacgcc gtaggtcagg gtggtcacga                  40

<210> SEQ ID NO 46
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100062)
```

```
<220> FEATURE:
<221> NAME/KEY: misc_feature
<222> LOCATION: (1)..(40)
<223> OTHER INFORMATION: Base modification: 3' 14x2'F high affinity arms
      with s end-blocks

<400> SEQUENCE: 46
cggctgaagc actgcacgcc gtaggtcagg gtggtcacga                              40

<210> SEQ ID NO 47
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100064)
<220> FEATURE:
<221> NAME/KEY: misc_feature
<222> LOCATION: (1)..(40)
<223> OTHER INFORMATION: Base modification: 3' 20x2'F high affinity arms
      with s end-blocks

<400> SEQUENCE: 47
cggctgaagc actgcacgcc gtaggtcagg gtggtcacga                              40

<210> SEQ ID NO 48
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100066)
<220> FEATURE:
<221> NAME/KEY: misc_feature
<222> LOCATION: (1)..(40)
<223> OTHER INFORMATION: Base modification: 5' 14x2'-O-methyl high
      affinity arms with s end-blocks

<400> SEQUENCE: 48
cggctgaagc actgcacgcc gtaggtcagg gtggtcacga                              40

<210> SEQ ID NO 49
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100068)
<220> FEATURE:
<221> NAME/KEY: misc_feature
<222> LOCATION: (1)..(40)
<223> OTHER INFORMATION: Base modification: 5' 20x2'-O-methyl high
      affinity arms with s end-blocks

<400> SEQUENCE: 49
cggctgaagc actgcacgcc gtaggtcagg gtggtcacga                              40

<210> SEQ ID NO 50
<211> LENGTH: 72
<212> TYPE: DNA
<213> ORGANISM: Artificial Sequence
<220> FEATURE:
<223> OTHER INFORMATION: Synthetic oligonucleotide (ETAGEN Serial Number
      100070)
<220> FEATURE:
<221> NAME/KEY: misc_feature
<222> LOCATION: (1)..(72)
<223> OTHER INFORMATION: Base modification: 5' 8x2'-O-methyl high
      affinity arms with s end-blocks

<400> SEQUENCE: 50
```
catgtggtcg gggtagcggc tgaagcactg cacgccgtag gtcagggtgg tcacgagggt    60
gggccagggc ac    72

<210> SEQ ID NO 51
<211> LENGTH: 72
<212> TYPE: DNA
<213> ORGANISM: Artificial Sequence
<220> FEATURE:
<223> OTHER INFORMATION: Synthetic oligonucleotide (ETAGEN Serial Number
      100072)
<220> FEATURE:
<221> NAME/KEY: misc_feature
<222> LOCATION: (1)..(72)
<223> OTHER INFORMATION: Base modification: 5' 24x2'-O-methyl high
      affinity arms with s end-blocks

<400> SEQUENCE: 51
catgtggtcg gggtagcggc tgaagcactg cacgccgtag gtcagggtgg tcacgagggt    60
gggccagggc ac    72

<210> SEQ ID NO 52
<211> LENGTH: 44
<212> TYPE: DNA
<213> ORGANISM: Artificial Sequence
<220> FEATURE:
<223> OTHER INFORMATION: Synthetic oligonucleotide (ETAGEN Serial Number
      100074)
<220> FEATURE:
<221> NAME/KEY: misc_feature
<222> LOCATION: (1)..(44)
<223> OTHER INFORMATION: Base modification: end-block 3'
      phosphorothioate end-block

<400> SEQUENCE: 52
cggctgaagc actgcacgcc gtaggtcagg gtggtcacga cgcg    44

<210> SEQ ID NO 53
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100076)
<220> FEATURE:
<221> NAME/KEY: misc_feature
<222> LOCATION: (1)..(40)
<223> OTHER INFORMATION: Base modification: amino linker (TriLink
      Biotechnologies, San Diego, CA) end-blocks

<400> SEQUENCE: 53
cggctgaagc actgcacgcc gtaggtcagg gtggtcacga    40

<210> SEQ ID NO 54
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100078)
<220> FEATURE:
<221> NAME/KEY: misc_feature
<222> LOCATION: (1)..(40)
<223> OTHER INFORMATION: Base modification:  5' and 3' end-blocks

<400> SEQUENCE: 54
cggctgaagc actgcacgcc gtaggtcagg gtggtcacga    40

```
<210> SEQ ID NO 55
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100079)
<220> FEATURE:
<221> NAME/KEY: misc_feature
<222> LOCATION: (1)..(40)
<223> OTHER INFORMATION: Base modification: amino linkers 5' and 3'
      end-blocks (TriLink Biotechnologies, San Diego, CA)

<400> SEQUENCE: 55
cggctgaagc actgcacgcc gtaggtcagg gtggtcacga                              40

<210> SEQ ID NO 56
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100080)
<220> FEATURE:
<221> NAME/KEY: misc_feature
<222> LOCATION: (1)..(40)
<223> OTHER INFORMATION: Base modification: Amino Linker end-blocks with
      3' 10x2'F arm 5' 11x2'-O-methyl and 5 Methyl C editing region

<400> SEQUENCE: 56
cggctgaagc actgcacgcc gtaggtcagg gtggtcacga                              40

<210> SEQ ID NO 57
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100082)
<220> FEATURE:
<221> NAME/KEY: misc_feature
<222> LOCATION: (1)..(40)
<223> OTHER INFORMATION: Base modification: COMPLEMENTARY DNA STRAND TO
      THE PARENT with phosphorothioate end-blocks

<400> SEQUENCE: 57
tcgtgaccac cctgacctac ggcgtgcagt gcttcagccg                              40

<210> SEQ ID NO 58
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100083)
<220> FEATURE:
<221> NAME/KEY: misc_feature
<222> LOCATION: (1)..(40)
<223> OTHER INFORMATION: Base modification: COMPLEMENTARY RNA STRAND TO
      THE PARENT with phosphorothioate end-blocks

<400> SEQUENCE: 58
tcgtgaccac cctgacctac ggcgtgcagt gcttcagccg                              40

<210> SEQ ID NO 59
<211> LENGTH: 40
<212> TYPE: DNA
<213> ORGANISM: Artificial Sequence
<220> FEATURE:
<223> OTHER INFORMATION: Synthetic oligonucleotide (ETAGEN Serial Number
      100084)
```

```
<220> FEATURE:
<221> NAME/KEY: misc_feature
<222> LOCATION: (1)..(40)
<223> OTHER INFORMATION: Base modification: 5' 8xRNA and 3' 8x2'F high
      affinity arms with s end-blocks

<400> SEQUENCE: 59
cggctgaagc actgcacgcc gtaggtcagg gtggtcacga                              40

<210> SEQ ID NO 60
<211> LENGTH: 72
<212> TYPE: DNA
<213> ORGANISM: Artificial Sequence
<220> FEATURE:
<223> OTHER INFORMATION: Synthetic oligonucleotide (ETAGEN Serial Number
      100085)
<220> FEATURE:
<221> NAME/KEY: misc_feature
<222> LOCATION: (1)..(72)
<223> OTHER INFORMATION: Base modification: Editing/Guide Strand with 5'
      RISC entry site of alternating RNA/2'-O-methyl

<400> SEQUENCE: 60
catgtggtcg gggtagcggc tgaagcactg cacgccgtag gtcagggtgg tcacgagggt        60
gggccagggc ac                                                           72

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide (ETAGEN Serial Number
      100086)
<220> FEATURE:
<221> NAME/KEY: misc_feature
<222> LOCATION: (1)..(21)
<223> OTHER INFORMATION: Base modification: Sense strand that will allow
      the duplex with 100085 to form editing compound capable of RISC
      entry

<400> SEQUENCE: 61
ccgctacccc gaccacatgt t                                                  21

<210> SEQ ID NO 62
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APP)

<400> SEQUENCE: 62
tcaagacgga ggagatctct gaagtgaaga tggatgcaga attccgacat gactcaggat        60
atgaagttca t                                                            71

<210> SEQ ID NO 63
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APP)

<400> SEQUENCE: 63
atgaacttca tatcctgagt catgtcggaa ttctgcatcc atcttcactt cagagatctc        60
ctccgtcttg a                                                            71
```

<210> SEQ ID NO 64
<211> LENGTH: 41
<212> TYPE: DNA
<213> ORGANISM: Artificial Sequence
<220> FEATURE:
<223> OTHER INFORMATION: Synthetic oligonucleotide (Primary Indication:
   Alzheimer's Disease; Target: APP)

<400> SEQUENCE: 64
tctctgaagt gaagatggat gcagaattcc gacatgactc a                    41

<210> SEQ ID NO 65
<211> LENGTH: 41
<212> TYPE: DNA
<213> ORGANISM: Artificial Sequence
<220> FEATURE:
<223> OTHER INFORMATION: Synthetic oligonucleotide (Primary Indication:
   Alzheimer's Disease; Target: APP)

<400> SEQUENCE: 65
tgagtcatgt cggaattctg catccatctt cacttcagag a                    41

<210> SEQ ID NO 66
<211> LENGTH: 71
<212> TYPE: DNA
<213> ORGANISM: Artificial Sequence
<220> FEATURE:
<223> OTHER INFORMATION: Synthetic oligonucleotide (Primary Indication:
   Alzheimer's Disease; Target: APP)

<400> SEQUENCE: 66
tcaagacgga ggagatctct gaagtgaaga tggatacaga attccgacat gactcaggat    60
atgaagttca t                                                         71

<210> SEQ ID NO 67
<211> LENGTH: 71
<212> TYPE: DNA
<213> ORGANISM: Artificial Sequence
<220> FEATURE:
<223> OTHER INFORMATION: Synthetic oligonucleotide (Primary Indication:
   Alzheimer's Disease; Target: APP)

<400> SEQUENCE: 67
atgaacttca tatcctgagt catgtcggaa ttctgtatcc atcttcactt cagagatctc    60
ctccgtcttg a                                                         71

<210> SEQ ID NO 68
<211> LENGTH: 41
<212> TYPE: DNA
<213> ORGANISM: Artificial Sequence
<220> FEATURE:
<223> OTHER INFORMATION: Synthetic oligonucleotide (Primary Indication:
   Alzheimer's Disease; Target: APP)

<400> SEQUENCE: 68
tctctgaagt gaagatggat acagaattcc gacatgactc a                    41

<210> SEQ ID NO 69
<211> LENGTH: 41
<212> TYPE: DNA
<213> ORGANISM: Artificial Sequence
<220> FEATURE:
<223> OTHER INFORMATION: Synthetic oligonucleotide (Primary Indication:
   Alzheimer's Disease; Target: APP)

<400> SEQUENCE: 69
tgagtcatgt cggaattctg tatccatctt cacttcagag a         41

<210> SEQ ID NO 70
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 70
cgcaggcccg gctgggcgcg gacatggagg acgtgtgcgg ccgcctggtg cagtaccgcg         60
gcgaggtgca g         71

<210> SEQ ID NO 71
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 71
ctgcacctcg ccgcggtact gcaccaggcg gccgcacacg tcctccatgt ccgcgcccag         60
ccgggcctgc g         71

<210> SEQ ID NO 72
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 72
gcgcggacat ggaggacgtg tgcggccgcc tggtgcagta c         41

<210> SEQ ID NO 73
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 73
gtactgcacc aggcggccgc acacgtcctc catgtccgcg c         41

<210> SEQ ID NO 74
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 74
agcggctcct ccgcgatgcc gatgacctgc agaagcgcct ggcagtgtac caggccgggg         60
cccgcgaggg c         71

<210> SEQ ID NO 75
<211> LENGTH: 71
<212> TYPE: DNA
<213> ORGANISM: Artificial Sequence

```
<220> FEATURE:
<223> OTHER INFORMATION: Synthetic oligonucleotide (Primary Indication:
      Alzheimer's Disease; Target: APOE)

<400> SEQUENCE: 75
gccctcgcgg gccccggcct ggtacactgc caggcgcttc tgcaggtcat cggcatcgcg    60
gaggagccgc t                                                          71

<210> SEQ ID NO 76
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 76
atgccgatga cctgcagaag cgcctggcag tgtaccaggc c                         41

<210> SEQ ID NO 77
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 77
ggcctggtac actgccaggc gcttctgcag gtcatcggca t                         41

<210> SEQ ID NO 78
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 78
agcggctcct ccgcgatgcc gatgacctgc agaagtgcct ggcagtgtac caggccgggg    60
cccgcgaggg c                                                          71

<210> SEQ ID NO 79
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 79
gccctcgcgg gccccggcct ggtacactgc caggcacttc tgcaggtcat cggcatcgcg    60
gaggagccgc t                                                          71

<210> SEQ ID NO 80
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      Alzheimer's Disease; Target: APOE)

<400> SEQUENCE: 80
atgccgatga cctgcagaag tgcctggcag tgtaccaggc c                         41
```

<210> SEQ ID NO 81
<211> LENGTH: 41
<212> TYPE: DNA
<213> ORGANISM: Artificial Sequence
<220> FEATURE:
<223> OTHER INFORMATION: Synthetic oligonucleotide (Primary Indication:
    Alzheimer's Disease; Target: APOE)

<400> SEQUENCE: 81
ggcctggtac actgccaggc acttctgcag gtcatcggca t                      41

<210> SEQ ID NO 82
<211> LENGTH: 179
<212> TYPE: DNA
<213> ORGANISM: Artificial Sequence
<220> FEATURE:
<223> OTHER INFORMATION: Synthetic oligonucleotide (Primary Indication:
    Alzheimer's Disease; Target: APOE)

<400> SEQUENCE: 82
gcgcggacat ggaggacgtg tgcggccgcc tggtgcagta ccgcggcgag gtgcaggcca     60
tgctcggcca gagcaccgag gagctgcggg tgcgcctcgc ctcccacctg cgcaagctgc    120
gtaagcggct cctccgcgat gccgatgacc tgcagaagcg cctggcagtg taccaggcc    179

<210> SEQ ID NO 83
<211> LENGTH: 179
<212> TYPE: DNA
<213> ORGANISM: Artificial Sequence
<220> FEATURE:
<223> OTHER INFORMATION: Synthetic oligonucleotide (Primary Indication:
    Alzheimer's Disease; Target: APOE)

<400> SEQUENCE: 83
ggcctggtac actgccaggc gcttctgcag gtcatcggca tcgcggagga gccgcttacg     60
cagcttgcgc aggtgggagg cgaggcgcac ccgcagctcc tcggtgctct ggccgagcat    120
ggcctgcacc tcgccgcggt actgcaccag gcggccgcac acgtcctcca tgtccgcgc    179

<210> SEQ ID NO 84
<211> LENGTH: 179
<212> TYPE: DNA
<213> ORGANISM: Artificial Sequence
<220> FEATURE:
<223> OTHER INFORMATION: Synthetic oligonucleotide (Primary Indication:
    Alzheimer's Disease; Target: APOE)

<400> SEQUENCE: 84
gcgcggacat ggaggacgtg tgcggccgcc tggtgcagta ccgcggcgag gtgcaggcca     60
tgctcggcca gagcaccgag gagctgcggg tgcgcctcgc ctcccacctg cgcaagctgc    120
gtaagcggct cctccgcgat gccgatgacc tgcagaagtg cctggcagtg taccaggcc    179

<210> SEQ ID NO 85
<211> LENGTH: 179
<212> TYPE: DNA
<213> ORGANISM: Artificial Sequence
<220> FEATURE:
<223> OTHER INFORMATION: Synthetic oligonucleotide (Primary Indication:
    Alzheimer's Disease; Target: APOE)

<400> SEQUENCE: 85
ggcctggtac actgccaggc acttctgcag gtcatcggca tcgcggagga gccgcttacg     60
cagcttgcgc aggtgggagg cgaggcgcac ccgcagctcc tcggtgctct ggccgagcat    120
ggcctgcacc tcgccgcggt actgcaccag gcggccgcac acgtcctcca tgtccgcgc      179

<210> SEQ ID NO 86
<211> LENGTH: 70
<212> TYPE: DNA
<213> ORGANISM: Artificial Sequence
<220> FEATURE:
<223> OTHER INFORMATION: Synthetic oligonucleotide (Primary Indication:
      Hemophilia A; Target: F8)

<400> SEQUENCE: 86
accgaagctg gtacctcaca gagaatatac aacgctttct ccccaatcca gctggagtgc     60
agcttgagga                                                            70

<210> SEQ ID NO 87
<211> LENGTH: 70
<212> TYPE: DNA
<213> ORGANISM: Artificial Sequence
<220> FEATURE:
<223> OTHER INFORMATION: Synthetic oligonucleotide (Primary Indication:
      Hemophilia A; Target: F8)

<400> SEQUENCE: 87
tcctcaagct gcactccagc tggattgggg agaaagcgtt gtatattctc tgtgaggtac     60
cagcttcggt                                                            70

<210> SEQ ID NO 88
<211> LENGTH: 40
<212> TYPE: DNA
<213> ORGANISM: Artificial Sequence
<220> FEATURE:
<223> OTHER INFORMATION: Synthetic oligonucleotide (Primary Indication:
      Hemophilia A; Target: F8)

<400> SEQUENCE: 88
acctcacaga gaatatacaa cgctttctcc ccaatccagc                           40

<210> SEQ ID NO 89
<211> LENGTH: 40
<212> TYPE: DNA
<213> ORGANISM: Artificial Sequence
<220> FEATURE:
<223> OTHER INFORMATION: Synthetic oligonucleotide (Primary Indication:
      Hemophilia A; Target: F8)

<400> SEQUENCE: 89
gctggattgg ggagaaagcg ttgtatattc tctgtgaggt                           40

<210> SEQ ID NO 90
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Hemophilia B; Target: F9)

<400> SEQUENCE: 90
agttcttcag taccttagag ttccacttgt tgaccgagcc acatgtcttc gatctacaaa     60
gttcaccatc t                                                          71

<210> SEQ ID NO 91
<211> LENGTH: 71
<212> TYPE: DNA
<213> ORGANISM: Artificial Sequence
<220> FEATURE:

```
<223> OTHER INFORMATION: Synthetic oligonucleotide (Primary Indication:
      Hemophilia B; Target: F9)

<400> SEQUENCE: 91
agatggtgaa ctttgtagat cgaagacatg tggctcggtc aacaagtgga actctaaggt    60
actgaagaac t                                                         71

<210> SEQ ID NO 92
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      Hemophilia B; Target: F9)

<400> SEQUENCE: 92
tagagttcca cttgttgacc gagccacatg tcttcgatct a                        41

<210> SEQ ID NO 93
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      Hemophilia B; Target: F9)

<400> SEQUENCE: 93
tagatcgaag acatgtggct cggtcaacaa gtggaactct a                        41

<210> SEQ ID NO 94
<211> LENGTH: 72
<212> TYPE: DNA
<213> ORGANISM: Artificial Sequence
<220> FEATURE:
<223> OTHER INFORMATION: Synthetic oligonucleotide (Primary Indication:
      Sickle cell anemia; Target: HBB)

<400> SEQUENCE: 94
aacctcaaac agacaccatg gtgcatctga ctcctgagga gaagtctgcc gttactgccc    60
tgtggggcaa gg                                                        72

<210> SEQ ID NO 95
<211> LENGTH: 72
<212> TYPE: DNA
<213> ORGANISM: Artificial Sequence
<220> FEATURE:
<223> OTHER INFORMATION: Synthetic oligonucleotide (Primary Indication:
      Sickle cell anemia; Target: HBB)

<400> SEQUENCE: 95
ccttgcccca cagggcagta acggcagact tctcctcagg agtcagatgc accatggtgt    60
ctgtttgagg tt                                                        72

<210> SEQ ID NO 96
<211> LENGTH: 40
<212> TYPE: DNA
<213> ORGANISM: Artificial Sequence
<220> FEATURE:
<223> OTHER INFORMATION: Synthetic oligonucleotide (Primary Indication:
      Sickle cell anemia; Target: HBB)

<400> SEQUENCE: 96
catggtgcat ctgactcctg aggagaagtc tgccgttact                          40
```

```
<210> SEQ ID NO 97
<211> LENGTH: 40
<212> TYPE: DNA
<213> ORGANISM: Artificial Sequence
<220> FEATURE:
<223> OTHER INFORMATION: Synthetic oligonucleotide (Primary Indication:
      Sickle cell anemia; Target: HBB)

<400> SEQUENCE: 97
agtaacggca gacttctcct caggagtcag atgcaccatg                             40

<210> SEQ ID NO 98
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      TTR Amyloidosis; Target: TTR)

<400> SEQUENCE: 98
atgctgtccg aggcagtcct gccatcaatg tggccgtgca tgtgttcaga aaggctgctg       60
atgacacctg g                                                           71

<210> SEQ ID NO 99
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      TTR Amyloidosis; Target: TTR)

<400> SEQUENCE: 99
ccaggtgtca tcagcagcct ttctgaacac atgcacggcc acattgatgg caggactgcc       60
tcggacagca t                                                           71

<210> SEQ ID NO 100
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      TTR Amyloidosis; Target: TTR)

<400> SEQUENCE: 100
gtcctgccat caatgtggcc gtgcatgtgt tcagaaaggc t                           41

<210> SEQ ID NO 101
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      TTR Amyloidosis; Target: TTR)

<400> SEQUENCE: 101
agcctttctg aacacatgca cggccacatt gatggcagga c                           41

<210> SEQ ID NO 102
<211> LENGTH: 40
<212> TYPE: DNA
<213> ORGANISM: Artificial Sequence
<220> FEATURE:
<223> OTHER INFORMATION: Synthetic oligonucleotide (Primary Indication:
      Duchenne Musc. Dys.; Target: Dystrophin)

<400> SEQUENCE: 102
```
caaaaaccca aaatattttg gctcctactc agactgttac                          40

<210> SEQ ID NO 103
<211> LENGTH: 40
<212> TYPE: DNA
<213> ORGANISM: Artificial Sequence
<220> FEATURE:
<223> OTHER INFORMATION: Synthetic oligonucleotide (Primary Indication:
      Duchenne Musc. Dys.; Target: Dystrophin)

<400> SEQUENCE: 103
gtaacagtct gagtaggagc caaaatattt tgggtttttg                          40

<210> SEQ ID NO 104
<211> LENGTH: 70
<212> TYPE: DNA
<213> ORGANISM: Artificial Sequence
<220> FEATURE:
<223> OTHER INFORMATION: Synthetic oligonucleotide (Primary Indication:
      Duchenne Musc. Dys.; Target: Dystrophin)

<400> SEQUENCE: 104
cttttttcct ttttgcaaaa acccaaaata ttttggctcc tactcagact gttactctgg   60
tgacacaacc                                                          70

<210> SEQ ID NO 105
<211> LENGTH: 70
<212> TYPE: DNA
<213> ORGANISM: Artificial Sequence
<220> FEATURE:
<223> OTHER INFORMATION: Synthetic oligonucleotide (Primary Indication:
      Duchenne Musc. Dys.; Target: Dystrophin)

<400> SEQUENCE: 105
ggttgtgtca ccagagtaac agtctgagta ggagccaaaa tatttgggt ttttgcaaaa    60 aggaaaaaag                                                          70

<210> SEQ ID NO 106
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Cystic Fibrosis; Target: CFTR)

<400> SEQUENCE: 106
ggattatgcc tggcaccatt aaagaaaata tcatctttgg tgtttcctat gatgaatata   60
gatacagaag c                                                        71

<210> SEQ ID NO 107
<211> LENGTH: 71
<212> TYPE: DNA
<213> ORGANISM: Artificial Sequence
<220> FEATURE:
<223> OTHER INFORMATION: Synthetic oligonucleotide (Primary Indication:
      Cystic Fibrosis; Target: CFTR)

<400> SEQUENCE: 107
gcttctgtat ctatattcat cataggaaac accaaagatg atattttctt taatggtgcc   60
aggcataatc c                                                        71

<210> SEQ ID NO 108
<211> LENGTH: 41
<212> TYPE: DNA

```
<213> ORGANISM: Artificial Sequence
<220> FEATURE:
<223> OTHER INFORMATION: Synthetic oligonucleotide (Primary Indication:
      Cystic Fibrosis; Target: CFTR)

<400> SEQUENCE: 108
ccattaaaga aaatatcatc tttggtgttt cctatgatga a                          41

<210> SEQ ID NO 109
<211> LENGTH: 41
<212> TYPE: DNA
<213> ORGANISM: Artificial Sequence
<220> FEATURE:
<223> OTHER INFORMATION: Synthetic oligonucleotide (Primary Indication:
      Cystic Fibrosis; Target: CFTR)

<400> SEQUENCE: 109
ttcatcatag gaaacaccaa agatgatatt ttctttaatg g                          41

<210> SEQ ID NO 110
<211> LENGTH: 61
<212> TYPE: DNA
<213> ORGANISM: Artificial Sequence
<220> FEATURE:
<223> OTHER INFORMATION: Synthetic oligonucleotide (Primary Indication:
      Cystic Fibrosis; Target: CFTR)

<400> SEQUENCE: 110
ttctgtatct atattcatca taggaaacac caaagataat gttctcctta atggtgccag       60
g                                                                      61
```

COMPOSITIONS AND METHODS FOR EDITING NUCLEIC ACIDS IN CELLS UTILIZING OLIGONUCLEOTIDES

CROSS-REFERENCE TO RELATED APPLICATIONS

The following application claims priority to PCT patent application serial no.: PCT/US2015/65348 filed 11 Dec. 2015 and to provisional patent application Ser. Nos. 62/252,693 filed 9 Nov. 2015, 62/180,175 filed 16 Jun. 2015, 62/141,077 filed 31 Mar. 2015 and 62/091,027 filed 12 Dec. 2014.

STATEMENT REGARDING FEDERALLY SPONSORED RESEARCH OR DEVELOPMENT

Not applicable

THE NAMES OF THE PARTIES TO A JOINT RESEARCH AGREEMENT

Not applicable

INCORPORATION-BY-REFERENCE OF MATERIAL SUBMITTED ON A COMPACT DISC

Not applicable

TECHNICAL FIELD

The present invention relates to the use of oligonucleotides that modify the sequence of a genome or RNA for applications in the areas of human and animal therapeutics (including in vivo and ex vivo therapeutic applications), cosmetic procedures, pre-clinical development, basic research, and for agriculture to improve food stocks, animal husbandry for modifying animal breeds (farm and other domesticated animals) to impart desirable features, and energy production.

BACKGROUND OF THE INVENTION

Advances in oligonucleotide chemistry and in vivo nucleic acid delivery technologies over the past decade have unlocked the potential for DNA and RNA modifying therapies. Positive data in numerous clinical trials and the approval of the first systemic antisense drug in the United States, Mipomersen (Isis Pharmaceuticals, San Diego, CA) have further demonstrated the clinical utility of oligonucleotide drugs.

While the clinical benefits of using therapeutic oligonucleotides to inhibit protein expression by modulation of RNA levels have been demonstrated, the clinical potential of nucleic acid editing or repair approaches will likely exceed that of these inhibition approaches (T. M. Woolf, et al., PNAS Vol. 92:8298-8302, 1995, and T. M. Woolf, Nat. Biotech Vol. 16:341-344, 1998). A robust editing technology platform enables site-specific chemical correction of mutated DNA, the creation of protective alleles or otherwise creating changes in the genome of whole organisms, cells or tissues that are desirable for research, therapeutic, cosmetic or agricultural purposes. Such a platform will have broad utility as a therapeutic intervention and potential cure for a wide range of diseases caused by genetic point mutations, and other genetic lesions.

There are two general mechanisms of sequence editing with nucleic acids. These are chemical modification and incorporation of nucleic acid sequences into the target. With the chemical modification mechanism, the editing oligonucleotide causes a chemical modification of the targeted nucleotide, such that the coding of the targeted nucleotide is changed. The second general mechanism is by incorporation of one or more oligonucleotides into the target RNA or DNA sequence. In this mechanism, the oligonucleotide is often referred to as "donor" DNA. This mechanism is loosely referred to as homologous recombination (HR) or homology directed repair, but can also include other mechanisms such as gene conversion, trans-splicing or strand-invasion followed by priming of nucleic acid synthesis.

The explosion of information on genetic and molecular pathways, driven by Next Generation Sequencing and SNP analysis, has provided a vast array of targets for therapeutic editing to treat monogenic and polygenic diseases. Examples of these diseases include familial Alzheimer's disease, high blood pressure, high cholesterol, HIV (by inducing CCR5 mutations), sickle cell anemia, obesity, diabetes, some forms of muscular dystrophy and many inborn errors of metabolism. The therapeutic potential of DNA editing repair has been demonstrated by promising data. Engineered zinc finger nucleases (Sangamo Biosciences, Inc., Richmond, CA) have been used to treat HIV and exon skipping antisense morpholinos (Sarepta Therapeutics, Inc., Cambridge, MA) and 2'-O-methyl phosphorothioate oligonucleotides (Prosensa, Leiden, The Netherlands) have been used to treat certain forms of Duchenne Muscular Dystrophy. In addition, the CRISPR/Cas-9 gene editing approach to enhancing editing efficiency has spawned a number of research products and investments in therapeutic applications.

Therapeutic mRNA editing was first demonstrated in a vertebrate model system by Woolf et al. (PNAS Vol. 92:8298-8302, 1995). In this system, a targeted stop codon mutation in a Duchenne Muscular Dystrophy mRNA was modified by duplex formation with an editing antisense RNA at the target site. The work by Woolf et al. induced editing that was limited in specificity.

Montiel et al., (PNAS 110(45):18285-90, 2013) demonstrated a related mechanism of mRNA repair for Cystic Fibrosis wherein a 20% correction was achieved in mammalian cells. While this successfully demonstrated the principle of therapeutic editing, Montiel's methods are not easily applied for clinical use. The primary reason for this is that the method of Montiel et al. require the introduction of a modified gene, mRNA or proteins into cells by gene therapy, mRNA therapy or other methods. Because of this all of the known disadvantages recognized with gene therapy and mRNA therapy are also relevant to Montiel's method of therapeutic editing.

In another approach, Singer, et al. (Nucleic Acids Research, 27(24):38-45, 1999) targeted DNA with an alkylating oligomer that hybridized to the target strand assisted by RecA protein. In this study, reactive nitrogen mustard groups were conjugated to the 5-position of an internal dU residue of the invading oligonucleotide via an amino-propyl linker. Up to 50% of the oligonucleotide was observed to crosslink with the target DNA sequence and up to 2% mutation of the target sequence was confirmed upon transfection of the complex into mammalian cells following one treatment cycle. However, cross-linking the invading oligonucleotide to the targeted DNA typically results in a variety of mutations distributed over a region of DNA and can result in inhibition of replication. Conjugation of reactive base modifying chemistries to oligonucleotides and sequence specific modification of targeted dsDNA sequences has been achieved (F. Nagatsugi, et al. Nucleic Acids Research, Vol. 31(6):e31 DOI: 10.1093/nar/gng031, 2003). In this study, a 2-amino-6-vinylpurine nucleoside analog was synthetically incorporated into triplex-forming oligonucleotide (TFO). This TFO reacted with a target DNA plasmid in buffers achieving up to 25-40% modification of the target DNA sequence. This mixture of cross-linked TFO and DNA target was then transfected into cells and the level of mutagenesis was determined. This study demonstrated site-specific mutation of the targeted sequence with some specificity for the targeted base and a significant albeit low efficiency (0.3% with one treatment). However, this method has the same disadvantages as Singer, et al. because it results in cross-linking.

Sasaki et al. (J. Am. Chem. Soc., 126(29):8864-8865, 2004; see also U.S. Pat. No. 7,495,095) developed a method for delivery of nitric oxide (NO) to a specific cytosine site of DNA sequence followed by specific deamination of the cytosine base. In this method, nitrosation of the 6-thio-guanosine-containing oligodeoxynucleotides (ODN) was performed with S-nitroso-N-acetylpenicillamine. The resulting S-nitroso thioguanine was then used to perform an interstrand NO transfer reaction followed by deamination at the target site. A 42% transformation ratio from dmC to dT was observed while NO transfer reaction (and deamination) was not observed with complementary ODN having mismatched dT, dA, or dG at the target site. This technique required non-physiological pH to allow the reaction to occur, and long incubation times, that would not necessarily be applicable to therapeutic intervention. In addition, the chemically reactive oligonucleotide strategies, even if made efficient in cells, require complex chemical synthesis, and may be reactive with non-targeted cellular components, including DNA, which is not ideal. They also require different targeted chemistries for each base change, and are only suitable for transitions, not transversions, which limits their general utility. Further, this method does not repair deletions and insertions, which is a further limitation to their general application to correcting any mutation. Nevertheless, this chemical modification approach to editing has the advantage that it does not require the addition of exogenous proteins to the cell in order to facilitate editing, and it can in principle be used with highly modified oligonucleotide backbones that can allow for better tissue distribution and cellular uptake.

One research group achieved editing with chimeric oligonucleotide constructs in the 1990's and then with single-stranded oligonucleotide constructs in the 2000's (Brachman and Kmiec, DNA Repair 4:445-457, 2005). In this editing approach, the desired edited sequence was contained in the editing oligonucleotide, and this sequence replaced the existing sequence in the genome (FIG. 1). The efficiency of editing reported in the 1990's with chimeric oligonucleotide constructs was variable, and this approach was not brought successfully to clinical application despite significant investment. Follow-on work conducted by the same research group with single-stranded editing oligonucleotides led to consistent reproducible editing, but with relatively low efficiencies (~0.1-1%). The most active single-stranded editing oligonucleotides had unmodified DNA internal regions, which resulted in rapid nuclease degradation in cells and likely resulted in Toll-like receptor activation. Editing efficiency was increased by the following approaches:

1. adding three phosphorothioate residues to each end of the editing oligonucleotides (However, the resulting editing oligonucleotides where still susceptible to rapid endonuclease digestion within the cell and the phosphorothioates increase their toxicity);
2. synchronizing the cell cycle such that the cells are treated with the editing oligonucleotides during the S-Phase. Unfortunately while this increased editing efficiency to some degree, the approach is cumbersome and not always practical for in vivo therapeutics; and
3. treating the cell with reagents that slow the progression of the replication forks and/or induce DNA strand-cleavage in the cell, which results in increased DNA repair in the cell (However while this increased editing efficiency to some degree, the approach is also cumbersome and not always practical for in vivo therapeutics.
4. Adding PNA clamps or strand invading single-stranded PNAs that bind in the vicinity of the targeted editing (Bakal et al. Current Gene Therapy Vol. 14(5):331-42 (2014), Chin et al. PNAS Vol 105(36):13514-13519 (2008), Rogers et al. PNAS Vol. 99(26):16695-16700 (2002), U.S. Pat. No. 8,309,356.

These improvements increased editing efficiency to up to approximately 5% in model in vitro cellular systems, but each approach had limitations as cited above (Kmiec, Surgical Oncology 24:95-99, 2015).

More recently the CRISPR-Cas9 system has been used to enhance the efficiency of editing genomes. However, the CRISPR-Cas9 system often times causes off-target modifications and requires potentially dangerous and undesirable single and double-stranded breaks in the chromosome. This system also strictly requires that a foreign bacterial protein be expressed or delivered in functional form to cells. The bacterial protein, Cas9, is immunogenic and therefore less desirable for therapeutic applications. In addition, expression or delivery of a protein to a cell is a substantial challenge for clinical development. In order to make a specific change of one sequence to another defined sequence, the CRISPR-Cas9 system requires, in addition to Cas9, a gRNA exceeding 70 nucleotides and one or two additional oligonucleotides for insertion in the genome. Thus, the CRISPR/Cas9 system of editing is highly complex, and this complexity creates a challenge for clinical development.

Consequently, there is a need in the biomedical and biotechnology industry for nucleic acid editing compounds that work more efficiently in general and particularly with shorter editing oligonucleotides and do not strictly require: cross-linking the editing oligonucleotide to the nucleobase of the targeted nucleic acid as a method of action; the introduction of breaks in the target nucleic acid to effect a repair; delivery vehicles; the delivery of immunogenic proteins or unmodified unstable RNA into the cell; and the introduction of vector sequences into the target nucleic acid and/or cell. In addition, it is desirable that these nucleic acid editing compounds are able to repair most point mutations as well as small insertions and deletions, contain chemical modifications that enhance the pharmacokinetics, have biodistribution and intra-cellular nuclease stability without substantially reducing the editing activity, optionally reduce the activation of Toll-like receptors, and correct the underlying genetic causes of disease by editing a targeted DNA sequence and in some embodiments RNA sequence.

SUMMARY OF THE INVENTION

One aspect of this invention is a method of utilizing a single-stranded oligonucleotide complementary to one of the DNA strands of a genome or an RNA for sequence editing. The method comprises the steps of introducing into a cell or an organism a single-stranded oligonucleotide without strictly requiring exogenous proteins or nucleic acids to assist in editing said genomic sequence. In certain embodiments, the oligonucleotide is substantially complementary to the target sequence, with the exception of one or more mismatches, including inserts or deletions, relative to the target sequence. Such an oligonucleotide may be referred to herein as an oligonucleotide, an oligonucleotide of the invention, or as an editing oligonucleotide. In certain embodiments, the oligonucleotide is substantially complementary to the target sequence in the genome, and comprises one or more chemical modifications that react with, or promote a reaction with, a nucleotide on the target sequence. Examples of such reactions include alkylation, acetylation, cross-linking, amination, de-amination, generation of a free (non-covalently bound) reactive compound. An example of such a chemical modification is a nitrosamine. Such an oligonucleotide may also be referred to herein as an oligonucleotide, a oligonucleotide of the invention, or as an editing oligonucleotide. The oligonucleotide can preferably have one or more chemical modifications. This/these chemical modification(s) modification(s) may include one or more backbone modification(s), sugar modification(s) and/or nucleobase modification(s) The oligonucleotide is complementary to a target sequence in the genome and may have mismatches, as described below. Modifications may increase the efficiency of editing by increasing the nuclease stability as compared to unmodified oligonucleotides or compared to oligonucleotides having three phosphorothioates on each terminus.

The desired edit may be a transition or transversion, or a deletion or insertion. In one embodiment the editing oligonucleotide sequence is the sequence desired after the editing is completed. Without wishing to be bound by a particular theory or mechanism, the editing oligonucleotide binds to the partially complementary target genomic DNA sequence when the target sequence is separated from the opposite genomic strand during cellular processes such as transcription or replication. In some cases, the hybridization of the editing oligonucleotide to a double-stranded genomic DNA target can occur during "breathing" or transient melting of the target DNA. Once the heteroduplex is formed between the editing oligonucleotide and target genomic DNA strand, the area of non-perfect complementarity is corrected by cellular DNA repair.

When the editing oligonucleotide is used as the "correct" template for repair, the desired edit will be incorporated into the targeted genomic DNA strand or RNA strand. In a second mechanism that can also occur in the cell, the editing oligonucleotide is incorporated into the target nucleic acid such as into DNA by Homologous Recombination (HR), or other processes that result in the editing oligonucleotide sequence being incorporated into the target DNA or RNA.

Another aspect of the invention provides for editing oligonucleotides that cause a site-specific chemical modification of the targeted nucleotide, such that the coding of the targeted nucleotide is changed. These editing oligonucleotides may comprise the structures:

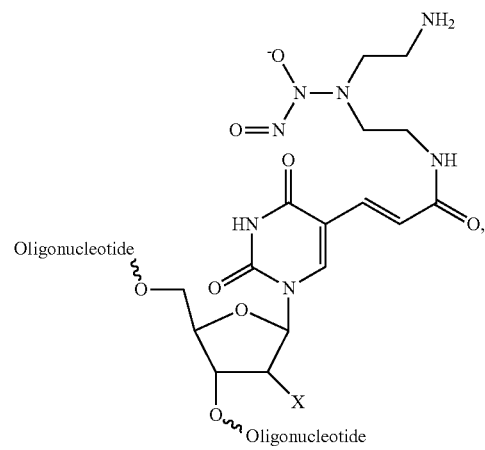

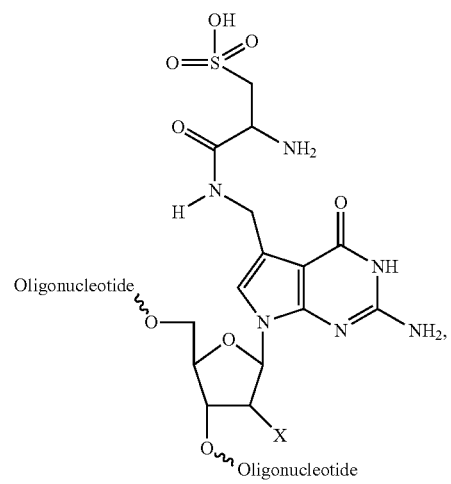

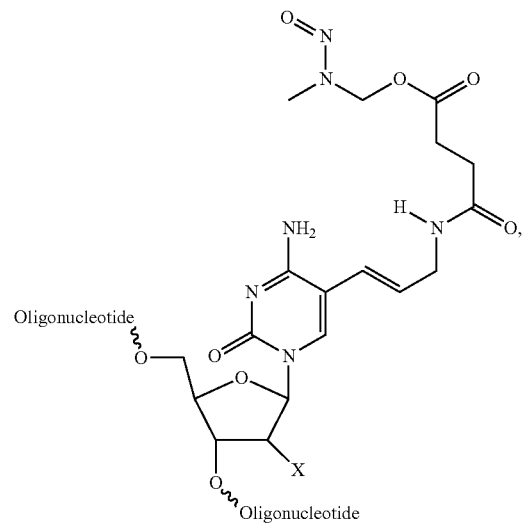

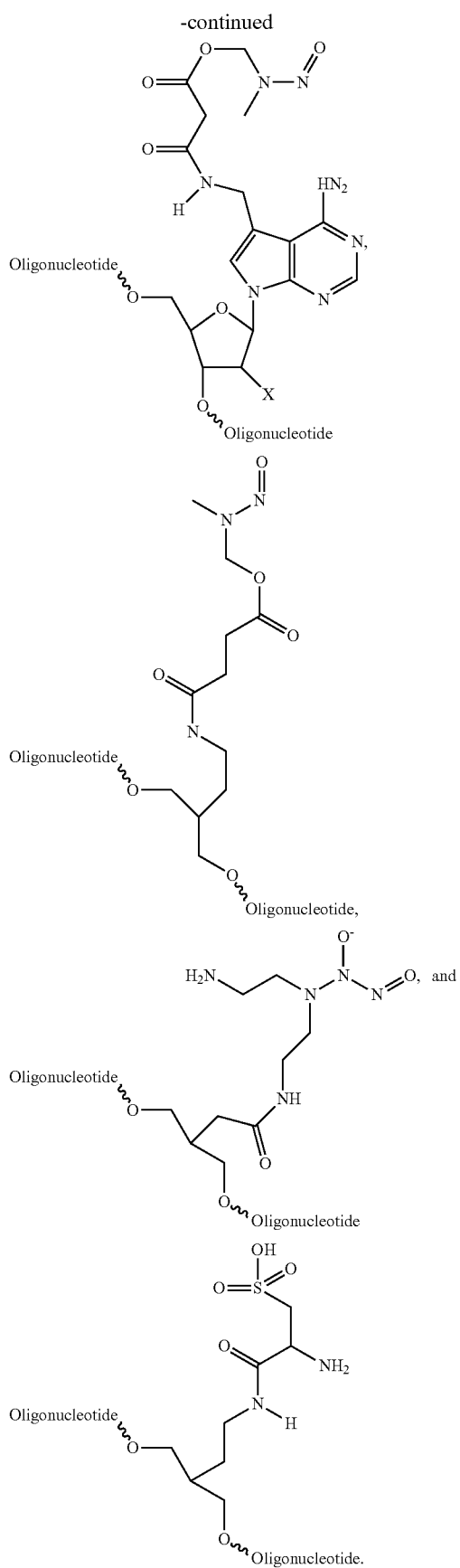

wherein each oligonucleotide is substantially complementary to said target nucleic acid and is about 10 to about 50 or 10 to about 200 nucleotides; X is H, OH, halogen, $R^1$, $SR^1$ or $OR^1$; halogen is Cl, F, Br or I; and $R^1$ is —$CH_3$, —$CH_2CH_3$ or —$CH_2OCH_3$. The targeted nucleic acid may be RNA or DNA. When the target is RNA it is preferably mRNA.

In one embodiment, each oligonucleotide of the editing oligonucleotide comprises at least one of the following internucleotide linkages or sugar modifications a phosphodieater, a phosphotriester (alkyl, aryl, heteroalkyl, heteroaryl), a methylphosphonate, a boranophosphate, a morpholino, a non-bridging dialkylphosphoramidate, a bridging 3'-NH— or 5'-NH—, a bridging 3'-S— or 5'-S— or 2'-modified sugar, or other modifications listed in FIGS. 20 and 22.

Other embodiments include, a pharmaceutical composition comprising a pharmaceutical carrier or delivery vehicle and one or more of the editing oligonucleotides wherein the carrier may be water, saline or physiological buffered saline and a cell containing one or more of the editing oligonucleotide.

Another aspect of the present invention is a method of improving the health of an individual requiring treatment for a medical condition or reducing or eliminating or preventing a medical condition in an individual requiring treatment for the condition comprising administering a composition containing at least one editing oligonucleotide to the individual. Administration may be intramuscular injection, intravitreal, intraperitoneal injection, subcutaneous injection intravenous injection, transdermal delivery, aerosol inhalation, rectal suppository or vaginal suppository. Medical conditions that may be treated include, for example, adenosine deaminase deficiency, alpha-1 antitrypsin deficiency, Alzheimer's disease, amyloid diseases, Becker muscular dystrophy, breast cancer predisposition mutations, Canavan disease, Charcot-Marie-Tooth disease, cystic fibrosis, Type 1 diabetes, Type 2 diabetes, Duchenne muscular dystrophy, Fabry disease, hereditary tyrosinemia type I (HTI), familial adenomatous polyposis, familial amyloid cardiomyopathy, familial amyloid polyneuropathy, familial dysautonomia, familial hypercholesterolemia, Friedreich's ataxia, Gaucher disease type I, Gaucher disease II, glycogen storage disease type II, GM2 gangliosidosis, hemochromatosis, hemophilia A, hemophilia B, hemophilia C, hexosaminidase A deficiency, ovarian cancer predisposition mutations, obesity, phenylketonuria, polycystic kidney disease, prion disease, senile systemic amyloidosis, sickle-cell disease, Smith-Lemli-Opitz syndrome, spinal muscular atrophy, Wilson's disease and hereditary blindness. Other diseases include those point mutations or small deletions or insertions or diseases that can be corrected by point changes or small deletions or insertions listed at the World Wide Web at omim.org/Online Mendelian Inheritance in Man® An Online Catalog of Human Genes and Genetic Disorders Updated 2 Mar. 2015, including targets listed in FIG. 23.

Other aspects of the present invention include methods of administering at least one editing oligonucleotide to an individual suspected of having a condition that may be treated by such administration, wherein that condition may be reduced, prevented or eliminated by reverting a mutated nucleotide in a target nucleic acid to the wild-type nucleotide; modifying a non-mutated nucleotide of a mutated codon in a target nucleic acid to produce a wild-type codon; converting a pre-mature stop codon in a target nucleic acid to a read through non-wild type codon; or modifying a mutated codon in a target nucleic acid to produce a non-wild type codon that results in a non-disease causing amino acid, also editing which inserts or deletes a number of nucleotides (e.g., in some cases, less than about 10, less than about 5 or less than about 3). In these methods the condition or medical condition that may be treated with the editing oligonucleotides include for example, beta thalassemia, cystic fibrosis, Duchenne muscular dystrophy and Hurler syndrome.

Another aspect of the present invention is a method for modifying the nucleic acid coding for a protein or a functional RNA or regulating the transcription levels of a gene to modulate said protein's or RNA's activity or modifying a mutant protein to suppress its disease causing affects comprising the steps of administering to a cell or to an individual at least one editing oligonucleotide. In these methods the target nucleic acid for editing is DNA.

The editing oligonucleotides of the present invention may perform one or more of the following functions, which include: exact reversion of a mutated base to a base with the coding specificity of the wild-type DNA or RNA sequence; change a mutated codon to encode a non-wild-type that results in a non-disease causing amino acid; modification of a stop codon, to a read through codon of a non-wild-type, codon that still allows for the activity or partial activity of the targeted protein; change a non-mutated base of a mutated codon, that results in the wild-type codon or non-disease amino acid codon; change the nucleic acid sequence of a protein, to increase or decrease (or eliminate) the activity of a domain of that protein; change a sequence of RNA or DNA, to produce an allele that is known to be protective of a disease; change a site in the targeted mutant protein, other than the mutated or disease variant codon, that suppresses the disease causing effects of the mutated gene; change a site in a gene or RNA other than the mutated or disease variant, that suppresses the disease causing effects of the mutated gene ($2^{nd}$ site suppressors); change a promotor, enhancer or silencing region of a gene, that modulates the expression of the disease associated gene such that the diseased state is reduced (up or down regulation or modulation of the response of the gene's expression to changes in the environment); methylation of sugar in DNA, to change the epigenetic state of the targeted sequence and/or change a splice-site sequence at the DNA or RNA level to affect a splicing pattern that treats the disease state.

Other embodiments include editing oligonucleotides with reversible charge neutralizing phosphotriester backbone modifications. These modifications have the advantage of imparting improved delivery and nuclease stability to the oligonucleotide as it travels to the target cell's cytoplasm. This may be preferred in central editing region, when the editing oligonucleotide uses mismatch repair and particularly when using self-delivering editing oligonucleotides. Self-delivering oligonucleotides refer to chemistries that efficiently enter the interior of the cell without delivery vehicles, such as Gal-NAC conjugated oligonucleotide, lipophilic group conjugated editing oligonucleotide (U.S. Patent Application 20120065243 A1), or oligonucleotides with phosphorothioate tails or otherwise having about 8 or more phosphorothioate linkages (U.S. Patent Application 20120065243 A1). that must survive the nuclease rich endo-lysosomal pathway]. Once in the target cell cytoplasm, the modifications are removed by cellular esterases, liberating an editing oligonucleotide with a natural or more natural structure that is better recognized by the cellular homologous recombination and mismatch repair machinery.

BRIEF DESCRIPTION OF THE DRAWINGS

FIG. 10: Conjugation of 2,2,2-trifluoro-N-(2,2,5-trioxooxathiolan-4-yl)acetamide to an oligonucleotide with primary amino group.

FIG. 13: Conjugation of NHS ester of 4-{[methyl(nitroso)amino]methoxy}-4-oxo-butanoic acid to the oligonucleotide with primary amino group.

FIG. 20: Exemplary listing of backbone modifications

FIG. 21: Exemplary listing of nucleobase modifications

FIG. 22: Exemplary listing of sugar modifications

FIG. 23: Exemplary listing of diseases and disorders that can be treated with the oligonucleotides of the invention.

FIG. 24: Exemplary listing of editing oligonucleotides targeting genes associated with representative diseases and disorders. The amino acid positions are numbered from the start of the signal peptide or the start of the mature protein, as is clear from comparison to the target sequences. The "Primary Result of Edit" is the resulting amino acid encoded after a successful edit of the common target mutation or other desired edit. An editing site is indicated by lower case sequence, when noted. The "strand" is relative to the transcribed sequence as sense.

DETAILED DESCRIPTION

Figure 1:
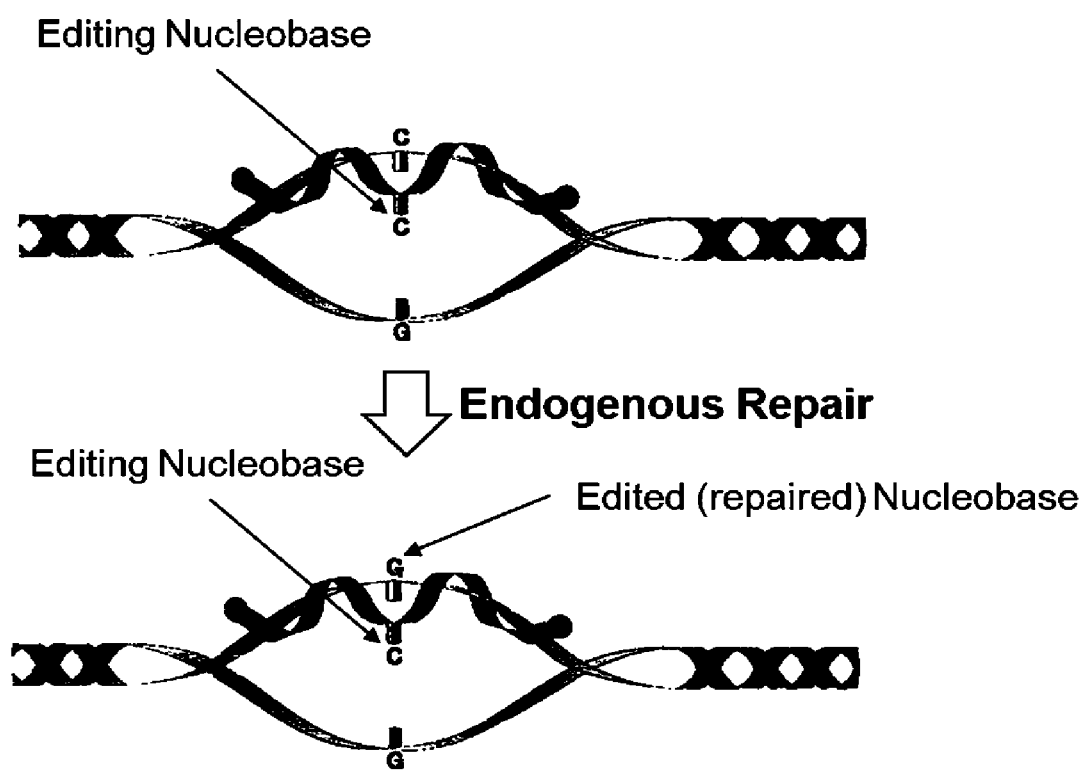
FIG. 1: is a schematic of an editing mechanism previously described by Brachman, Erin E. and Eric B. Kmiec.

Unless defined otherwise, all terms used herein have the same meaning as are commonly understood by one of skill in the art to which this invention belongs. All patents, patent applications, website postings and publications referred to throughout the disclosure herein are incorporated by reference in their entirety. In the event that there is a plurality of definitions for a term herein, those in this section prevail.

As used herein, the letters "G," "C," "A", "T" and "U" each generally stand for a nucleotide that contains guanine, cytosine, adenine, thymine and uracil as a base, respectively. However, it will be understood that the term "nucleotide" can also refer to a modified nucleotide, as further detailed below. In a sequence it is understood that a "T" refers to a "U" if the chemistry employed is RNA or modified RNA. Likewise, in a sequence, "U" is understood to be "T" in DNA or modified DNA. The skilled person is well aware that guanine, cytosine, adenine, thymine and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Also, for example, 5-methyl C can exist in the target site DNA or in the editing oligonucleotide in place of C.

The term "oligonucleotide" as used herein refers to a polymeric form of nucleotides, either ribonucleotides (RNA), deoxyribonucleotides (DNA) or other substitutes such as peptide nucleic acids (PNA), which is a polymeric form of nucleobases, incorporating natural and non-natural nucleotides of a length ranging from at least 8, or generally about 5 to about 200 or up to 500 when made chemically, or more commonly to about 100 that can be obtained commercially from many sources, including TriLink Biotechnologies (San Diego, CA), Exiqon (Woburn, MA) and made with methods known in the art (Oligonucleotide Synthesis: Methods and Applications, In Methods in Molecular Biology Volume 288 (2005) Piet Herdewijn (Editor) ISBN: 1588292339 Springer-Verlag New York, LLC)c, or for longer oligonucleotides, Integrated DNA Technologies (Coralville, Iowa). In cases when specialized synthesis methods are employed, such as when non-chemically synthesized sources of single-stranded DNA are employed, such as single-stranded vector DNA, or reverse transcribed cDNA from in vitro transcribed plasmid mRNA, the single-stranded editing "oligonucleotide" or donor DNA can be up to 2,000 nucleotides. Thus, this term includes double- and single-stranded DNA and single-stranded RNA. In addition, oligonucleotides may be nuclease resistant and include but are not limited to 2'-O-methyl ribonucleotides, constrained or Locked Nucleic Acids (LNAs), 2' fluoro, phosphorothioate nucleotides (including chirally enriched phosphorothioate nucleotides), phosphorodithioate nucleotides, phosphoramidate nucleotides, and methylphosphonate nucleotides (include chirally enriched methyphosphonates). The oligonucleotides may also contain non-natural internucleosidyl linkages such as those in PNA or morpholino nucleic acids (MNA). The above definition when included in the phrase "editing oligonucleotides" refers to an oligonucleotide that may further comprise one or more chemical modifications that react with, or promote a reaction with, a nucleotide on the target sequence (e.g., a nitrosamine).

The term "nucleic acid" as used herein refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include nucleic acids with 2'-modified sugars, DNA, RNA, chimeric DNA-RNA polymers or analogs thereof. In a nucleic acid, the backbone may be made up of a variety of linkages, including one or more of sugar-phosphodiester linkages, peptide-nucleic acid (PNA) linkages (PCT application no. WO 95/32305), phosphorothioate linkages or combinations thereof. Sugar moieties in a nucleic acid may be ribose, deoxyribose, or similar compounds with substitutions, e.g., 2' methoxy and 2' halide (e.g., 2'-F), LNA (or other conformationally restrained modified oligonucleotides) and UNA (unlinked nucleic acid) substitutions.

The term, "2'-modified sugar" as used herein regarding nucleic acids refers to 2'F, 2' amino, 2'-O—X (where X is a modification known in the art to result in a hybridization capable oligonucleotide, including, but not limited to an alkyl group (e.g., methyl, ethyl or propyl) or a substituted alkyl group such as methoxyethoxy or a group that bridges the 2' ribose to the 4' ribose position (i.e., often referred to as constrained nucleotides) including but not limited to LNAs and cET-BNAs, a bridging 3'-$CH_2$— or 5'-$CH_2$—, a bridging 3'-amide (—C(O)—NH—) or 5'-amide (—C(O)—NH—) or any combination thereof.

The term, "target sequence" as used herein refers to a contiguous portion of the nucleotide sequence of a DNA sequence in a cell or RNA sequence in a cell that is to be modified by the editing oligonucleotide.

The term "complementary," when used to describe a first nucleotide sequence in relation to a second nucleotide sequence (e.g. the editing oligonucleotide and the target nucleic acid), refers to the ability of an oligonucleotide or polynucleotide comprising the first nucleotide sequence to hybridize and form a duplex (or triplex) structure under certain conditions with an oligonucleotide or polynucleotide comprising the second nucleotide sequence, as will be understood by the skilled person. A preferred condition is physiologically relevant conditions as may be encountered inside an organism, can apply. The skilled person will be able to determine the set of conditions most appropriate for a test of complementarity of two sequences in accordance with the ultimate application of the hybridized nucleotides.

Hybridization includes base-pairing of the oligonucleotide or polynucleotide comprising the first nucleotide sequence to the oligonucleotide or polynucleotide comprising the second nucleotide sequence over the entire length of the first and second nucleotide sequence. Such sequences can be referred to as "fully complementary" with respect to each other herein, but in some case with an editing oligonucleotide of this invention, at least one base is different from the complementary base of the target sequence.

The term "substantially complementary", as used herein, refers to the relationship between an oligonucleotide of the invention and a target genomic sequence, wherein a sufficient percentage of nucleotides of the oligonucleotide are paired with nucleotides of the target sequence to promote hybridization. In some embodiments, the percentage is greater than 99, greater than 95, or greater than 90 percent. In some embodiments, the percentage is greater than 80, greater than 70, or greater than 60 percent.

The term "complementary sequences", as used herein, may also include, or be formed entirely from, non-Watson-Crick base pairs and/or base pairs formed from non-natural and modified nucleotides, in as far as the above requirements with respect to their ability to hybridize are fulfilled.

The term "hybridization," "hybridize," "anneal" or "annealing" as used herein refers to the ability, under the appropriate conditions, for nucleic acids having substantially complementary sequences to bind to one another by Watson & Crick base pairing. Nucleic acid annealing or hybridization techniques are well known in the art. See, e.g., Sambrook, et al., Molecular Cloning: A Laboratory Manual, Second Edition, Cold Spring Harbor Press, Plainview, N.Y. (1989); Ausubel, F. M., et al., Current Protocols in Molecular Biology, John Wiley & Sons, Secaucus, N.J. (1994), or physiological conditions within the cell.

The term "introducing into a cell", "introduction into a cell" as used herein refers to facilitating uptake or absorption into the cell, as is understood by those skilled in the art. Absorption or uptake of the editing oligonucleotide can occur through unaided diffusive or active cellular processes, or by auxiliary agents or devices. The meaning of this term is not limited to cells in vitro; a editing oligonucleotide may also be "introduced into a cell", wherein the cell is part of a living organism. In such instance, introduction into the cell will include the delivery to the organism. For example, for in vivo delivery, editing oligonucleotide can be injected into a tissue site or administered systemically. In vitro introduction into a cell includes methods known in the art such as electroporation, microinjection, nucleoporation, lipofection or ballistic methods.

The term "edit" when used in reference to a target sequence, herein refers to the at least partial editing of the target gene, as manifested by a change in the sequence in the target gene. The extent of editing may be determined by isolating RNA or DNA from a first cell or group of cells in which the target gene is transcribed and which has or have been treated with an editing oligonucleotide, as compared to a second cell or group of cells substantially identical to the first cell or group of cells but which has or have not been so treated (control cells).

Alternatively, the degree of editing may be given in terms of a reduction or increase of a parameter that is functionally linked to the target gene transcription, e.g. the amount of protein encoded by the target gene which is secreted by a cell, or the number of cells displaying a certain phenotype, e.g. apoptosis. In principle, editing may be determined in any cell expressing the target by any appropriate assay.

For example, in certain instances, a target gene is edited in at least about 0.1%, 1%, 3%, 5%, 10%, 20%, 25%, 35%, or 50% of the targeted cells by administration of the editing oligonucleotide of the invention. In a particular embodiment, a target gene is edited in at least about 60%, 70%, or 80% of the targeted cells by administration of the editing oligonucleotide of the invention. The target cell often contains two copies of the target gene, and one or both of those copies can be edited. In some cases, the target cell contains only one copy of the gene targeted for editing and consequently only one desired edit per cell can occur.

The terms "treat", "treatment", and the like, refers to relief from or alleviation of a condition. In the context of the present invention insofar as it relates to any of the other conditions recited herein below, the terms "treat", "treatment", and the like mean to relieve or alleviate at least one symptom associated with such condition, or to slow or reverse the progression of such condition, or to protect against future disease formation. Treatment may also include modifying the properties of an organism in case of agriculture and industrial applications.

As used herein, the phrases "therapeutically effective amount" and "prophylactically effective amount" refer to an amount that provides a therapeutic benefit in the treatment, prevention, or management of a condition or an overt symptom of the condition. The specific amount that is therapeutically effective can be readily determined by an ordinary medical practitioner, and may vary depending on factors known in the art, such as, e.g. the type of disease, the patient's history and age, the stage of the disease, and the possible administration of other treatment agents.

As used herein, a "pharmaceutical composition" comprises a pharmacologically effective amount of an editing oligonucleotide and a pharmaceutically acceptable carrier. As used herein, "pharmacologically effective amount," "therapeutically effective amount" or simply "effective amount" refers to that amount of an editing oligonucleotide effective to produce the intended pharmacological, therapeutic or preventive result. For example, if a given clinical treatment is considered effective when there is at least a 25% reduction in a measurable parameter associated with a disease or disorder, a therapeutically effective amount of a drug for the treatment of that disease or disorder is the amount (including possible multiple doses) necessary to effect at least a 25% reduction in that parameter.

The term "pharmaceutically acceptable carrier" refers to a carrier for administration of a therapeutic agent. Such carriers include, but are not limited to, saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, tablets may be coated with a material such as glyceryl monostearate or glyceryl distearate, to delay absorption in the gastrointestinal tract of Editing Oligonucleotides.

Figure 19:
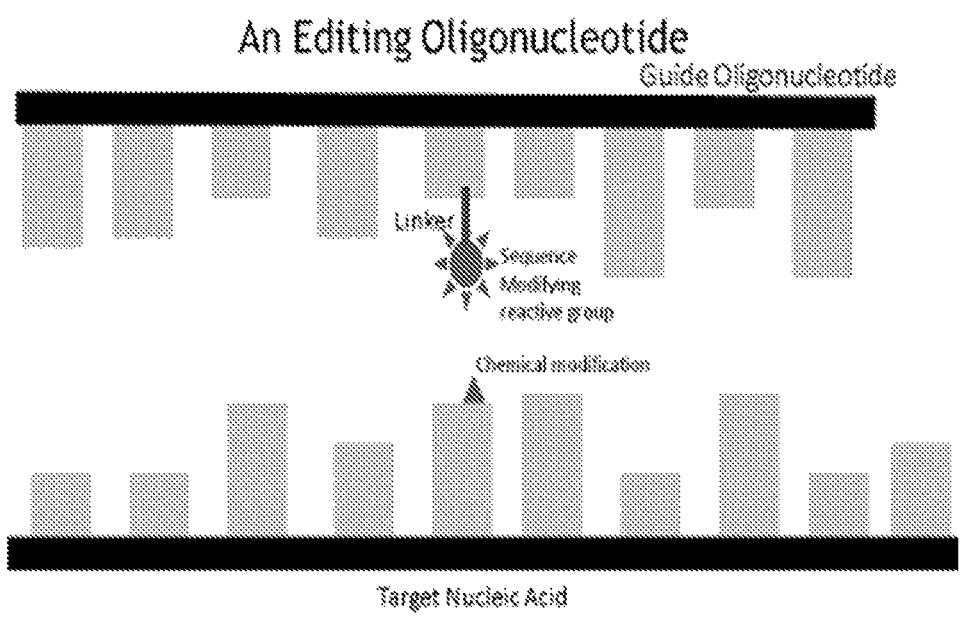
FIG. 19: The components of an embodiment of an editing oligonucleotide that acts by chemically modifying the targeted nucleobase (large rectangles represent pyrimidines and the smaller rectangles represent purines).

In one aspect of this invention, a single-stranded oligonucleotide complementary to one of the DNA strands of the genome is utilized for sequence editing (see FIG. 19). The desired edit may be a transition or transversion, or a deletion or insertion. In this aspect of the invention, the editing oligonucleotide sequence is the sequence desired after the editing is completed. Without being bound by a particular theory or mechanism, the editing oligonucleotide binds to the partially complementary or fully complimentary target genomic DNA sequence when the target sequence is separated from the opposite genomic strand during cellular processes such as transcription or replication. In some cases, the hybridization of the editing oligonucleotide to a double-stranded genomic DNA target can occur during "breathing", transient melting or unwinding of the target DNA. Once the heteroduplex is formed between the editing oligonucleotide and target genomic DNA strand, the area of non-perfect complementarity is corrected by cellular DNA repair (including homologous recombination (HR). When the editing oligonucleotide is used as the template for repair, the desired edit will be incorporated into the targeted genomic DNA strand.

The editing oligonucleotides of the present invention include some or all of the following segments, listed in order from 5' to 3': a 5' terminal segment; a 5' proximal segment; a 5' editing segment; an editing site; 3' editing segment; a 3' proximal segment; and a 3' terminal segment. These segments are discerned by their location and/or chemical modifications but are contiguously linked by the nucleic acid backbone, whether modified or natural DNA or RNA.

Nucleotides in each of these segments may be optionally modified to improve one or more of the following properties of the editing oligonucleotides: efficiency of editing; pharmacokinetic properties; bio-distribution; nuclease stability in serum; nuclease stability in the endosomal/lysosomal pathway; nuclease stability in the cytoplasm and nucleoplasm; toxicity (e.g. immune stimulation of toll-like receptors) and the minimal length necessary for efficient editing (e.g., shorter oligonucleotides are generally less expensive to make and easier to deliver to a cell in vivo). Non-limiting examples of such modifications are provided herein.

The editing oligonucleotide may comprise a subset or all of the seven segments listed above, and will include an editing site and at least one segment, 5' and 3' to the editing site. Each of these segments may optionally contain the same or different chemical modifications to enhance the properties of the editing oligonucleotide, and the modifications can in some cases be uniform throughout the segment, and in other cases only occur on a portion of nucleotides in the segment.

Other embodiments include editing oligonucleotides with reversible charge-neutralizing phosphotriester backbone modifications. These modifications have the advantage of imparting improved delivery and nuclease stability to the oligonucleotide it travels to the target cell's cytoplasm. Once in the target cell cytoplasm, the modifications are removed by cellular esterases, liberating an editing oligonucleotide with natural or more natural structure that is better recognized by the cellular homologous recombination and mismatch repair machinery (Meade, E. R. et al. Efficient delivery of RNAi prodrugs containing reversible charge-neutralizing phosphotriester backbone modifications. *Nature Biotechnology* 32:1256-1261 (2014). doi:10.1038/nbt.3078).

I. EDITING OLIGONUCLEOTIDES

In certain embodiments, the editing oligonucleotides of the invention have the structure according to Formula (I):

$$T_5\text{-}P_5\text{-}E_5\text{-}S_E\text{-}E_3\text{-}P_3\text{-}T_3 \tag{I}$$

Figure 25:
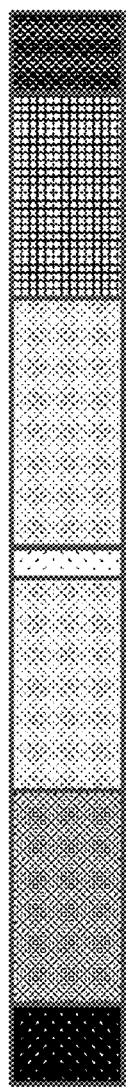
FIG. 25: Schematic of editing oligonucleotide with optional segments.

See FIG. 25 for a schematic representation of Formula (I).

A. The 5' Terminal Segment ($T_5$)

The 5' terminal segment may be more amenable to a multitude of different types of modifications than the 3' terminus because the 3' terminus may function in priming DNA extension, which may limit the 3'-terminal segment to a modification having a generally free 3' hydroxyl. This priming function is not usually necessary at the 5' terminus. An optional 5' terminal segment, which may be from zero to five nucleotides in length, functions to block 5' exonucleases that may otherwise readily degrade the editing oligonucleotide in bodily fluids (e.g., blood or interstitial fluids), culture media, the endocytic pathway, or the cytoplasm or nucleoplasm. This segment may comprise a non-nucleotide end-blocking group and/or modified nucleotide(s) that are more nuclease resistant than the 5' proximal segment (e.g., inverted bases, such as inverted T). If the 5' terminal segment is not employed, then the 5' proximal segment is simply the most 5' portion of the editing oligonucleotide. Non-nucleotide end-blocking groups may include any linker known to those skilled in the art for use in performing this task, such as for example: 3' C3 amino linker, 3' C7 amino linker, 5' & 3' C6 amino linker, 5' C12 amino linker, 5' photo-cleavable amino linker, 3' C3 disulfide linker, 5' & 3' C6, disulfide linker, dithiol linker, 4-formylbenzamide, aldehyde, C8-alkyne-thymidine, carboxy-dT linker, DADE linker (5' carboxyl linker), 3' glyceryl, 5' hexynyl, thymidine-5-C2 and C6 amino linker, 2'-deoxyadenosine, 8-C6 amino linker, 2'-deoxycytidine-5-C6 amino linker, 2'-deoxyguanosine-8-C6 amino linker, C7, and an internal amino linker. The linker lengths may range from one carbon to about twenty carbons or equivalent length of other chemistries, but preferably below ten carbons or ten carbon equivalent length.

The 5' terminal nucleotide exonuclease resistant segment may comprise one, two, three or four phosphorothioate modifications. In addition to these one or more phosphorothioate modifications, or in place of them, the 5' terminal exonuclease resistant nucleotides may comprise 2' sugar modifications, which are known to enhance exonuclease stability. Additionally, neutral nucleotide analogues such as methylphosphonates, morpholinos or PNAs are highly resistant to exonucleases, and one, two, three, four or five of such modifications at the 5' terminus may be utilized as end-blocking groups. In a preferred embodiment the 5' terminus is two methylphosphonates (Table 1). These end groups don't necessarily have to be complementary to the target.

B. The 5' Proximal Segment ($P_5$)

The 5' proximal segment may be more amenable to a multitude of different types of modifications than the 3' terminus for some of the same reasons as previously stated for the 5' terminal segment above. It may be from one to 150 nucleotides in length and preferably from about five to about twenty nucleotides in length. The main function of the 5' proximal segment is to enhance the affinity and ability of the editing oligonucleotide to hybridize to the target sequence. Therefore, this segment can optionally be more substantially modified than the editing segment. The 5' proximal segment may contain any of the oligonucleotide modifications referenced herein. This segment may be comprised of DNA or RNA (optionally 2' modified RNA defined broadly to include LNAs and other constrained backbones). While additional phosphorothioates (e.g., diphosphorothioates and phosphorothioates with enhanced chiral purity) in this region are not strictly required for nuclease stability, additional phosphorothioates will be useful to enhance nuclease stability of RNA and DNA linkages. Also, even when the phosphorothioates in this segment are not necessary for nuclease stability, they may add to the overall phosphorothioate content, which due to the chemically "sticky" nature of phosphorothioates, increases serum protein binding and cell binding that leads to increased serum half-life in animals and humans and enhances cytoplasmic uptake. For these reasons, in a preferred embodiment, the total phosphorothioate content of the editing oligonucleotide may be greater than five, ten, fifteen or twenty. A content of about twenty phosphorothioates often provides for excellent serum protein binding and cell binding/uptake. However, because large numbers (e.g., more than 6) of phosphorothioate linkages in the complementary region of editing oligonucleotides can inhibit editing efficiency, a phosphorothioate tail may be added to the 5' or 3' terminus of the region complementary to the target DNA. This tail may be from 1 to about 4, about 5 to about 9 nucleotides or about 10 to about 25 nucleotides in length and may preferably be positioned in a region non-complementary to the target.

C. The 5' Editing Segment ($E_5$)

The 5' editing segment is from one to about ten nucleotides in length, or one to about 100 nucleotides, or one to about 200 nucleotides and is positioned on the 5' end of the editing site, which is sufficiently close in proximity to the editing site to affect the cellular machinery that results in editing of the opposing genome DNA strand. While not being bound by any theory, the DNA mismatch repair system may use the editing segment (which is the 5' editing segment, editing site and 3' editing segment) as the template strand for editing. Therefore, the nucleotides in the 5' editing segment, editing site, and 3' editing segment are preferably substantially similar to natural DNA, (e.g., in FIG. 2, compound 100013 has about 8 unmodified nucleotides 5' of the editing site, which did not inhibit the overall editing efficiency, compared to the parent compound) or natural DNA chemistry and may be unmodified or include one or more modifications such as phosphorothioates, 5'S, 2'F, 2' amino or 3'S, reversible charge-neutralizing phosphophotriester and nucleobase modifications.

In one preferred embodiment of the present invention, one, some or all of the deoxy-cytosines in the editing oligonucleotide are modified to 5 methyl cytosine, particularly, the cytosine nucleosides within about five to about 10 bases, 5' or 3', of the editing site(s). One reason for incorporating 5 methyl cytosines into the editing oligonucleotide is that during replication followed by mismatch repair, the mismatch repair machinery recognizes unmethylated cytosines as the nascent strand, and preferentially uses the 5 methyl cytosine containing DNA strand as the template-strand for repair. In addition, if the editing oligonucleotide contains few or no 5 methyl cytosines, then the repair machinery will likely not select this strand as the template during the DNA repair reaction that leads to editing. The fact that editing oligonucleotides in the art have not contained multiple 5-methyl cytosines is one of the reasons for their relatively low efficiency in editing.

In a preferred embodiment, the editing oligonucleotide has a 5-methyl cytosine in a CpG sequence at the editing site. In a more preferred embodiment, this CpG in the editing site is mispaired to TpG in the target sequence. In this case, the cellular 5-methyl binding protein will bind to the mismatched methylated CpG and lead the cellular mismatch repair system to convert the mismatched T into a matched C. The 5' editing segment may contain no modifications or one or more modifications up to the number of bases in the segment.

D. The Editing Site ($S_E$)

The editing site contains the nucleotide(s) which are not complementary to the target genomic DNA and may be from one to six nucleotides in length, but can be longer as required. In the case of a transition/transversion modification, the editing site is equal to the number of mismatched bases (e.g., one to about six nucleotides, particularly 1). In the case of editing to create a deletion, the editing site is the junction between the two 5' and 3' nucleotides which are base-paired to the target genomic DNA strand, just opposite the non-based paired nucleotides in the genomic DNA. In some cases, one editing oligonucleotide may be used to treat different mutations at nearby sites within the region of complementarity to the target DNA that occur in different patients in the population. In this case there will be different editing sites, depending on the patient's mutant genotype. In these cases, the editing site would include the 5' and 3' most mutations and the region in between those mutations. In one preferred embodiment, the editing site hybridizes to an entire exon in the target gene.

E. The 3' Editing Segment ($E_3$)

The 3' editing segment has the same range of features, properties and parameters as the $E_5$ the 3' editing segment, except for its location being 3' of editing site.

F. The 3' Proximal Segment ($P_3$)

Figure 2:
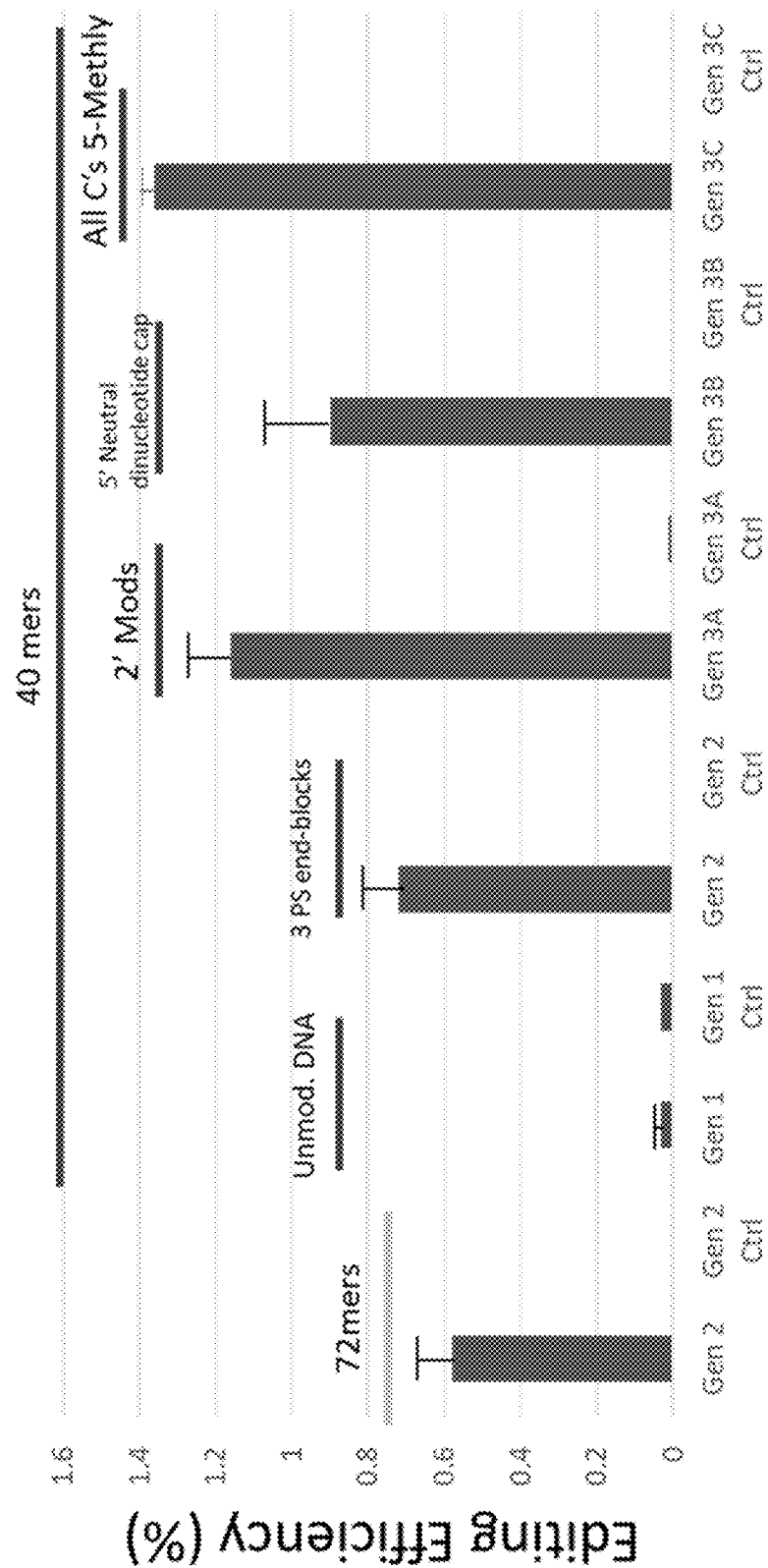
FIG. 2: displays data from some of the oligonucleotides presented in Table 1 showing editing efficacy by percentage. Gen 3A is oligonucleotide #100013 and #100014, Gen 3B is oligonucleotide #100015 and #100016, Gen 3C is oligonucleotide #100017 and #100018, Gen 1 is oligonucleotide #100003 and #100004 and Gen 2 is oligonucleotide #100005 and #100006.

The 3' proximal segment has the same range of features and parameters as the 5' proximal segment, except for its location relative to the other segments. In a preferred embodiment, the 3' proximal segment is comprised of 2' modified nucleotides, and in a more preferred embodiment, it is comprised of 2'F modified nucleotides. In a most preferred embodiment, it comprises 8 2' F modified nucleotides (FIG. 2).

G. The 3' Terminal Segment (T$_3$)

The 3' terminal segment may comprise the same range of features and properties as the 5' terminal segment, except as elaborated below. The 3' terminal segment may serve as a primer for DNA synthesis during DNA replication and repair, thus allowing the editing oligonucleotide to become contiguously incorporated into the genomic DNA. Consequently, in one embodiment this segment will have a free 3' hydroxy and may be made of natural-like modifications or unmodified DNA or RNA.

While non-nucleotide end-blocking groups at the 3' terminus may, in some cases, reduce or eliminate editing activity, if there is a region of RNA between the editing site and the 3' terminus of the editing oligonucleotides that is cleaved by RNase H upon hybridization of the editing oligonucleotide to the target DNA, then a free 3' hydroxyl suitable as a primer for chain extension will be created. Also, another editing mechanism, known as mismatch repair, may not require a free 3' hydroxyl or region of the editing oligonucleotide base paired to the target at the 3' terminus. In this case, 3' non-nucleotide end-blocking groups or other substantial modifications may be employed in the 3' terminal segment. These end-blocking groups or modifications are similar or analogous to the 5' end blocking groups described above in the description of the 5' terminal segment. Modifications that are 3' specific would be changed to the 5' specific moiety. For example, and inverted T placed on the 5' end would have a 3' to 5' linkage.

The oligonucleotide of Formula (I) may comprise 20-2000 nucleotides. In one embodiment, the oligonucleotide may comprise 100-250 nucleotides. In another embodiment, the oligonucleotide may comprise 250-2000 nucleotides. In a particular embodiment, the oligonucleotide comprises 20-100 nucleotides. More particularly, the oligonucleotide comprises 25-90 nucleotides.

The current design of single-stranded editing oligonucleotides using the methods of Brachman and Kmiec employs unmodified DNA, which is less efficient for editing, or three phosphorothioates on each end with the rest of the editing oligonucleotide comprising unmodified DNA, which is more efficient for editing, having an optimal length of approximately seventy-two nucleotides in both cases. While Brachman and Kmiec found that synchronized cells treated in S-phase were most efficiently edited (Engstrom and Kmiec, Cell Cycle 7(10):1402-1414, 2008), we now know that editing oligonucleotide designs of Kmiec described above are highly susceptible to cellular endonucleases. In order to increase the editing efficiency, and not require cell synchronization (e.g. because a stable editing oligonucleotide will persist in each cell until the cell enters the S-phase naturally), the present invention provides editing oligonucleotides that have enhanced nuclease resistance. Tables 1-3 provide examples of these editing oligonucleotides. Increased resistance to cellular endonucleases may be achieved by modifying one or more of the nucleotide linkages to phosphorothioate linkages that are positioned near the 5' and/or 3' terminus. In one embodiment, four or more phosphorothioate linkages are preferred. Resistance may also be achieved by replacing all of the nucleotide linkages with phosphorothioate linkages, except for the "editing segment". In some embodiments, the phosphorothioate modifications may comprise from one up to seven of the nucleotide linkages surrounding the editing bases (e.g., the bases that are different from the target sequence). In one embodiment all the linkages are phosphorothioate DNA. The phosphothioate linkages can also be wholly or partly alternating, with every other linkage being a phosphorothioate linkage, or every third linkage being a phosphorothioate linkage, or 2 phosphorothioate linkages alternating with one or two phosphodiester linkages, and the like. The editing oligonucleotide may comprise from about 10%, 20%, 30%, 40%, 50%, 60%, 70%, 80%, 90% or 100% phosphorothioate linkages. These phosphorothioate configurations can be combined with other modifications or natural sugars, as described herein. In particular, some of the DNA sugars may be replaced with RNA sugars. Preferably, the RNA substitutions will comprise a block of RNA linkages beginning at the 3' terminus, and extending in the 5' direction for one, two, three, four, five, six, seven, eight, nine or ten bases. This is to make the 3' end appear as a natural Okazaki fragment, which will lead to more natural priming of synthesis and removal by RNase H. However the RNA modifications are not preferred in the "editing segment", because it is not desirable to have the editing segment removed by RNase H.

H. Other Modifications

Another approach to making the editing oligonucleotide more efficient is to increase affinity through chemical modification. The modifications described herein may be combined in the editing oligonucleotide and include 2'-O-methyl RNA, 2'F RNA and constrained nucleic acids, including LNAs. These modifications have the additional advantage that they can also reduce immune stimulation. The modifications may be grouped to form a high affinity "seed" region for hybridization. In a preferred embodiment, this seed region would be positioned in the 5' proximal segment, with about two to about twelve successive modifications. In other embodiments, the seed region may be positioned in the 3' proximal segment. In a less preferred embodiment, the modification may be positioned in the "editing segment". This is less preferred because the editing segment must interact with cellular repair machinery, and certain modifications in this segment may interfere with repair. The modifications can be alternating or every third or fourth linkage, in the 5' segment, the editing segment and/or the 3' segment. The total proportion of chemically modified nucleobases in the 5' segment, 3' segment, or editing segment may range independently from about 20%, 30%, 50%, 60%, 70%, 80%, 90% or 100%.

Provided herein are various embodiments of the oligonucleotide of Formula (I). In one embodiment, Formula (I) is RNA. In another embodiment, Formula (I) is DNA. In a particular embodiment, Formula (I) is single-stranded. In one embodiment, Formula (I) is unmodified. In one embodiment, Formula (I) is chemically-modified. Chemical modifications include sugar modifications (particularly, e.g., 2'-O-methyl and 2'-fluoro). In one embodiment, Formula (I) comprises a backbone modification. In another embodiment, Formula (I) comprises a backbone modification, as described herein. In another embodiment, Formula (I) comprises a linker, as described herein. In another embodiment, Formula (I) further comprises a conjugated molecule (e.g., gal-nac or a lipophilic modification). The foregoing modifications may be present in various combinations. For example, one, two or three backbone modifications may be present with one, two or three sugar modifications and/or a linker and/or a conjugated molecule.

Certain oligonucleotides of the invention comprise one or more chemical modifications that react with, or promote a reaction with, a nucleotide on a target sequence. Examples of such reactions include alkylation, acetylation, cross-linking, amination, de-amination, generation of a free (non-covalently bound) reactive compound.

Oligonucleotides of the invention may comprise protecting groups. Suitable protections groups are known to those skilled in the art to protect chemically-reactive groups during synthesis, purification, storage and during use (e.g., to protect the oligonucleotide from conditions including acidity, intracellular esterases or reducing conditions. While it is convenient to use only a single oligonucleotide to achieve editing, certain enhancements to the embodiments herein include additional oligonucleotides. The use of a "helper" oligonucleotide or "helper" oligonucleotides, wherein "helper" oligonucleotide(s) refers to an oligonucleotide which would bind tandemly to the editing oligonucleotide (e.g., at the 3' end, 5' end or both ends in the case of two helper oligonucleotides or further away from the editing oligonucleotide binding site, for example with 200 nucleotides 5' or 3' of the editing site. The helper oligonucleotides will help open up the structure of the target site or otherwise improve the efficiency of binding of the editing oligonucleotide. Another target of helper oligonucleotides may be the opposite strand of the DNA strand targeted by the editing sequence. In this case, the helper oligonucleotide(s) preferably bind just 5' and/or 3' of the binding site of the editing oligonucleotide, so as to not hybridize strongly to the editing oligonucleotide itself. In other embodiments, the 5' and/or 3' helper oligonucleotides overlap with the editing oligonucleotide binding site by about 1-5, about 5-10, or about 1-15 bases. In this manner, the helper oligonucleotides would not bind too tightly to the editing oligonucleotide to negatively impact the editing oligonucleotides binding to the target. These helper oligonucleotides could optionally be linked to the editing oligonucleotide covalently by phosphodiester or modified phosphodiester linkages, or by other covalent linkers. In another embodiment triplex forming oligonucleotides or oligonucleotide analogs bind to the target DNA within about 200 nucleotides of the editing site resulting in increased editing efficiency (McNeer, N. A. et al., Nature Comm. DOI:10.1038/ncomms 7952 pgs. 1-11, 2015), Bahal et al. Current Gene Therapy 14(5) pp 331-42 (2014), Chin et al. PNAS 105(36):13514-13519 (2008), Rogers et al. PNAS 99(26):16695-16700 (2002), and U.S. Pat. No. 8,309, 356).

Some helper oligonucleotides protect oligonucleotides that are complementary to the editing oligonucleotide and block nuclease degradation by single-strand specific nucleases. The protecting oligonucleotides cover all or a desired part of the editing oligonucleotide. They are generally shorter than the editing oligonucleotide so that a portion of the editing oligonucleotide remains single-stranded and thus available for hybridization to the target DNA. In one embodiment, the protector oligonucleotides are comprised of some or all RNA regions complementary to the DNA portions of the editing oligonucleotide, so that they may be removed by RNase H in the cell, to expose more single-stranded regions of the editing oligonucleotide.

I. Exogenous Proteins

While it is advantageous to not strictly require exogenous proteins in editing compositions, certain exogenous proteins can enhance the embodiments described above, by protecting the editing oligonucleotide from nuclease degradation and by enhancing the binding of the editing oligonucleotide to target genomic DNA. One or more of the following proteins or ribonucleoproteins may be added along with editing oligonucleotides, programmable nucleases including zinc finger nucleases (Carroll D. Genetics 188:773e82. (2011)), TALENs, mega TALENs, other homing endonucleases, CRISPR-Cas9 (Jinek et al. Elife 2013; 2:e00471), or homologous or similarly acting ribonucleoproteins (i.e. Cpf1, C2C1 or C2C3) including mutated forms thereof that have been selected to increase target specificity by reducing DNA binding affinity (eSpCas9, Slaymaker et al., Rationally Engineered Cas9 Nucleases with Improved Specificity, Science (2015)), and mutated forms that have been selected to tolerate more DNA substitutions in the crRNA region so that the "crRNA" can act as a donor DNA for editing, and mutated forms in which the Cas9 nuclease is inactivated, RecA, Lambda phage beta protein. (U.S. Pat. No. 7,566, 535), ssDNA binding protein, RADs or Argonauts.

The proteins can be manufactured separately from the editing oligonucleotide, purified then pre-complexed with the editing oligonucleotide(s) (Kim et al. Genome Res. 24:1012e9 (2014)), or the proteins may be expressed in the target cells/tissues. Expression of the exogenous proteins in cells or tissues can be done with methods known in the art, including gene therapy vectors, naked DNA transfection, or mRNA transfection.

In the case of Cas9, a preferred embodiment deploys a Cas9 with both nuclease domains inactivated by mutations known in the art. The crRNA is preferably separate from the tracRNA and has the desired edited sequence. The crRNA also has at least one and up to about fifteen DNA linkages substituted in and optionally around the editing site, as defined herein. In this way, the specificity and non-chromosomal cutting advantages of the Brachman Kmiec-type genome editing or the editing employing oligonucleotides containing chemically reactive groups that modify the target nucleobase to change its coding as described herein will be enhanced in efficacy by the enhanced hybrid formation driven by Cas9. In another embodiment, the about 18 nucleotide guide RNA portion of the crRNA or tracRNA is extended to the 5' or 3', with an editing oligonucleotide. The editing oligonucleotide may be unmodified or have various modifications described herein. The editing oligonucleotide would be attached to the crRNA or tracRNA guide covalently by a phosphodiester (or phosphodiester analog) bond, or chemical linker, or non-covalently through base-pairing to a portion of the CRISPR guide RNA, or an extension of the CRISPR guide RNA. In a preferred embodiment, the editing oligonucleotide portion would hybridize contiguously to the sequence complimentary to the guide portion of the tracRNA or crRNA, extending the duplex with the target DNA into the region of the targeted mutation. This approach would be more efficient than oligonucleotide-directed genome approaches that don't use CRISPR-Cas9, because Cas-9/CRISPR enhances the efficiency of strand-invasion. This approach would be more selective and simple than common Cas-9/CRISPR approaches which cleave the targeted chromosome, and require a separate donor oligo.

In each case, editing efficiency can be optionally enhanced by treatment of the targeted cell or organism with drugs that synchronize cells in S-phase during or prior to the exposure to the editing oligonucleotide, slow the replication forks (Erin E. Brachman and Eric B. Kmiec DNA Repair 4:445-457 (2005), or otherwise increase the expression and/or activity of the homologous DNA repair machinery, such as hydroxyl urea, HDAC inhibitors or Camptothecin (Ferrara and Kmiec Nucleic Acids Research, 32(17):5239-5248, 2004).

The chemically modified editing oligonucleotides described herein, can be used as the donor oligonucleotides for homologous recombination editing. While precise editing with CRISPR-Cas9 uses donor DNA, CRISPR-Cas9 is not typically used with chemically modified donor DNA as described herein. Another method for enhancing the efficiency of homologous recombination of a chemically modified "donor" editing oligonucleotide is the addition of a PNA-clamp near the target mutation (Schleifman et al., Chem. Biol. 18(9):1189-1198, 2011). While Glazer has employed this technique with $2^{nd}$ generation editing chemistries (e.g. three phosphothioate modification on one of both ends of the donor DNA oligonucleotide), the PNA-clamps have not been employed with the $3^{rd}$ generation more heavily modified donor DNA described and referenced herein. (Bakal et al. Current Gene Therapy 14(5):331-42 (2014), Chin et al. PNAS 105 (36):13514-13519 (2008), Rogers et al. PNAS 99 (26):16695-16700 (2002) and U.S. Pat. No. 8,309,356.)

J. Synthesis

Teachings regarding the synthesis of particular oligonucleotides to be utilized as editing oligonucleotides of the present invention may be found in the following U.S. patents: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone-modified oligonucleotides and the preparation thereof through reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having .beta.-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups may be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. Nos. 5,223,168 and 5,608,046, both drawn to conjugated 4'-desmethyl nucleoside analogs; U.S. Pat. Nos. 5,602,240, and 5,610,289, drawn to backbone-modified oligonucleotide analogs; U.S. Pat. Nos. 6,262,241, and 5,459,255, drawn to, inter alia, methods of synthesizing 2'-fluoro-oligonucleotides.

The incorporation of a 2'-O-methyl, 2'-O-ethyl, 2'-O-propyl, 2'-O-allyl, 2'-O-aminoalkyl or 2'-deoxy-2'-fluoro group in nucleosides of an oligonucleotide confers enhanced hybridization properties to the oligonucleotide. Further, oligonucleotides containing phosphorothioate backbones have enhanced nuclease stability. Thus, functionalized, linked nucleosides of the invention may be further modified to include LNAs, constrained sugars, a 2'-deoxy-2'-fluoro group, a phosphorothioate backbone and/or 2' modified sugars, wherein the sugar may be modified to include a 2'-O-methyl, 2'-O-ethyl, 2'-O-propyl, 2'-O-aminoalkyl, 2'-O-allyl or 2'-methoxyethoxy.

K. Protecting Groups

In many cases, protecting groups are used during the preparation of the compounds of the invention. As used herein, the term "protected" means that the indicated moiety has a protecting group appended thereon. In some preferred embodiments of the invention, compounds contain one or more protecting groups. A wide variety of protecting groups can be employed in the methods of the invention. In general, protecting groups render chemical functionalities inert to specific reaction conditions, and can be appended to and removed from such functionalities in a molecule without substantially damaging the remainder of the molecule.

Representative hydroxyl protecting groups, for example, are disclosed by Beaucage et al. (Tetrahedron, 48:2223-2311, 1992). Further hydroxyl protecting groups, as well as other representative protecting groups, are disclosed in Greene and Wuts, Protective Groups in Organic Synthesis, Chapter 2, 2d ed., John Wiley & Sons, New York, 1991, and Oligonucleotides And Analogues A Practical Approach, Ekstein, F. Ed., IRL Press, N.Y, 1991.

Examples of hydroxyl protecting groups include, but are not limited to, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, 2,6-dichlorobenzyl, diphenylmethyl, p,p'-dinitrobenzhydryl, p-nitrobenzyl, triphenylmethyl, trimethylsilyl, triethylsilyl, t-butyldimethylsilyl, t-butyldiphenylsilyl, triphenylsilyl, benzoylformate, acetate, chloroacetate, trichloroacetate, trifluoroacetate, pivaloate, benzoate, p-phenylbenzoate, 9-fluorenylmethyl carbonate, mesylate and tosylate.

Amino-protecting groups stable to acid treatment are selectively removed with base treatment, and are used to make reactive amino groups selectively available for substitution. Examples of such groups are the Fmoc (E. Atherton and R. C. Sheppard in The Peptides, S. Udenfriend, J. Meienhofer, Eds., Academic Press, Orlando, 1987, volume 9, p. 1) and various substituted sulfonylethyl carbamates exemplified by the Nsc group (Samukov et al., Tetrahedron Lett., 35:7821, 1994; Verhart and Tesser, Rec. Tray. Chim. Pays-Bas, 107:621, 1987).

Additional amino-protecting groups include, but are not limited to, carbamate protecting groups, such as 2-trimethylsilylethoxycarbonyl (Teoc), 1-methyl-1-(4-biphenylyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide protecting groups, such as formyl, acetyl, trihaloacetyl, benzoyl, and nitrophenylacetyl; sulfonamide protecting groups, such as 2-nitrobenzenesulfonyl; and imine and cyclic imide protecting groups, such as phthalimido and dithiasuccinoyl. Equivalents of these amino-protecting groups are also encompassed by the compounds and methods of the invention.

L. Solid Supports

Many solid supports are commercially available and one of ordinary skill in the art can readily select a solid support to be used in the solid-phase synthesis steps. In certain embodiments, a universal support is used. A universal support allows for preparation of oligonucleotides having unusual or modified nucleotides located at the 3'-terminus of the oligonucleotide. Universal Support 500 and Universal Support II are universal supports that are commercially available from Glen Research, 22825 Davis Drive, Sterling, Va. For further details about universal supports see Scott et al., Innovations and Perspectives in solid-phase Synthesis, 3rd International Symposium, 1994, Ed. Roger Epton, Mayflower Worldwide, 115-124]; Azhayev, A. V. Tetrahedron, 55, 787-800, 1999; and Azhayev and Antopolsky Tetrahedron, 57, 4977-4986, 2001. In addition, it has been reported that the oligonucleotide can be cleaved from the universal support under milder reaction conditions when oligonucleotide is bonded to the solid support via a syn-1,2-acetoxyphosphate group which more readily undergoes basic hydrolysis. See Guzaev, A. I.; Manoharan, M. J. Am. Chem. Soc., 125:2380, 2003.

Specific examples of preferred modified oligonucleotides envisioned for use in the ligand-conjugated oligonucleotides of the invention include oligonucleotides containing modified backbones or non-natural internucleoside linkages such as peptide nucleic acid (PNA), morpholino nucleic acids (MNA) or other modified backbones. As defined here, oligonucleotides having modified backbones or internucleoside linkages include those that retain a phosphorus atom in the backbone and those that do not have a phosphorus atom in the backbone. For the purposes of the invention, modified oligonucleotides that do not have a phosphorus atom in their intersugar backbone can also be considered to be oligonucleosides.

Specific oligonucleotide chemical modifications are described below. It is not necessary for all positions in a given compound to be uniformly modified. Conversely, more than one modification may be incorporated in a single editing oligonucleotide compound or even in a single nucleotide thereof.

M. Internucleosidyl Linkages

Preferred modified internucleoside linkages or backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free-acid forms are also included. See also FIG. 20.

Representative United States patents relating to the preparation of the above phosphorus-atom-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,625,050; and 5,697,248, each of which is herein incorporated by reference.

Preferred modified internucleoside linkages or backbones that do not include a phosphorus atom therein (i.e., oligonucleosides) have backbones that are formed by short chain alkyl or cycloalkyl intersugar linkages, mixed heteroatom and alkyl or cycloalkyl intersugar linkages, or one or more short chain heteroatomic or heterocyclic intersugar linkages. These include those having morpholino linkages that may be formed, in part, from the sugar portion of a nucleoside; siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and —$CH_2$ component parts.

Representative United States patents relating to the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439. See FIG. 20 for a list of possible backbone modifications.

N. Nucleoside Mimetics

In other preferred oligonucleotide mimetics, both the sugar and the internucleoside linkage, i.e., the backbone, of the nucleoside units are replaced with novel groups. The nucleobase units are maintained for hybridization with an appropriate nucleic acid target compound. One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular an aminoethylglycine backbone. The nucleobases are retained and are bound directly or indirectly to atoms of the amide portion of the backbone. Representative United States patents that teach the preparation of PNA compounds include, but are not limited to, U.S. Pat. Nos. 5,539,082, 5,714,331 and 5,719,262. Further teaching of PNA compounds can be found in Nielsen et al., Science, 254:1497, 1991.

Some preferred embodiments of the invention employ oligonucleotides with phosphorothioate linkages and oligonucleosides with heteroatom backbones, and in particular —$CH_2$—NH—O—$CH_2$—, —$CH_2$—N($CH_3$)—O—$CH_2$— (known as a methylene(methylimino) or MMI backbone), —$CH_2$—O—N($CH_3$)—$CH_2$—, —$CH_2$—N($CH_3$)—N($CH_3$)—$CH_2$—, and —O—N($CH_3$)—$CH_2$—$CH_2$— (wherein the native phosphodiester backbone is represented as —O—P—O—$CH_2$—) of the above referenced U.S. Pat. No. 5,489,677 and the amide backbones of the above referenced U.S. Pat. No. 5,602,240. Also preferred are oligonucleotides having morpholino backbone structures of the above-referenced U.S. Pat. No. 5,034,506, see FIG. 20.

O. Nucleobase Modifications

The oligonucleotides employed in the editing oligonucleotides of the invention may additionally or alternatively comprise nucleobase modifications or substitutions. As used herein, "unmodified" or "natural" nucleobases include the purine bases adenine (A) and guanine (G), and the pyrimidine bases thymine (T), cytosine (C), and uracil (U). Modified nucleobases include other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (also known as pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. See also FIGS. 21 and 22.

Representative United States patents relating to the preparation of certain of the above-noted modified nucleobases as well as other modified nucleobases include, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; and 5,808,027.

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a target nucleic acid, a target region, target segment, or specified portion thereof. See FIG. 21 for a list of possible nucleobase modifications.

P. Complementarity

An editing oligonucleotide and a target nucleic acid are complementary to each other when a sufficient number of nucleobases of the oligonucleotide can hydrogen bond with the corresponding nucleobases of the target nucleic acid, such that a desired effect will occur (e.g., permitting the desired base modification to occur following hybridization).

Non-complementary nucleobases between an editing oligonucleotide and a target nucleic acid may be tolerated provided that the editing oligonucleotide remains able to specifically hybridize to the target nucleic acid. In certain embodiments, the editing oligonucleotide provided herein, or a specified portion thereof, are, or are at least, 70%, 80%, 85%, 86%, 87%, 88%, 89%, 90%, 91%, 92%, 93%, 94%, 95%, 96%, 97%, 98%, or 99% complementary to a target nucleic acid or specified portion thereof. Percent complementarity of an editing oligonucleotide with a target nucleic acid can be determined using routine methods. For example, an editing oligonucleotide in which 16 of 20 nucleobases are complementary to a target nucleic acid, and would therefore specifically hybridize, would represent 80% complementarity. In this example, the remaining noncomplementary nucleobases may be clustered or interspersed with complementary nucleobases and need not be contiguous to each other or to complementary nucleobases. They may be at the 5' end, 3' end or at an internal position of the editing oligonucleotide. In another example, an editing oligonucleotide which is 18 nucleobases in length having 1 (one) noncomplementary nucleobase, which is flanked by two oligonucleotides of complete complementarity with the target nucleic acid would have 94.4% overall complementarity with the target nucleic acid and would thus fall within the scope of the present invention.

Percent complementarity of an editing oligonucleotide with a region of a target nucleic acid can be determined routinely using BLAST programs (basic local alignment search tools) and PowerBLAST programs known in the art (Altschul et al., J. Mol. Biol., 215:403 410, 1990; Zhang and Madden, Genome Res., 7:649-656, 1997). The Gap program (Wisconsin Sequence Analysis Package, Version 8 for Unix, Genetics Computer Group, University Research Park, Madison WI), using default settings, utilizing the algorithm of Smith and Waterman (Adv. Appl. Math., 2:482-489, 1981) may also be used.

II. MODES OF ACTION

A. Hybridization

Hybridization between an editing oligonucleotide and a target nucleic acid may occur under varying stringent conditions, are sequence-dependent and are determined by the nature and composition of the nucleic acid molecules to be hybridized. The most common mechanism of hybridization involves hydrogen bonding (e.g., Watson-Crick, Hoogsteen or reversed Hoogsteen hydrogen bonding) between complementary nucleobases of the nucleic acid molecules.

Methods of determining whether a sequence is specifically hybridizable to a target nucleic acid are well known in the art. In certain embodiments, the editing oligonucleotides provided herein are specifically hybridizable with a target nucleic acid.

B. Target Binding

The editing oligonucleotides of the present invention are designed to target DNA or RNA. The editing nucleotide(s) may be flanked on one or both sides with oligonucleotides that are completely complementary or substantially complementary to the target nucleic acid.

The preferred method of binding is by strand displacement resulting in hybridization to either the Watson or Crick strand of the DNA, or when RNA is the target by hybridization of the antisense editing oligonucleotide to the sense RNA strand.

C. Editing Oligonucleotide

The editing oligonucleotide may optionally contain a "linker" that covalently attaches a delivery moiety to the oligonucleotide. The linker attachment may be to any nucleobase in the editing oligonucleotide, to the 5' terminus, to the 3' terminus, to a sugar residue, or to the backbone. The linker may be any linker known to those skilled in the art for use in performing this task. Alternatively, a linker may be utilized and tested to determine its performance in the editing oligonucleotide. For example, linkers that may be utilized with the present invention include: 3' C3 amino linker, 3' C7 amino linker, 5' & 3' C6 amino linker, 5' C12 amino linker, 5' photocleavable amino linker, 3' C3 disulfide linker, 5' & 3' C6, disulfide linker, dithiol linker, 4-formylbenzamide aldehyde, C8-alkyne-thymidine, carboxy-dT linker, DADE linker (5' carboxyl linker), 3' glyceryl, 5' hexynyl, thymidine-5-C2 and C6 amino linker, 2'-deoxyadenosine, 8-C6 amino linker, 2'-deoxycytidine-5-C6 amino linker, 2'-deoxyguanosine-8-C6 amino linker, C7, internal amino linker, photocleavable linker or an intercalator containing linker, in which the intercalating group serves to position a reactive group in proximity to the targeted nucleobase. The linker lengths may range from 1 carbon to about 20 carbons or equivalent length of other chemistries, but preferably below 10 carbons or 10 carbon equivalent length.

In the case of the chemical modification mode of editing, successful treatment with the editing oligonucleotide results in some proportion of the "target nucleic acid" becoming modified.

In the case of the chemical modification mode of editing, mutations in a nucleic acid sequence resulting from a change in a single nucleotide may be transitions or transversions. Transitions arise when a point mutation changes a purine nucleotide to another purine nucleotide such as adenosine to guanosine or a pyrimidine nucleotide to another pyrimidine nucleotide such as cytidine to thymidine.

When transitions or transversions arise in the genetic code they can directly affect the protein expressed from the mRNA by interfering with its production or by introducing a change in the protein's amino acid sequence during translation. The information provided in DNA that transcribed into mRNA provides discrete segments or lengths of nucleic acids that are translated into proteins. In addition, these segments contain control elements that indicate where translation should begin and end so that ribosomes are able to produce the protein with the proper amino acid sequence. Point mutations along the mRNA that produce stop codons signal the termination of translation and can prevent production of a desired protein or result in early termination of translation producing a non-functioning protein. While start codons require nearby sequences or initiation factors to start translation, a stop codon alone is sufficient to initiate termination.

The present invention provides for a correction of the point mutation returning targeted sequence to wild type or the equivalent, modifying the point mutation so that the codon while not being the wild type, nevertheless translates into the appropriate amino acid, or modifying the point mutation so that the stop codon becomes a read through codon allowing for production of the protein. Examples of point mutations that may converted to read through codons in mRNA include transitions 5' UAA to CAA; 5' UAG to CAG or UGG or 5' UGA to CGA or UGG and in DNA are 5' TAA to CAA; 3' ATT to GTT; 5' TAG to CAG or TGG; 3' ATC to GTC or ACC; 5' TGA to CGA or TGG; and 3' ACT to GCT or ACC.

When point mutations occur in the protein translation segment of the mRNA the resulting codons may be read as a different amino acid. For example, specific codon changes that can result from adenine to guanine transversions include: Met to Val; Tyr to Cys; His to Arg; Gln to Arg; Asp to Ser; Lys to Arg; Asp to Gly; and Glu to Gly. In addition, a stop codon can be mutated to an amino acid codon such as Amber Stop to Trp or UGA stop codon to Trp.

When point mutations occur in DNA or RNA, such as for example a T to C transition, transcription followed by translation can change amino acids in the resulting protein. For example, a change from T to C could result in an amino acid change of: Phe to Leu; Cys to Arg; Trp to Arg; Phe to Ser; Tyr to His; Ile to Thr; Met to Thr; Val to Ala; four of six consecutive serines to Pro; two of four consecutive leucines to Ser; or four of six leucines to Pro. In addition, a stop codon can be mutated to an amino acid codon such as UAA or UAG stop codons to Trp or UGA stop codon to Arg.

D. Editing by Chemical Modification of the Targeted Nucleobase

FIG. 19 shows the mechanism of editing utilizing the editing oligonucleotide of the present invention for the chemical modification mode of editing. The length of the editing oligonucleotide may vary depending on a number of physical aspects of the editing process including for example, the type of chemistry being utilized to perform the editing, the type of editing to be performed on the target and the length of the linker.

The editing oligonucleotide in the chemical modification method of editing comprises at least three components that include the "guide oligonucleotide", the "linker" that covalently attaches the "sequence modifying reactive group" to the guide oligonucleotide. In FIG. 19, the linker is shown attached to a nucleobase of the editing oligonucleotide. However, the attachment may be to any nucleobase in the editing oligonucleotide, to the 5' terminus, to the 3' terminus, to a sugar residue, or to the backbone. The linker may be any linker known to those skilled in the art for use in performing this task. Alternatively, a linker may be utilized and tested to determine its performance in the editing oligonucleotide. For example, linkers that may be utilized with the present invention include: 3' C3 amino linker, 3' C7 amino linker, 5' & 3' C6 amino linker, 5' C12 amino linker, 5' photocleavable amino linker, 3' C3 disulfide linker, 5' & 3' C6, disulfide linker, dithiol linker, 4-formylbenzamidealdehyde, C8-alkyne-thymidine, carboxy-dT linker, DADE linker (5' carboxyl linker), 3' glyceryl, 5' hexynyl, thymidine-5-C2 and C6 amino linker, 2'-deoxyadenosine, 8-C6 amino linker, 2'-deoxycytidine-5-C6 amino linker, 2'-deoxyguanosine-8-C6 amino linker, C7, internal amino linker, photocleavable linker or an intercalator containing linker, in which the intercalating group servers to position the reactive group in proximity to the targeted nucleobase. The linker lengths may range from 1 carbon to about 20 carbons or equivalent length of other chemistries, but preferably below 10 carbons or 10 carbon equivalent length.

Successful treatment with the editing oligonucleotide in the chemical modification mode results in some proportion of the "target nucleic acid" becoming modified. In FIG. 19 the "chemical modification" (triangle) represents an addition of chemical moiety (e.g. a methyl group), but the modification as described herein can be one of a variety of additions or removals of chemical groups from the targeted nucleobase of the target nucleic acid sequence (e.g. deamination).

Mutations in a nucleic acid sequence resulting from a change in a single nucleotide may be transitions or transversions. Transitions arise when a point mutation changes a purine nucleotide to another purine nucleotide such as adenosine to guanosine or a pyrimidine nucleotide to another pyrimidine nucleotide such as cytidine to thymidine. Transitions can be caused by oxidative deamination, tautomerization and action of alkylating reagents. Transversions occur when a purine nucleotide is converted to a pyrimidine nucleotide or pyrimidine nucleotide to a purine nucleotide such as for example cytidine to adenosine and guanosine to thymidine. Transversions can be caused by ionizing radiation and action of alkylating reagents.

The present invention provides editing oligonucleotides that can reduce or eliminate the effects resulting from a variety of mutations. For example, if the mutation is a transition mutation, potential editing functions may include: A to G-like conversions that may be achieved by nitric oxide mediated deamination of adenine base at position 6 resulting in a formation of inosine which preferably pairs with cytosine; G to A-like conversions that may be achieved by O6-alkylation of guanine base resulting in O6-alkylguanine, which preferably pairs with uracil or thymine bases; C to T-like conversions that may be achieved by nitric oxide mediated or bisulfite mediated deamination of a cytosine base at position 4 resulting in a formation of uracil which pairs with adenine base; and T or U to C-like conversions that may be achieved by O4-alkylation of thymine or uracil base resulting in 4-alkylthymine or 4-alkyluracil bases, which preferably pair with guanine base.

If the mutation is a transversion mutation, potential editing functions may include: A to C-like conversions is a reaction with benzo[a]pyrene to produce adducts of adenine base resulting in a N6-Benzo[a]pyrene diol epoxide (BPDE) adduct of adenine that is bypassed by T7 RNA polymerase, directing the misincorporation of G opposite modified adenine with high probability; A to T-like conversions is a reaction with benzo[a]pyrene to produce adducts of adenine base resulting in the N6-Benzo[a]pyrene diol epoxide (BPDE) adduct of adenine that is bypassed by T7 RNA polymerase, directing the misincorporation of A opposite modified adenine with high probability; and G to T-like conversions may be performed by oxidation of G to 8-oxo-G which leads to ~50% incorporation by RNA polymerase of A into RNA strand opposite 8-oxo-G modification.

E. Chemistries

The editing oligonucleotides employing the chemical modification mode of the present invention perform their function by a variety of specific chemical reactions including, alkylation and deamination. In each type of reaction, optional reactive groups may be utilized to increase specificity (Singh, et al. The resurgence of covalent drugs Nature Reviews: Drug Discovery Volume 10 Apr. 2011), avoid reactivity during synthesis, purification and storage, and prior to reaching the target cell, may be released by pH, such as low pH in endosome or lysosome, intracellular esterases, temperature, light or the reducing environment of the cell.

F. Editing Action

The present invention provides editing oligonucleotides that can reduce or eliminate the effects resulting from a variety of mutations.

In one embodiment of the present invention a common mutated sequence causing Cystic Fibrosis in Western populations, deltaF508 may be corrected. The repair of a deletion mutation like detalF508 could be achieved by inserting back the deleted 3 nucleotides with the editing oligonucleotide. McNeer, N. A. et al., (Nature Comm. DOI:10.1038/ncomms 7952 pgs. 1-11, 2015) provides an example with editing oligonucleotides with three phosphorothioate modifications on each end. Oligonucleotides with the improved chemical modification patterns and configurations of editing oligonucleotides of the present invention targeting the same region can be substituted for the editing oligonucleotides with three phosphorothioate modifications on each end similar to that used by McNeer et al. However, single base transitions or transversions may be more efficiently achieved with editing, compared to insertions, therefore a change from R 553 to M (R553M) in the CF protein coding sequence which suppresses the deleterious effects of the deltaF508 mutation is an alternative approach to correcting the phenotypic effect of the this mutation (X. Liul et al. Biochemistry 51(25):5113-5124, 2012. doi:10.1021/bi300018e. This is the first application of therapeutic editing to create suppressor mutations of deltaF508.

Another change in the CF protein coding sequence, from R 555 to K (R555K), suppresses the deleterious effects of the deltaF508 mutation (X. Liul et al. supra).

Another aspect of the present invention includes administering an editing oligonucleotide to an individual in order to create an allele sequence in their DNA or RNA that is protective for one or more diseases. For example, inducing a change from the common allele of the APP protein, to the Alzheimer's protective allele sequence of APP at the DNA level in the brain will lead to the individual being resistant to the development of Alzheimer's (Jonsson, T. et al. Nature, 488(7409):96-9, 2012. PubMed and Kero, M. et al. Neurobiol Aging, 34(5):1518, 2013). A preferred allele sequence is the Ala673Thr allele which has a lifetime protective effect of ~80% for Alzheimer's disease. This change can be made, for example, by changing a codon at this position, GCA, to ACA.

Another example of creating a protective allele to reduce the risk of and/or slow the progression of Alzheimer's disease is editing a change in the nucleic acid sequence encoding Arg112 to Cys112 in APOE to convert the Alzheimer's risk alleles APOE4 to the APOE3 alleles. This change can be done optionally in conjunction with a change from Arg158 to Cys158, which would change the Alzheimer's risk allele APOE4 to the protective Allele APOE2. The dual change could be accomplished with a single long editing strand, or two separate smaller editing oligonucleotides. A single change from Arg158 to Cys158 would convert APOE3 to the more protective allele APOE2. See exemplary editing oligo sequences in FIG. 24.

Another example of creating a protective allele is the inactivation of PCSK9 in the liver, by creating a premature stop codon, or one of myriad of modifications that will inactivate or reduce the activity of PCSK9. Naturally occurring null mutant alleles in PCSK9 have a protective lifetime affect up to 90% against arteriosclerosis-based diseases such as occlusive stroke and coronary artery disease. Furthermore, therapeutic antibodies which neutralize the function PCSK9 reduce serum cholesterol levels. These antibodies are expensive and would have to be administered chronically, whereas editing at the DNA level would result in a permanent reduction in serum cholesterol levels. One nonobvious advantage of using editing oligonucleotides to create protective alleles as opposed to repairing mutated alleles, is that the target sequences for protective editing are much more homogeneous sequences within the population, whereas many human disease causing mutations are heterogeneous within the population, and would thus require a panel of different editing oligonucleotides to be available to treat the patients with the varied genotypes.

III. TREATMENTS

A. Diseases

The editing oligonucleotides of the present invention may be utilized to reduce, decrease or eliminate the effects of a disease. Diseases that may be treated with the editing oligonucleotide of the present invention include: adenosine deaminase deficiency; alpha-1 antitrypsin deficiency; Alzheimer's; aminoacylase 2 deficiency; aspartoacylase deficiency; arteriosclerosis, atherosclerosis, Canavan-Van Bogaert-Bertrand disease; Charcot-Marie-Tooth disease; cystic fibrosis; breast cancer predisposition mutations; diabetes Type caused by insulin receptor mutations; diabetes type 2 (e.g. target gene PTP-1B and ABCA1 C69T allele (Alharbi et al., J. Biosci. 38(5):893-897 (2013)), drepanocytosis; Fabry disease; familial adenomatous polyposis; familial amyloid cardiomyopathy; familial amyloid polyneuropathy; familial dysautonomia; familial hypercholesterolemia; Friedreich's ataxia; Gaucher disease type I; Gaucher disease type II; glycogen storage disease type II; GM2 gangliosidosis; hemochromatosis; hemophilia A; hemophilia B; hemophilia C; hereditary blindness (see Andrieu-Soler Molecular Vision 13:692-706, 2007, for an example of delivery of editing oligonucleotides correcting a mutation in rd1 to the retina); hereditary tyrosinemia type I (HTI) (caused by mutations in fumarylacetoacetate hydrolase (FAH) Yin, et al. Nature biotechnology 32 (6), 2014) hexosaminidase A deficiency; hypercholesterolemia, ovarian cancer predisposition mutations; phenylketonuria;

polycystic kidney disease; prion disease; senile systemic amyloidosis; sickle-cell disease; sickle-cell anaemia; Smith-Lemli-Opitz syndrome; spinal muscular atrophy; and Wilson's disease.

Specific disease targets include: cystic fibrosis transmembrane conductance regulator gene (CFTR); dystrophin gene (DMD); amyloid beta (A4) precursor protein gene (APP); Factor XII gene; Factor IX gene; Factor XI gene; HgbS; insulin receptor gene; adenosine deaminase gene; alpha-1 antitrypsin gene; breast cancer 1 gene (BRCA1); breast cancer 2 gene (BRCA2); aspartocyclase gene (ASPA); galactosidase alpha gene (GLA); adenomatous polyposis coli gene (APC); inhibitor of kappa light polypeptide gene enhancer in B-cells, kinase complex-associated protein (IKBKAP); glucosidase beta acid gene (GBA); glucosidase alpha acid gene (GAA); hemochromatosis gene (HFE); apolipoprotein B gene (APOB); low density lipoprotein receptor gene (LDLR), low density lipoprotein receptor adaptor protein 1 gene (LDLRAP1); proprotein convertase subtilisin/kexin type 9 gene (PCSK9); polycystic kidney disease 1 (autosomal dominant) gene (PKD-1); Prion protein gene (PRNP); PTP-1B; 7-dehydrocholesterol reductase gene (DHCR7); survival of motor neuron 1, telomeric gene (SMN1); biquitin-like modifier activating enzyme 1 gene (UBA1); dynein, cytoplasmic 1, heavy chain 1 gene (DYNC1H1), survival of motor neuron 2, centromeric gene (SMN2); (vesicle-associated membrane protein)-associated protein B and C (VAPB); hexosaminidase A (alpha polypeptide) gene (HEXA); transthyretin gene (TTR); ATPase, Cu++ transporting, beta polypeptide gene (ATP7B); phenylalanine hydroxylase gene (PAH); rhodopsin gene; retinitis pigmentosa 1 (autosomal dominant) gene (RP1); retinitis pigmentosa 2 (X-linked recessive) gene (RP2) and other known gene targets.

Editing oligonucleotide may be utilized to ameliorate disease symptoms when the mutation is a missense mutation such as sickle-cell disease (SCD), sickle-cell anaemia (SCA) or drepanocytosis, nonsense mutation such as in Duchenne muscular dystrophy and Becker muscular dystrophy, a spicing mutation such as in familial dysautonomia, to create a protection allele such as in Type 2 diabetes (e.g., target gene PTP-1B), Alzheimer's disease (APP) and familial hypercholesterolemia (PCSK9), or to create an intragenic suppressor such as cystic fibrosis delta 508 mutation. Other missense or nonsense mutations include adenosine deaminase deficiency, alpha-1 antitrypsin deficiency, aminoacylase 2 deficiency, amyloid diseases, aspartoacylase deficiency, breast cancer predisposition mutations, Canavan-Van Bogaert-Bertrand disease, Charcot-Marie-Tooth disease, cystic fibrosis, diabetes Type 1 (caused by insulin receptor mutations), Fabry disease, familial adenomatous polyposis, familial amyloid cardiomyopathy, familial amyloid polyneuropathy, Friedreich's ataxia, Gaucher disease type I, Gaucher disease II, glycogen storage disease type II, GM2 gangliosidosis, hemochromatosis, hemophilia A, hemophilia B, hemophilia C, hexosaminidase A deficiency, ovarian cancer predisposition mutations, phenylketonuria, polycystic kidney disease, prion disease, senile systemic amyloidosis, Smith-Lemli-Opitz syndrome, spinal muscular atrophy, Wilson's disease, and hereditary blindness.

Additional examples of diseases and disorders that can be treated with the oligonucleotides of the invention, and methods of using said oligonucleotides, are disclosed in FIG. 23.

Non-limiting examples of editing oligonucleotides which target genes associated with representative diseases and disorders are disclosed in FIG. 24.

B. Pharmaceutical Compositions

The pharmaceutical compositions of the invention are administered in dosages sufficient to effect the expression of the target gene. In general, a suitable dose of editing oligonucleotide will be in the range of 0.01 to 5.0 milligrams per kilogram body weight of the recipient per day, or up to 50 milligrams per kilogram if necessary, preferably in the range of 0.1 to 200 micrograms per kilogram body weight per day, more preferably in the range of 0.1 to 100 micrograms per kilogram body weight per day, even more preferably in the range of 1.0 to 50 micrograms per kilogram body weight per day, and most preferably in the range of 1.0 to 25 micrograms per kilogram body weight per day. The pharmaceutical composition may be administered once daily, or the editing oligonucleotide may be administered as two, three, four, five, six or more sub-doses at appropriate intervals throughout the day or even using continuous infusion. In that case, the editing oligonucleotide contained in each sub-dose must be correspondingly smaller in order to achieve the total daily dosage. The dosage unit can also be compounded for delivery over several days, e.g., using a conventional sustained release formulation which provides sustained release of the editing oligonucleotide over a several day period. Sustained release formulations are well known in the art. In this embodiment, the dosage unit contains a corresponding multiple of the daily dose.

i. Dosages

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual editing oligonucleotide encompassed by the invention can be made using conventional methodologies or on the basis of in vivo testing using an appropriate animal model, as described elsewhere herein.

ii. Routes of Administration

The pharmaceutical compositions encompassed by the invention may be administered by any means known in the art including, but not limited to oral or parenteral routes, including intravenous, intramuscular, intraperitoneal, subcutaneous, transdermal, airway (aerosol), rectal, vaginal and topical (including buccal and sublingual) administration. In preferred embodiments, the pharmaceutical compositions are administered intravenously.

For intramuscular, subcutaneous and intravenous use, the pharmaceutical compositions of the invention will generally be provided in sterile aqueous solutions or suspensions, buffered to an appropriate pH and isotonicity. Suitable aqueous vehicles include Ringer's solution and isotonic sodium chloride. In a preferred embodiment, the carrier consists exclusively of an aqueous buffer. In this context, "exclusively" means no auxiliary agents or encapsulating substances are present which might affect or mediate uptake of the editing oligonucleotide in the cells that express the target gene. Such substances include, for example, micellar structures, such as liposomes or capsids, as described below. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The pharmaceutical compositions useful according to the invention also include encapsulated formulations to protect the editing oligonucleotide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Johnson & Johnson, Inc. (New Brunswick, NJ) and Nova Pharmaceuticals, Inc. (Bella Vista, Australia) Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811; PCT application no. WO 91/06309; and European patent publication EP-A-43075 or obtained commercially from Northern Lipids (Burnaby, British Columbia), Avanti Polar Lipids (Alabaster, Alabama) or Arbutus BioPharma (Burnaby, British Columbia). Nanoparticle delivery may also be used and are described in J. Zhou et al. *Pharmaceuticals*, 6:85-107, 2013; doi:10.3390/ph6010085, McNeer et al., Gene Ther. 20(6):658-669, 2013; doi: 10.1038/gt.2012.82, McNeer et al., Nature Comm. DOI: 10.1038/ncomms 7952 pgs. 1-11, 2015 and Yuen Y. C. et al. *Pharmaceuticals,* 5:498-507, 2013; doi:10.3390/pharmaceutics5030498.

iii. Toxicity and Efficacy

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred.

The data obtained from cell culture assays and animal studies can be used in formulation a range of dosage for use in humans. The dosage of compositions of the invention lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

IV. COMPOSITIONS AND METHODS

The oligonucleotides of the invention are provided in the following compositions and methods.

In one aspect, provided herein is a method of modifying a nucleic acid sequence within an isolated cell or cells within an organism comprising the step of introducing the oligonucleotide into said cells such that a modification or modifications of the complementary cellular nucleic results, wherein said modification creates an allele that protects against disease, repairs a mutation, or knocks out a gene.

In another embodiment, the allele that protects against disease does not inactivate the function of the targeted gene, but does modulate the function of the targeted gene.

In yet another embodiment, the method results in the modulation of the function of the targeted gene. The modulation of the function of the targeted gene may increase the activity or expression the gene product. The modulation of the function of the targeted gene may partially decrease the activity or expression of the post-translationally processed gene product.

The modulation of the function of the targeted gene may partially decreases the activity or expression of the post-translationally processed gene product by not more than 50 percent in a modified cell The modulation of the function of the targeted gene may partially decrease the activity or expression of the post-translationally processed gene product by not more than 75 percent in a modified cell. The modulation of the function of the targeted gene may partially decrease the activity or expression of the post-translationally processed gene product by not more than 90 percent in a modified cell.

In certain embodiments of the method, the targeted gene product is a protein post-translationally modified by protease cleavage. In a particular embodiment, the targeted gene protein is APP and the modification of the gene changes the sequence of APP to make it less susceptible to cleavage by the beta-secretase. The sequence encoding position 673 in APP may be changed from Alanine to Threonine.

In another aspect provided herein are compositions comprising oligonucleotides of the invention. The compositions may be used in the methods described herein. In some embodiments, the oligonucleotide is present in a formulation (e.g., an editing oligonucleotide formulation). In one embodiment, the editing oligonucleotide formulation comprises an exogenous protein or ribonucleoprotein (or nucleic acids that express said protein or ribonucleoprotein) that increase the editing efficiency. The exogenous protein or ribonucleoprotein that increases the editing efficiency may be a programmable nuclease. The exogenous protein or ribonucleoprotein that increases the editing efficiency may be a CRISPR-Cas9, Zinc Finger, or Talen programmable nuclease. The editing oligonucleotide may be a single-stranded unmodified DNA. The editing oligonucleotide may be single-stranded and contain at least 10 deoxyribose sugars. The editing oligonucleotide may be chemically modified.

The chemical modifications of the editing oligonucleotide may include phosphorothiotes. The chemical modifications of the editing oligonucleotide may include 3 phosphorothioate internucleotide linkages at each terminus. The chemical modifications of the editing oligonucleotide may include a total of 1-5 phosphorothioate internucleotide linkages at the termini. The chemical modifications of the editing oligonucleotide may include a total of 7 or more phosphorothioate internucleotide linkages. In one embodiment, the chemical modifications of the editing oligonucleotide include a total of 7 or more phosphorothioate internucleotide linkages, but there remains at least 10 internucleotide linkages that are not phosphorothioate modified. In one embodiment, the modifications do not contain any phosphorothioate modifications. In one embodiment, the modifications include exonucleases end-blocking groups that are not phosphorothioates.

In certain embodiments, the compositions comprise oligonucleotides having chemically modified nucleobases. The chemically modified nucleobase(s) can be 5 methyl deoxycytidine. In some embodiments, there is 1 to about 500 5 methyl deoxycytidines. In other embodiments, there is 1 to about 50 5 methyl deoxycytidines. In other embodiments, there is 1 to about 10 5 methyl deoxycytidines. In other embodiments, there is 1 to about 5 5 methyl deoxycytidines. In other embodiments, there is 1 to about 5 5 methyl deoxycytidines. In other embodiments, there is one 5 methyl deoxycytidine. In other embodiments, one of the 5 methyl deoxycytidines is in a 5'CpG sequence hybridized to a mismatched 5'TG. In a particular embodiment, this 5'TG target site is the TG of a methionine start codon, and the edit reduces or eliminates production of functional target protein.

In a particular embodiment of the methods and compositions described herein, the editing oligonucleotides comprise 2' modifications. In another particular embodiment of the methods and compositions described herein, the editing oligonucleotides comprise only 2' modifications. In a particular embodiment, the editing oligonucleotides comprise 2'F 5' of editing site, and 2'-O-mt 3' of editing site, or both. In another particular embodiment, the editing oligonucleotides comprise modified bases that increase affinity near the editing site, wherein said modified bases are not 5 methyl C.

In a particular embodiment of the methods and compositions described herein, the oligonucleotides are encapsulated in delivery vehicles (see Yin et al. Nature Reviews, Genetics. 15:541-555 (2014) for a description of delivery vehicles for nucleic acids).

In a particular embodiment of the methods and compositions described herein, the oligonucleotides further comprise a conjugated molecule that confers enhanced cell uptake.

In a particular embodiment of the methods and compositions described herein, the methods and compositions further comprise helper oligonucleotides.

In one aspect, provided herein is an editing oligonucleotide, wherein said editing oligonucleotide can edit a complementary target sequence within a cell, and wherein the editing oligonucleotide comprises one or more backbone modifications selected from the modifications listed in FIG. 20.

In one embodiment of the editing oligonucleotide, the backbone modification is neutral. The backbone modification can comprise 1 to about 20 neutral modifications. In a particular embodiment, the backbone modification comprises 2 to about 4 neutral modifications.

In another embodiment, the backbone modification is a methylphosphonate. The backbone modification may comprise 1 to about 20 methylphosphonates. In a particular embodiment, the backbone modification comprises 2-4 methylphosphonates. In a particular embodiment, the backbone modification comprises 2 methylphosphonates. In a more particular embodiment, the backbone modification comprises 2 methylphosphonates on the 5' termini.

In another embodiment, the editing oligonucleotide may comprise 1 to about 20 backbone modifications in a single modified backbone editing oligonucleotide. In one embodiment, at least two of the modifications are in a terminal segment. In a particular embodiment, the editing oligonucleotide comprises two modifications at the 5' termini.

In another aspect, provided herein is a method of using an editing oligonucleotides as described herein to edit a gene in cell or organism. In one embodiment, the cell is an isolated human cell. In one embodiment, the organism is a human. In certain embodiments, the method is used to treat an indication selected from the indications listed in FIG. 23. In a particular embodiment, the indication is selected from the indications listed in FIG. 24.

In one embodiment, the gene is a target gene listed in FIG. 24. In a particular embodiment, the editing oligonucleotide comprises at least 25 percent of a sequence listed in FIG. 24. In another particular embodiment, the editing oligonucleotide comprises at least 51 percent of a sequence from FIG. 24.

In another aspect, provided herein is an editing oligonucleotide, wherein said editing oligonucleotide can edit a complementary target sequence within a cell, and wherein said editing oligonucleotide comprises one or more backbone nucleobase modifications listed in FIG. 21. In one embodiment, the editing oligonucleotide comprises 1 to about 100 modified nucleobases from FIG. 21. In one embodiment, the editing oligonucleotide comprises 1 to about 30 modified nucleobases from FIG. 21. In one embodiment, the editing oligonucleotide comprises 1 to about 10 modified nucleobases from FIG. 21. In a particular embodiment, the editing oligonucleotide comprises one or more modified nucleobases according to a modification pattern species in Table 1.

In another embodiment of the editing oligonucleotide, the modified nucleobases decrease immune stimulation by editing oligonucleotide in mammals. In a particular embodiment, the modified nucleobase comprises a 5' methyl C chemical modification. In another particular embodiment, the nucleobase modification increases the affinity of the editing oligonucleotide for its complimentary target.

In another aspect, provided herein is an editing oligonucleotide, wherein said editing oligonucleotide can edit a complementary target sequence within a cell, and wherein the editing oligonucleotide comprises one or more sugar modifications listed in FIG. 22. In one embodiment, the sugar modifications are selected from 2' sugar modifications. A 2' sugar modification can be 2' F. A 2' sugar modification may be 2' O-methyl. The 2' sugar modifications can be a combination of 2' F and 2' O-methyl modifications.

In one embodiment of the editing oligonucleotide, the majority (e.g., greater than 50%) of the 2' F modifications are 3' of the editing site. In another embodiment of the editing oligonucleotide, the majority (e.g., greater than 50%) of the 2' O-methyl modifications are 5' of the editing site.

The 2' sugar modification can increase the affinity of oligonucleotide for its target nucleic acids. In one embodiment the editing oligonucleotide comprises 1-75 sugar modifications. In another embodiment the editing oligonucleotide comprises 2-30 sugar modifications. In another embodiment the editing oligonucleotide comprises 2-16 sugar modifications.

In one embodiment, the editing oligonucleotide comprises about 5-100% chemically modified bases. In another embodiment the editing oligonucleotide comprises about 25-75% chemically modified bases. In another embodiment the editing oligonucleotide comprises about 40-60% chemically modified bases. In a particular embodiment, the editing oligonucleotide comprises 2 modifications. In one particular embodiment, the editing oligonucleotide contains 2'F and 2'O-methyl modifications.

In one embodiment, the editing oligonucleotide targets a gene listed in FIG. 24.

In another aspect, provided herein is a method of treating a human disease by genome editing comprising the step of administering to a person in need of such treatment an editing oligonucleotide as described herein.

In yet another aspect, provided herein is an editing oligonucleotide comprises one or more delivery conjugates. In a particular embodiment, the editing oligonucleotide comprises one delivery conjugate. The delivery conjugate can promote cellular uptake of the oligonucleotide. The delivery conjugate can enhance uptake of the oligonucleotide into cells in an organism. The delivery conjugate can be a chemical moiety that is either directly or indirectly covalently bonded to a nucleotide in the editing oligonucleotide. Direct covalent bonding involves, for example, covalent bonding of the chemical moiety to the oligonucleotide. Indirect covalent bonding involves, for example, the use of a linker that is covalently bonded to both the oligonucleotide and the chemical moiety. In one embodiment, the editing oligonucleotide is not encapsulated by a delivery vehicle that enhances uptake in cells in an organism.

In one embodiment, the delivery conjugate is a ligand for a receptor. In a particular embodiment, the ligand is one to ten Gal-Nacs. In another particular embodiment, the ligand is three Gal-Nacs. In one embodiment, the delivery conjugate is a lipophilic group. The lipophilic group may have about 10 to about 50 carbons. The lipophilic group may be a form of cholesterol.

Editing oligonucleotides comprising one or more delivery conjugates are useful for the treatment of disease. In one aspect, provided herein is a method of treating or preventing a human disease by administering to a patient in need of such treatment an editing oligonucleotide comprising one or more delivery conjugates, as described herein. In one embodiment, the method targets a gene for editing, wherein the targeted gene is listed in FIG. 23. In another embodiment, the targeted gene for the treatment is listed in FIG. 24. In one embodiment of the method, the editing oligonucleotide sequence comprises one of the sequences in FIG. 24.

V. RESULTS

The oligonucleotide constructions presented in Table 1 are useful for research and therapeutic applications, even though their activity in cell culture may be less than the parent compound, because each of these oligonucleotides adds chemistries, contributes to other projected therapeutic benefits, such as reduced immune stimulation, higher nuclease stability, higher target specificity, reduced chemical toxicity and/or higher affinity.

TABLE 1

Editing Oligonucleotide constructions

```
ETAGEN Serial Number 100001 (SEQ ID NO. 1)
SEQUENCE 5':
CATGTGGTCGGGGTAGCGGCTGAAGCACTGCACGCCGTAGGTCAGGGTGGTCACGAGGGTGGGCCAGGGCAC
Sugar:
DDDDDDDDDDDDDDDDDDDDDDDDDDDDDDDDDDDDDDDDDDDDDDDDDDDDDDDDDDDDDDDDDDDDDDDD
Backbone:
SSSOOOOOOOOOOOOOOOOOOOOOOOOOOOOOOOOOOOOOOOOOOOOOOOOOOOOOOOOOOOOOOOOOOSSS
Length: 72
Base Modification: 3 phosphorothioates end-blocks on each terminus
Wild Type
% Editing Efficiency: 0.58 +/- 0.09

ETAGEN Serial Number 100002 (SEQ ID NO. 2)
SEQUENCE 5':
CATGTGGTCGGGGTAGCGGCTGAAGCACTGCACGCCCTAGGTCAGGGTGGTCACGAGGGTGGGCCAGGGCAC
Sugar:
DDDDDDDDDDDDDDDDDDDDDDDDDDDDDDDDDDDDDDDDDDDDDDDDDDDDDDDDDDDDDDDDDDDDDDDD
Backbone:
SSSOOOOOOOOOOOOOOOOOOOOOOOOOOOOOOOOOOOOOOOOOOOOOOOOOOOOOOOOOOOOOOOOOOSSS
Length: 72
Base Modification: 3 phosphorothioates end-blocks on each terminus
Wild Type
% Editing Efficiency: 0.00 +/- 0.00

ETAGEN Serial Number 100003 (SEQ ID NO. 3)
SEQUENCE 5':
CGGCTGAAGCACTGCACGCCGTAGGTCAGGGTGGTCACGA
Sugar:
DDDDDDDDDDDDDDDDDDDDDDDDDDDDDDDDDDDDDDDD
Backbone:
OOOOOOOOOOOOOOOOOOOOOOOOOOOOOOOOOOOOOOOO
Length: 40
Base Modification: DNA with no modifications
Wild Type
% Editing Efficiency: 0.03 +/- 0.00

ETAGEN Serial Number 100004 (SEQ ID NO. 4)
SEQUENCE 5':
CGGCTGAAGCACTGCACGCCCTAGGTCAGGGTGGTCACGA
Sugar:
DDDDDDDDDDDDDDDDDDDDDDDDDDDDDDDDDDDDDDDD
Backbone:
OOOOOOOOOOOOOOOOOOOOOOOOOOOOOOOOOOOOOOOO
Length: 40
Base Modification: DNA with no modifications
Mutant
% Editing Efficiency: 0.03 +/- 0.01

ETAGEN Serial Number 100005 (SEQ ID NO. 5)
```

TABLE 1-continued

Editing Oligonucleotide constructions

SEQUENCE 5':
CGGCTGAAGCACTGCACGCCGTAGGTCAGGGTGGTCACGA
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: 3 phosphorothioates end-blocks on each terminus (Parent)
Wild Type
% Editing Efficiency: 1.69 +/- 0.63

ETAGEN Serial Number 100006 (SEQ ID NO. 6)
SEQUENCE 5':
CGGCTGAAGCACTGCACGCCCTAGGTCAGGGTGGTCACGA
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: 3 phosphorothioates end-blocks on each terminus
Mutant
% Editing Efficiency: 0.00 +/- 0.00

ETAGEN Serial Number 100007 (SEQ ID No. 7)
SEQUENCE 5':
CGGCTGAAGCACTGCACGCCGTAGGTCAGGGTGGTCACGA
Sugar:
DDDDDDDDDDDDDDDDDDDDDDDDDDDDDDDDDDDDDDDD
Backbone:
SSSSSSSSOOOOOOOOOOOOOOOOOOOOOSSSSSSSSSSS
Length: 40
Base Modification: ~ half phosphorothioates positive 40 mer (9s-20o-10s) with unmodified editing region
Wild Type
% Editing Efficiency: 0.01 +/- 0.01

ETAGEN Serial Number 100008 (SEQ ID NO. 8)
SEQUENCE 5':
CGGCTGAAGCACTGCACGCCCTAGGTCAGGGTGGTCACGA
Sugar:
DDDDDDDDDDDDDDDDDDDDDDDDDDDDDDDDDDDDDDDD
Backbone:
SSSSSSSSOOOOOOOOOOOOOOOOOOOOOSSSSSSSSSSS
Length: 40
Base Modification: ~ half phosphorothioates positive 40 mer (9s-20o-10s) with unmodified editing region
Mutant
% Editing Efficiency: 0.11 +/- 0.01

ETAGEN Serial Number 100009 (SEQ ID NO. 9)
SEQUENCE 5':
CTGCGAGATCGCGGCAGCGCCATGCTGAGGCTCGTACAGA
Sugar:
DDDDDDDDDDDDDDDDDDDDDDDDDDDDDDDDDDDDDDDD
Backbone:
SSSSSSSSOOOOOOOOOOOOOOOOOOOOOSSSSSSSSSSS
Length: 40
Base Modification: ~ half phosphorothioates positive 40 mer (9s-20o-10s) with unmodified editing region
Scrambled
% Editing Efficiency: 0.01 +/- 0.01

ETAGEN Serial Number 100010 (SEQ ID NO. 10)
SEQUENCE 5':
CGGCTGAAGCACTGCACGCCGTAGGTCAGGGTGGTCACGA
Sugar:
DDDDDDDDDDDDDDDDDDDDDDDDDDDDDDDDDDDDDDDD
Backbone:
SSSSSSSSSSSSSSSSOOOOOOOSSSSSSSSSSSSSSSSS
Length: 40
Base Modification: Majority phosphorothiotes except in editing region (16s-6o-17s)
Wild Type
% Editing Efficiency: 0.00 +/- 0.00

ETAGEN Serial Number 100011 (SEQ ID NO. 11)
SEQUENCE 5':
CGGCTGAAGCACTGCACGCCCTAGGTCAGGGTGGTCACGA

TABLE 1-continued

Editing Oligonucleotide constructions

Sugar:
DDDDDDDDDDDDDDDDDDDDDDDDDDDDDDDDDDDDDDDD
Backbone:
SSSSSSSSSSSSSSSSOOOOOOSSSSSSSSSSSSSSSSSS
Length: 40
Base Modification: Majority phosphorothiotes except in editing region (16s-6o-17s)
Mutant
% Editing Efficiency: 0.01 +/- 0.00

ETAGEN Serial Number 100012 (SEQ ID NO. 12)
SEQUENCE 5':
CTGCGAGATCGCGGCAGCGCCATGCTGAGGCTCGTACAGA
Sugar:
DDDDDDDDDDDDDDDDDDDDDDDDDDDDDDDDDDDDDDDD
Backbone
SSSSSSSSSSSSSSSSOOOOOOSSSSSSSSSSSSSSSSSS
Length: 40
Base Modification: Majority phosphorothiotes except in editing region (16s-6o-17s)
Scrambled
% Editing Efficiency: 0.03 +/- 0.01

ETAGEN Serial Number 100013 (SEQ ID NO. 13)
SEQUENCE 5':
CGGCTGAAGCACTGCACGCCGTAGGTCAGGGTGGTCACGA
Sugar:
DDDDDDDDDDDDDDDDDDDDDDDDDDDDDFFFFFFFFDDD
Backbone:
SSSOOOOOOOOOOOOOOOOOOOOOOOOOOOOOOOOOOSSS
Length: 40
Base Modification: 3' 8 x 2'F high affinity arms with s end-blocks
Wild Type
% Editing Efficiency: 1.16 +/- 0.11

ETAGEN Serial Number 100014 (SEQ ID NO. 14)
SEQUENCE 5':
CGGCTGAAGCACTGCACGCCCTAGGTCAGGGTGGTCACGA
Sugar:
DDDDDDDDDDDDDDDDDDDDDDDDDDDDDFFFFFFFFDDD
Backbone:
SSSOOOOOOOOOOOOOOOOOOOOOOOOOOOOOOOOOOSSS
Length: 40
Base Modification: 3' 8 x 2'F high affinity arms with s end-blocks
Mutant
% Editing Efficiency: 0.01 +/- 0.00

ETAGEN Serial Number 100015 (SEQ ID NO. 15)
SEQUENCE 5':
TTCGGCTGAAGCACTGCACGCCGTAGGTCAGGGTGGTCACGA
Sugar:
DDDDDDDDDDDDDDDDDDDDDDDDDDDDDDDDDDDDDDDDDD
Backbone:
MMOOOOOOOOOOOOOOOOOOOOOOOOOOOOOOOOOOOOOSSS
Length: 42
Base Modification: 5' non-phosphorothioate end-block (methyphosphonate), 3' 3s end-blocks
Wild Type
% Editing Efficiency: 0.90 +/- 0.17

ETAGEN Serial Number 100016 (SEQ ID NO. 16)
SEQUENCE 5':
TTCGGCTGAAGCACTGCACGCCCTAGGTCAGGGTGGTCACGA
Sugar:
DDDDDDDDDDDDDDDDDDDDDDDDDDDDDDDDDDDDDDDDDD
Backbone:
SSSOOOOOOOOOOOOOOOOOOOOOOOOOOOOOOOOOOOSSS
Length: 42
Base Modification: 5' non-phosphorothioate end-block (methyphosphonate), 3' 3s end-blocks
Mutant
% Editing Efficiency: 0.00 +/- 0.00

ETAGEN Serial Number 100017 (SEQ ID NO. 17)
SEQUENCE 5':
    M     M M  M M MM     M        M
CGGCTGAAGCACTGCACGCCGTAGGTCAGGGTGGTCACGA
Sugar:

TABLE 1-continued

Editing Oligonucleotide constructions

```
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: C's replaced with 5' methyl C to fool repair machinery, as
to which strand is nascent
Wild Type
% Editing Efficiency: 1.36 +/- 0.03

ETAGEN Serial Number 100018 (SEQ ID NO. 18)
SEQUENCE 5':
    M    M M  M M MMM    M         M
CGGCTGAAGCACTGCACGCCCTAGGTCAGGGTGGTCACGA
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: C's replaced with 5' methyl C to fool repair machinery, as
to which strand is nascent
Mutant
% Editing Efficiency: 0.00 +/- 0.00

ETAGEN Serial Number 100019 (SEQ ID NO. 19)
SEQUENCE 5':
AGUGCUUCAGCCG (all 2'-O-mt)
Sugar:
MMMMMMMMMMMMM
Backbone:
SSOOOOOOOOOSS
Length: 29
Base Modification: 2'-O-methyl "protector" oligo complimentary to positions
1-13 of editing oligo
Wild Type
% Editing Efficiency: ND +/-

ETAGEN Serial Number 100020 (SEQ ID NO. 20)
SEQUENCE 5':
GACCUACGGCGUGC
Sugar:
MMMMMMMMMMMMMM
Backbone:
SSOOOOOOOOOOSS
Length: 17
Base Modification: 2'-O-methyl "protector" oligo complimentary to positions
14-27 of editing oligo
Wild Type
% Editing Efficiency: ND +/-

ETAGEN Serial Number 100021 (SEQ ID NO. 21)
SEQUENCE 5':
UCGUGACCACCCU
Sugar:
MMMMMMMMMMMMM
Backbone:
SSOOOOOOOOOSS
Length: 16
Base Modification: 2'-O-methyl "protector" oligo complimentary to positions
28-40 of editing oligo
Wild Type
% Editing Efficiency: ND +/-

ETAGEN Serial Number 100022 (SEQ ID NO. 22)
SEQUENCE 5':
GCACTGCACGCCCTAGGTCAGGGTG
Sugar:
DDDDDDDDDDDDDDDDDDDDDDDDD
Backbone:
SSSSSSSSSSSSSSSSSSSSSSSSS
Length: 25
Base Modification: 25 mer all phosphorothioate DNA
Wild Type
% Editing Efficiency: ND +/-

ETAGEN Serial Number 100023 (SEQ ID NO. 23)
SEQUENCE 5':
GCACTGCACGCCGTAGGTCAGGGTG
Sugar:
```

TABLE 1-continued

Editing Oligonucleotide constructions

DDDDDDDDDDDDDDDDDDDDDDDDD
Backbone:
SSSSSSSSSSSSSSSSSSSSSSSSS
Length: 25
Base Modification: 25 mer all phosphorothioate DNA
Mutant
% Editing Efficiency: ND +/−

ETAGEN Serial Number 100024 (SEQ ID NO. 24)
SEQUENCE 5':
TCGCGGCAGCGCCATGCTGAGGATC
Sugar:
DDDDDDDDDDDDDDDDDDDDDDDDD
Backbone:
SSSSSSSSSSSSSSSSSSSSSSSSS
Length: 25
Base Modification: 25 mer all phosphorothioate DNA
Scrambled
% Editing Efficiency: ND +/−

ETAGEN Serial Number 100031 (SEQ ID NO. 25)
SEQUENCE 5':
CGGCTGAAGCACTGCACGCCGTAGGTCAGGGTGGTCACGA
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: 3 phosphorothioates end-blocks on each terminus (PARENT)
Wild Type
% Editing Efficiency: 2.07 +/− 0.46

ETAGEN Serial Number 100032 (SEQ ID NO. 26)
SEQUENCE 5'
CGGCTGAAGCACTGCACGCCCTAGGTCAGGGTGGTCACGA
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: 40 mers (with 3 phosphorothioates on each terminus)
Mutant
% Editing Efficiency: 0.04 +/− 0.01

ETAGEN Serial Number 100033 (SEQ ID NO. 27)
SEQUENCE 5':
CGGCTGAAGCACTGCACGCCCTAGGTCAGGGTGGTCACGA
Sugar:
DDDFFFFFFFFDDDDDDDDDDDDDDDDDDDDFFFFFFFFDDD
Backbone:
SSSOOOOOOOOOOOOOOOOOOOOOOOOOOOOOOOOOOSSS
Length: 40
Base Modification: 5' and 3' 8 x 2'F high affinity arms with s end-blocks
Mutant
% Editing Efficiency: 0.00 +/− 0.00

ETAGEN Serial Number 100034 (SEQ ID NO. 28)
SEQUENCE 5':
CGGCTGAAGCACTGCACGCCGTAGGTCAGGGTGGTCACGA
Sugar:
DDDFFFFFFFFDDDDDDDDDDDDDDDDDDDDFFFFFFFFDDD
Backbone
SSSOOOOOOOOOOOOOOOOOOOOOOOOOOOOOOOOOOSSS
Length: 40
Base Modification: 5' and 3' 8 x 2'F high affinity arms with s end-blocks
Wild Type
% Editing Efficiency: 0.25 +/− 0.04

ETAGEN Serial Number 100035 (SEQ ID NO. 29)
SEQUENCE 5':
CGGCTGAAGCACTGCACGCCGTAGGTCAGGGTGGTCACGA
Sugar:
DDDDDDDDDDDDDDDDDDDDDDDDDDDDDMMMMMMMMDDD
Backbone:
SSSOOOOOOOOOOOOOOOOOOOOOOOOOOOOOOOOOOSSS
Length: 40
Base Modification: 3' 8 x 2'-O-methyl high affinity arms with s end-blocks
Wild Type

TABLE 1-continued

Editing Oligonucleotide constructions

% Editing Efficiency: 0.06 +/- 0.03

ETAGEN Serial Number 100036 (SEQ ID NO. 30)
SEQUENCE 5':
CGGCTGAAGCACTGCACGCCCTAGGTCAGGGTGGTCACGA
Sugar:
DDDDDDDDDDDDDDDDDDDDDDDDDDDDDDDMMMMMMMMDDD
Backbone:
SSSOOOOOOOOOOOOOOOOOOOOOOOOOOOOOOOOOOSSS
Length: 40
Base Modification: 3' 8 x 2'-O-methyl high affinity arms with s end-blocks
Mutant
% Editing Efficiency: 0.00 +/- 0.00

ETAGEN Serial Number 100037 (SEQ ID NO. 31)
SEQUENCE 5':
CGGCTGAAGCACTGCACGCCGTAGGTCAGGGTGGTCACGA
Sugar:
DDDMMMMMMMMDDDDDDDDDDDDDDDDDDDDDDDDDDDDD
Backbone:
SSSOOOOOOOOOOOOOOOOOOOOOOOOOOOOOOOOOOSSS
Length: 40
Base Modification: 5' 8 x 2'-O-methyl high affinity arms with s end-blocks
Wild Type
% Editing Efficiency: 0.9 +/- 0.07

ETAGEN Serial Number 100038 (SEQ ID NO. 32)
SEQUENCE 5':
CGGCTGAAGCACTGCACGCCCTAGGTCAGGGTGGTCACGA
Sugar:
DDDMMMMMMMMDDDDDDDDDDDDDDDDDDDDDDDDDDDDD
Backbone:
SSSOOOOOOOOOOOOOOOOOOOOOOOOOOOOOOOOOOSSS
Length: 40
Base Modification: 5' 8 x 2'-O-methyl high affinity arms with s end-blocks
Mutant
% Editing Efficiency: 0.00 +/- 0.00

ETAGEN Serial Number 100039 (SEQ ID NO. 33)
SEQUENCE 5':
CGGCTGAAGCACTGCACGCCCTAGGTCAGGGTGGTCACGA
Sugar:
DDDMMMMMMMMDDDDDDDDDDDDDDDDDMMMMMMMMDDD
Backbone:
SSSOOOOOOOOOOOOOOOOOOOOOOOOOOOOOOOOOOSSS
Length: 40
Base Modification: 5' and 3' 8 x 2'-O-methyl high affinity arms with s end-blocks
Mutant
% Editing Efficiency: 0.00 +/- 0.00

ETAGEN Serial Number 100040 (SEQ ID NO. 34)
SEQUENCE 5':
CGGCTGAAGCACTGCACGCCGTAGGTCAGGGTGGTCACGA
Sugar:
DDDMMMMMMMMDDDDDDDDDDDDDDDMMMMMMMMDDD
Backbone:
SSSOOOOOOOOOOOOOOOOOOOOOOOOOOOOOOOOOOSSS
Length: 40
Base Modification: 5' and 3' 8 x 2'-O-methyl high affinity arms with s end-blocks
Wild Type
% Editing Efficiency: 0.03 +/- 0.02

ETAGEN Serial Number 100041 (SEQ ID NO. 35)
SEQUENCE 5':
        M   M M M MMM     M
CGGCTGAAGCACTGCACGCCCTAGGTCAGGGTGGTCACGA
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: Central C's replaced with 5' methyl C to fool repair machinery as to which strand is nascent
Mutant
% Editing Efficiency: 0.01 +/- 0.01

TABLE 1-continued

Editing Oligonucleotide constructions

ETAGEN Serial Number 100042 (SEQ ID NO. 36)
SEQUENCE 5':
CGGCTGAAGCACTGCACGCCGTAGGTCAGGGTGGTCACGA
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: Central C's replaced with 5' methyl C to fool repair
machinery as to which strand is nascent
Wild Type
% Editing Efficiency: 0.94 +/- 0.10

ETAGEN Serial Number 100043 (SEQ ID NO. 37)
SEQUENCE 5':
                M
CGGCTGAAGCACTGCACGCCGTAGGTCAGGGTGGTCACGA
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: Central C replaced with 5' methyl C to fool repair
machinery as to which strand is nascent
Wild Type
% Editing Efficiency: 1.27 +/- 0.36

ETAGEN Serial Number 100044 (SEQ ID NO. 38)
SEQUENCE 5':
                M
CGGCTGAAGCACTGCACGCCCTAGGTCAGGGTGGTCACGA
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: Central C replaced with 5' methyl C to fool repair
machinery as to which strand is nascent
Mutant
% Editing Efficiency: 0.02 +/- 0.01

ETAGEN Serial Number 100045 (SEQ ID NO. 39)
SEQUENCE 5':
        M M M    MM     M
TTCGGCTGAAGCACTGCACGCCGTAGGTCAGGGTGGTCACGATT
Sugar:
DDFFFFFFFFDDDDDDDDDDDDDDDDDDDDDDDFFFFFFFFDD
Backbone:
MMOOOOOOOOOOOOOOOOOOOOOOOOOOOOOOOOOOOOOOOOMM
Length: 44
Base Modification: Phosphorothiote-free methylphosphonoate end-blocks, 5
methyl C's and 2'F arms
Wild Type
% Editing Efficiency: ND +/-

ETAGEN Serial Number 100047 (SEQ ID NO. 40)
SEQUENCE 5':
  M M    M M  M M MM    M
TTCGGCTGAAGCACTGCACGCCGTAGGTCAGGGTGGTCACGA
Sugar:
DDDDDDDDDDDDDDDDDDDDDDDDDDDDDDDFFFFFFFFDDDD
Backbone:
MMOOOOOOOOOOOOOOOOOOOOOOOOOOOOOOOOOOOOSSS
Length: 42
Base Modification: 5' methylphosphonoate end-blocks, 3' s-end-blocks, 5
methyl C's and 3' 2'F arm
Wild Type
% Editing Efficiency: 0.19 +/- 0.06

ETAGEN Serial Number 100048 (SEQ ID NO. 41)
SEQUENCE 5':
TTCGGCTGAAGCACTGCACGCCCTAGGTCAGGGTGGTCACGA
Sugar:
DDDDDDDDDDDDDDDDDDDDDDDDDDDDDDDFFFFFFFFDDDD
Backbone:
MMOOOOOOOOOOOOOOOOOOOOOOOOOOOOOOOOOOOOSSS

TABLE 1-continued

Editing Oligonucleotide constructions

Length: 42
Base Modification: 5' methylphosphonoate end-blocks, 3' s-end-blocks, 5 methyl C's and 3' 2'F arm
Mutant
% Editing Efficiency: 0.00 +/- 0.00

ETAGEN Serial Number 100049 (SEQ ID NO. 42)
SEQUENCE 5':
TTCGGCTGAAGCACTGCACGCCCTAGGTCAGGGTGGTCACGATT
Sugar:
DDDDDDDDDDDDDDDDDDDDDDDDDDDDDDDDDDDDDDDDDDDD
Backbone:
MMOOOOOOOOOOOOOOOOOOOOOOOOOOOOOOOOOOOOOOOOMM
Length: 44
Base Modification: Phosphorothioate-free 5' and 3' methylphosphonate end-blocks
Mutant
% Editing Efficiency: 0.00 +/- 0.00

ETAGEN Serial Number 100050 (SEQ ID NO. 43)
SEQUENCE 5':
TTCGGCTGAAGCACTGCACGCCGTAGGTCAGGGTGGTCACGATT
Sugar:
DDDDDDDDDDDDDDDDDDDDDDDDDDDDDDDDDDDDDDDDDDDD
Backbone:
MMOOOOOOOOOOOOOOOOOOOOOOOOOOOOOOOOOOOOOOOOMM
Length: 44
Base Modification: Phosphorothioate-free 5' and 3' methylphosphonate end-blocks
Wild Type
% Editing Efficiency: 0.24 +/- 0.09

ETAGEN Serial Number 100058 (SEQ ID NO. 44)
SEQUENCE 5':
CGGCTGAAGCACTGCACGCCGTAGGTCAGGGTGGTCACGA
Sugar:
DDDMMMMMMMDDDDDDDDDDDDDDDDDDDFFFFFFFFFDDD
Backbone:
SSSOOOOOOOOOOOOOOOOOOOOOOOOOOOOOOOOOOOSSS
Length: 40
Base Modification: 5' 8 x 2'-O-methyl and 8 x 3' 2'F high affinity arms with s end-blocks
Wild Type
% Editing Efficiency: ND +/-

ETAGEN Serial Number 100060 (SEQ ID NO. 45)
SEQUENCE 5':
          M   M M MM       M
CGGCTGAAGCACTGCACGCCGTAGGTCAGGGTGGTCACGA
Sugar:
DDDMMMMMMMDDDDDDDDDDDDDDDDDDDFFFFFFFFFDDD
Backbone:
SSSOOOOOOOOOOOOOOOOOOOOOOOOOOOOOOOOOOOSSS
Length: 40
Base Modification: 5' 8 x 2'-O-methyl and 3' 8 x 2'F high affinity arms with s end-blocks, with central 5 Methyl Cs
Wild Type
% Editing Efficiency: ND +/-

ETAGEN Serial Number 100062 (SEQ ID NO. 46)
SEQUENCE 5':
CGGCTGAAGCACTGCACGCCGTAGGTCAGGGTGGTCACGA
Sugar:
DDDDDDDDDDDDDDDDDDDDDDDDDFFFFFFFFFFFFFDDD
Backbone:
SSSOOOOOOOOOOOOOOOOOOOOOOOOOOOOOOOOOOOSSS
Length: 40
Base Modification: 3' 14 x 2'F high affinity arms with s end-blocks
Wild Type
% Editing Efficiency: ND +/-

ETAGEN Serial Number 100064 (SEQ ID NO. 47)
SEQUENCE 5':
CGGCTGAAGCACTGCACGCCGTAGGTCAGGGTGGTCACGA
Sugar:
DDDDDDDDDDDDDDDDDFFFFFFFFFFFFFFFFFFFFFDDD
Backbone:
SSSOOOOOOOOOOOOOOOOOOOOOOOOOOOOOOOOOOOSSS TABLE 1-continued Editing Oligonucleotide constructions Length: 40
Base Modification: 3' 20 x 2'F high affinity arms with s end-blocks
Wild Type
% Editing Efficiency: ND +/-

ETAGEN Serial Number 100066 (SEQ ID NO. 48)
SEQUENCE 5':
CGGCTGAAGCACTGCACGCCGTAGGTCAGGGTGGTCACGA
Sugar:
DDDMMMMMMMMMMMMMDDDDDDDDDDDDDDDDDDDDDDDD
Backbone:
SSSOOOOOOOOOOOOOOOOOOOOOOOOOOOOOOOOOOSSS
Length: 40
Base Modification: 5' 14 x 2'-O-methyl high affinity arms with s end-blocks
Wild Type
% Editing Efficiency: ND +/-

ETAGEN Serial Number 100068 (SEQ ID NO. 49)
SEQUENCE 5':
CGGCTGAAGCACTGCACGCCGTAGGTCAGGGTGGTCACGA
Sugar:
DDDMMMMMMMMMMMMMMMMMMMDDDDDDDDDDDDDDDDDD
Backbone:
SSSOOOOOOOOOOOOOOOOOOOOOOOOOOOOOOOOOOSSS
Length: 40
Base Modification: 5' 20 x 2'-O-methyl high affinity arms with s end-blocks
Wild Type
% Editing Efficiency: ND +/-

ETAGEN Serial Number 100070 (SEQ ID NO. 50)
SEQUENCE 5':
CATGTGGTCGGGGTAGCGGCTGAAGCACTGCACGCCGTAGGTCAGGGTGGTCACGAGGGTGGGCCAGGGCAC
Sugar:
DDDMMMMMMMMDDDDDDDDDDDDDDDDDDDDDDDDDDDDDDDDDDDDDDDDDDDDDDDDDDDDDDDDDDDDD
Backbone:
SSSOOOOOOOOOOOOOOOOOOOOOOOOOOOOOOOOOOOOOOOOOOOOOOOOOOOOOOOOOOOOOOOOOOSSS
Length: 72
Base Modification: 5' 8 x 2'-O-methyl high affinity arms with s end-blocks
Wild Type
% Editing Efficiency: ND +/-

ETAGEN Serial Number 100072 (SEQ ID NO. 51)
SEQUENCE 5':
CATGTGGTCGGGGTAGCGGCTGAAGCACTGCACGCCGTAGGTCAGGGTGGTCACGAGGGTGGGCCAGGGCAC
Sugar:
DDDMMMMMMMMMMMMMMMMMMMMMMMMDDDDDDDDDDDDDDDDDDDDDDDDDDDDDDDDDDDDDDDDDDDDD
Backbone:
SSSOOOOOOOOOOOOOOOOOOOOOOOOOOOOOOOOOOOOOOOOOOOOOOOOOOOOOOOOOOOOOOOOOOSSS
Length: 72
Base Modification: 5' 24 x 2'-O-methyl high affinity arms with s end-blocks
Wild Type
% Editing Efficiency: ND +/-

ETAGEN Serial Number 100074 (SEQ ID NO. 52)
SEQUENCE 5':
CGGCTGAAGCACTGCACGCCGTAGGTCAGGGTGGTCACGACGCG
Sugar:
LDDDDDDDDDDDDDDDDDDDDDDDDDDDDDDDDDDDDDDDDDDD
Backbone:
OOOOOOOOOOOOOOOOOOOOOOOOOOOOOOOOOOOOOOOOSSSS
Length: 45
Base Modification: L = 5' CY3 (TriLink Biotechnologies, San Diego, CA) end-
block 3' phosphorothioate end-block
Wild Type
% Editing Efficiency: ND +/-

ETAGEN Serial Number 100076 (SEQ ID NO. 53)
SEQUENCE 5':
CGGCTGAAGCACTGCACGCCGTAGGTCAGGGTGGTCACGA
Sugar:
LDDDDDDDDDDDDDDDDDDDDDDDDDDDDDDDDDDDDDDDQ
Backbone:
OOOOOOOOOOOOOOOOOOOOOOOOOOOOOOOOOOOOOOOO
Length: 41
Base Modification: L = 5' CY3 and Q = C-3 amino linker (TriLink
Biotechnologies, San Diego, CA) end-blocks
Wild Type
% Editing Efficiency: ND +/-

TABLE 1-continued

Editing Oligonucleotide constructions

ETAGEN Serial Number 100078 (SEQ ID NO. 54)
SEQUENCE 5':
CGGCTGAAGCACTGCACGCCGTAGGTCAGGGTGGTCACGA
Sugar:
LDDDDDDDDDDDDDDDDDDDDDDDDDDDDDDDDDDDDDDDL
Backbone:
OOOOOOOOOOOOOOOOOOOOOOOOOOOOOOOOOOOOOOOO
Length: 40
Base Modification: L = UNA(unlocked nucleic acid) 5' and 3' end-blocks
Wild Type
% Editing Efficiency: ND +/-

ETAGEN Serial Number 100079 (SEQ ID NO. 55)
SEQUENCE 5':
CGGCTGAAGCACTGCACGCCGTAGGTCAGGGTGGTCACGA
Sugar:
QMMDDDDDDDDDDDDDDDDDDDDDDDDDDDDDDDDDDDDDDQ
Backbone:
OOOOOOOOOOOOOOOOOOOOOOOOOOOOOOOOOOOOOOOO
Length: 41
Base Modification: Q = C3 amino linkers 5' and 3' end-blocks (TriLink
Biotechnologies, San Diego, CA)
Wild Type
% Editing Efficiency: ND +/-

ETAGEN Serial Number 100080 (SEQ ID NO. 56)
SEQUENCE 5':
CGGCTGAAGCACTGCACGCCGTAGGTCAGGGTGGTCACGA
Sugar:
QMMMMMMMMMMMDDDDDDDDDDDDDDDDDDFFFFFFFFFFQ
Backbone:
OOOOOOOOOOOOOOOOOOOOOOOOOOOOOOOOOOOOOOOO
Length: 41
Base Modification: L = UNA Q = C3 Amino Linker end-blocks with 3' 10 x 2'F arm 5'
11 x 2'-O-methyl and 5 Methyl C editing region
Wild Type
% Editing Efficiency: ND +/-

ETAGEN Serial Number 100082 (SEQ ID NO. 57)
SEQUENCE 5':
TCGTGACCACCCTGACCTACGGCGTGCAGTGCTTCAGCCG
Sugar:
DDDDDDDDDDDDDDDDDDDDDDDDDDDDDDDDDDDDDDDD
Backbone:
SSSOOOOOOOOOOOOOOOOOOOOOOOOOOOOOOOOOOSSS
Length: 40
Base Modification: COMPLEMENTARY DNA STRAND TO THE PARENT with
phosphorothioate end-blocks
Wild Type
% Editing Efficiency: ND +/-

ETAGEN Serial Number 100083 (SEQ ID NO. 58)
SEQUENCE 5':
TCGTGACCACCCTGACCTACGGCGTGCAGTGCTTCAGCCG
Sugar:
RRRRRRRRRRRRRRRRRRRRRRRRRRRRRRRRRRRRRRRR
Backbone:
SSSOOOOOOOOOOOOOOOOOOOOOOOOOOOOOOOOOOSSS
Length: 40
Base Modification: COMPLEMENTARY RNA STRAND TO THE PARENT with
phosphorothioate end-blocks
Wild Type
% Editing Efficiency: ND +/-

ETAGEN Serial Number 100084 (SEQ ID NO. 59)
SEQUENCE 5':
CGGCTGAAGCACTGCACGCCGTAGGTCAGGGTGGTCACGA
Sugar:
DDDRRRRRRRRDDDDDDDDDDDDDDDDDDFFFFFFFFDDD
Backbone:
SSSOOOOOOOOOOOOOOOOOOOOOOOOOOOOOOOOOOSSS
Length: 40
Base Modification: 5' 8x RNA and 3' 8 x 2'F high affinity arms with s end-blocks
Wild Type
% Editing Efficiency: ND +/-

TABLE 1-continued

Editing Oligonucleotide constructions

```
ETAGEN Serial Number 100085 (SEQ ID NO. 60)
SEQUENCE 5':
CATGTGGTCGGGGTAGCGGCTGAAGCACTGCACGCCGTAGGTCAGGGTGGTCACGAGGGTGGGCCAGGGCAC
Sugar:
MRMRMRMRMRMRMRMRMRMRMDDDDDDDDDDDDDDDDDDDDDDDDDDDDDDDDDDDDDDDDDDDDDDDDDDDD
Backbone:
ooooooooooooooooooooooooooooooooooooooooooooooooooooooooooooooooooooosss
Length: 73
Base Modification: Editing/Guide Strand with 5' RISC entry site of
alternating RNA/2'-O-methyl
Wild Type
% Editing Efficiency: ND +/-

ETAGEN Serial Number 100086 (SEQ ID NO. 61)
SEQUENCE 5':
CCGCTACCCCGACCACATGTT
Sugar:
MMRRRRRRRRRRRRRRRRRRDD
Backbone:
oooooooooooooooooooooo
Length: 21
Base Modification: Sense strand that will allow the duplex with 100085 to
form editing compound capable of RISC entry
Wild Type
% Editing Efficiency: ND +/-
```

Legend:
BACKBONE: o = phosphodiester, s = phosphorothioate, and m = methyphosphonate, the first backbone indicated in the string of letters corresponds to the modification between the first and $2^{nd}$ nucleotides of the sequence, the second backbone in the string of letters corresponds to the modification between the $2^{nd}$ and $3^{rd}$ nucleotides of the sequences, and so on.
SUGAR: D = DNA, R = RNA, M = 2'-O-methyl, F = 2' F, and L and Q = as noted in modification notes
BASE: M = 5' methyl C
ND: No Data Editing oligonucleotide 100034 has 5' and 3' 2'F arms (5' and 3' proximal segments), and demonstrates low but significant editing. This was unexpected because 2' F is sterically more similar to DNA than 2'-O-methyl, and 2' F was highly active in editing when incorporated in the 3' arm. In the 5' arm, 2'-O-methyl modification is better tolerated than the 2'F modification, which was again unexpected. This implies constructions like editing oligonucleotide 100058 are preferred over constructs with the same modification in each arm.

Extensive modifications as seen with editing oligonucleotide 100047 was compatible with editing, which is useful because each of the modifications lowers projected toxicity relative to the parent oligonucleotide often used in the art (5' and 3' phosphorothioate DNA exonuclease blocking terminal segments are commonly used in the art). It is believed that part of this reduced toxicity is due to reduced activation of Toll-Like Receptors by 2' modified linkages, compared to 2' H in DNA or 2' OH in RNA. Higher target specificity is achieved because the arms do not serve as efficient editing sites, thus there are less potential off-target interactions.

While 5' methylphosphonate exonuclease blocking terminal segments were quite active, using both 5' and 3' methyl phosphonates terminal segments were useful but less active. This construction removed all phosphorothioates that are associated with blocking cell proliferation in many in vitro assays.

A single 5' methyl C modification near the editing site was consistent with relatively high editing efficiency, as were multiple 5' methyl C modifications.

Extending the stretch of 3' proximal segment modifications towards the 3' editing segment may be less preferred due to interference with the editing reaction, but these additional modifications are projected to further increase nuclease stability and reduces immune stimulation (e.g. editing oligonucleotide 100062). This is also the case with the 5' modifications (e.g. editing oligonucleotide 100066).

Extending the 2'-O-methyl modifications, which are more like RNA than DNA, into the editing site (e.g. editing oligonucleotide 100068) are expected to dramatically reduce or eliminate editing activity. Also, extending the 3' 2'F modifications into the editing site (e.g. editing oligonucleotide 100064) is expected to reduce or eliminate editing activity.

Longer editing oligonucleotides have more linkages that may be modified at locations distant from the 5' or 3' editing segment, or the editing site (e.g. editing oligonucleotide 100072).

While methylphosphonates made an excellent 5' end-block. Editing oligonucleotide 100074 has a CY3 5' end-block and 3 complimentary phosphorothioate DNAs on the 3' end, and provides another novel combination.

Locked Nucleic Acids (LNAs) may also be employed as an end-blocking group, but they can add to in vivo toxicity. For this reason we prefer employing Unlocked Nucleic Acids (UNAs) (e.g. editing oligonucleotide 100078), or simple linkers on one or both termini as nuclease end-blocks. While exonucleases can jump over a single modification of DNA, this may be less of a problem in combination with 2'-modified terminal residues (e.g. editing oligonucleotide 100080). End-blocking linkers have the additional advantage that they can also be used to link conjugates to the editing oligonucleotide. These conjugates (e.g., conjugation with cholesterol (U.S. patent application no. 20130131142 A1) and Gal-Nac (U.S. Pat. No. 8,106,022) have been shown to increase uptake of oligonucleotides into cells in culture and in vivo in animals. Conjugates of these moieties with editing oligonucleotides can be prepared utilizing methods known in the art and will eliminate the need for delivery vehicles that add expense and/or toxicity (e.g., liposomes).

There is some controversy as to whether single-stranded DNA is better than duplexes for editing. Editing oligonucleotide 100082 contains end-blocks that are complimentary to editing oligonucleotide 100005, 100031 and others in this modification series. The editing oligonucleotide may be added to cells separately from a complimentary oligonucleotide, or may be pre-hybridized with a complimentary editing oligonucleotide of any modified chemistry described herein to form a duplex. The advantages of the pre-formed duplex, is that double-stranded DNA is resistant to single-stranded nucleases. However, a perceived disadvantage of the duplex may be that the bases are not free to hybridize with the target DNA, unless some cellular repair/recombination machinery facilitates target binding. Depending on the target gene, cell type and route of administration single or double-stranded editing oligonucleotides may be more suitable for editing.

Editing oligonucleotide 100083 is an RNA protector oligonucleotide with end-blocks that are complimentary to editing oligonucleotides 100005, 100031 and others in the series of chemically modified editing oligonucleotides GFP sequences disclosed herein. This oligonucleotide protects the complimentary editing guide oligonucleotide from nucleases in serum, the endo-lysosomal pathway and the cytoplasm. When in the cytoplasm or nucleoplasm, the RNA strand will eventually be degraded by endogenous RNase H, liberating the single-stranded editing oligonucleotide for hybridization to the target DNA. This is an improvement upon 2'-O-methyl protecting oligonucleotides which reduced the activity of the editing oligonucleotide presumably due to interfering with hybridization to the target DNA.

Editing oligonucleotide (e.g., 100085) has been designed so that the 5' proximal region, when hybridized to protector oligonucleotide 10086 forms a duplex capable of loading into the RNA-Induced Silencing Complex (RISC). The guide strands hybridization rate to complementary target nucleic acid (both RNA and DNA targets; Saloman, et al. Cell 162:84-96, 2015) is dramatically increased as a result of being loaded into Argonaut. This enhancement of the hybridization on-rate by RISC is what makes siRNA about 10-100 times more potent than the corresponding antisense (e.g., no enhancement by RISC observed with antisense). Thus, the 5' end of the editing oligonucleotide loaded into Argonaut will hybridize more rapidly to the target chromosomal DNA, increasing the potency and/or efficiency of genome editing. This mechanism uses the endogenous cellular machinery to enhance target binding, and therefore does not require the addition of exogenous proteins like Cas9 to accelerate enhance target binding. The advantage of this embodiment of the present invention is that it avoids the challenges of delivering exogenous proteins to cells. Once the binding to target DNA is seeded by the 5' proximal region of the editing oligonucleotide complexed with Argonaut, the remaining duplex will form rapidly.

Based on the data herein with editing oligonucleotide 100037, it appears that the 5' end region of editing oligonucleotide can be modified with 2'-O-methyl RNA while maintaining editing efficiency, and partial modification of an oligonucleotide with 2'-O-methyl modification is compatible with RISC loading (U.S. patent application nos. 20130317080, 20150267200, 20150105545, 20110039914 and U.S. patent application Ser. No. 12/824,011). The protector oligonucleotide (passenger strand) is preferably 10-50 nucleotides, more preferably 12-30 nucleotides, and most preferably 19-27 nucleotides and completely or substantially complementary to the target. In this construction the editing oligonucleotide is designed following some generally accepted design rules for preparing RNAi or microRNAs (miRNAs). For example, a two base pair 3' overhang of the passenger strand is preferred, but blunt and other end structures compatible with RNAi are also useful. A free 5' hydroxyl or a phosphorylated 5' hydroxyl on the guide (editing strand) is also provided. A range of chemical modifications and structures that are compatible with RNAi may be employed in this editing strategy. It is preferred that the 5' end of the editing oligonucleotide duplexed with the passenger RNA does not have more than about 4 DNA linkages bound to RNA in the passenger strand, which can activate RNase H cleavage of the passenger strand, reducing RISC loading. In a preferred embodiment, when employing a RISC loading double-stranded region within the editing oligonucleotide that is long enough to serve as a dicer substrate, chemical modifications or mismatches may be inserted in a manner known in the art to reduce or eliminate dicer cleavage, such as incorporating 2'-O-methyl modification(s) at the dicer cleavage site(s) (Salomon et al. Nucleic Acids Research, 38(11):3771-9 Feb. 2010). Reducing dicer cleavage is beneficial, because dicer cleavage of the editing oligonucleotide on the side of the duplex nearest the editing site would detach the RISC loaded region from the rest of the editing oligonucleotide, which would eliminate the advantage of RISC loading if this occurred prior to strand invasion into the targeted DNA duplex.

Double-stranded structures capable of loading into RISC are known in the art, and include STEALTH RNAi compounds (Life Technologies, San Diego CA and U.S. Pat. No. 8,815,821), Dicer substrates (U.S. Pat. Nos. 8,349,809, 8,513,207, and 8,927,705), rxRNA ori (RXi Pharmaceuticals, Marlborough, Massachusetts), RNAi triggers with shortened duplexes (U.S. Patent application no. 20120065243 filed 2009), and siRNA (U.S. Pat. Nos. 7,923, 547; 7,956,176; 7,989,612; 8,202,979; 8,232,383; 8,236, 944; 8,242,257; 8,268,986; 8,273,866 and U.S. patent application Ser. No. 13/693,478). These RNAi trigger configurations, with the various chemical modification patterns known to support RISC loading, and in some cases enhance tissue and cellular uptake, can be incorporated into the editing oligonucleotide, as has been done with siRNA in the RISC loading editing oligonucleotide described herein (ETAGEN Serial Number 100085 hybridized to 100086) so long as a free 5' hydroxyl or a phosphorylated 5' hydroxyl on the editing strand is maintained, or liberated within the cell.

VI. ADVANTAGES

The embodiments of the present invention that employ the Kmiec method have some advantages over the chemical modification method, because the Kmiec method does not require chemically reactive groups be attached to the editing oligonucleotide, achieves editing of a base to any other natural base and allows small insertions or deletions.

The embodiments of the present invention that employ the chemical modification method has some advantages over the Kmiec method, because the chemical modification method involves the addition or removal of specific groups (i.e., methylation, ethylation or deamination) to change the targeted nucleobase base-pairing specificity, and thus does not require active cellular recombination machinery.

The editing oligonucleotides of the present invention may be utilized without CRISPR or proteins such as zinc finger or engineered programmable nucleases. Methods utilizing CRISPR and/or zinc finger are using single-stranded oligonucleotides which are not the guide RNA in CRISPR, but a separate single-stranded oligonucleotide, as the donor to repair the site. However, the methods and compositions of the present invention do not strictly require these other exogenous protein components and results in similar or substantially similar efficiencies of precise editing as current methods.

The present invention is a nucleic acid repair approach that differs from CRISPR/Cas9, Zinc Finger and Talen DNA editing approaches because it repairs the mutant sequence directly and accurately without creating potentially dangerous breaks in the DNA. In addition, the present invention may optionally be administered without delivery particles or immunogenic proteins.

The present invention may be utilized to silence any gene by creating a site-specific mutation, for example a stop codon at a desired location that prevents transcription. However, one of the unique applications of the present invention is the targeting of a point mutation that modulates or corrects the function of gene (e.g., gain-of-function mutations caused by dominant mutations) that cannot be addressed by other known silencing methods Other approaches such as competing gene therapy and mRNA replacement strategies can replace a mutated gene product. However, the present invention has the advantage of achieving completely normal gene regulation and expression levels without incorporation of vector sequences or causing chromosomal damage at vector insertion sites.

It will be understood that any of the above described methods can be used in combination with certain other methods herein, or not used in such combinations. Furthermore, any of the above described compositions can be optionally used with certain methods described herein.

VII. EXAMPLES

Table 1 and FIG. 2 describe examples of editing oligonucleotides of the present invention. The editing oligonucleotide sequences in Table 1 FIG. 2 target a null mutation in green fluorescent protein, and correct this mutation into a functional sequence that can be readily monitored by assaying for fluorescence (Erin E. Brachman and Eric B. Kmiec supra)). These chemical modification patterns can be applied to editing oligonucleotides targeting mutations, to editing oligonucleotides which create a protective allele or to editing oligonucleotides that create other desirable changes in the genome. In each case in these examples, when not already determined by the disclosed sequence, and in other embodiments of the present invention the editing site may be in the center region of the editing oligonucleotide, or may be offset towards the 5'- or 3'-termini. In preferred embodiments, the editing site is more than five nucleotides from either terminus. In each case, it may also be preferable to have the editing site in a region of DNA that is unmodified or, if modified, has conservative modifications that are still recognized as DNA by the cellular DNA repair and replication machinery (i.e. phosphorothioate or 5' methyl C.

Editing oligonucleotides may be designed to be complementary to either strand of the genomic DNA. It is preferred that they will be designed to bind to the template strand for lagging strand synthesis, as this tends to lead to more efficient editing. However, each strand may be targeted and it can be readily determined which strand leads to more efficient editing.

FIG. 2, shows data from some oligonucleotides in Table 1. Gen 3A is oligonucleotide #100013 and #100014, Gen 3B is oligonucleotide #100015 and #100016, Gen 3C is oligonucleotide #100017 and #100018, Gen 1 is oligonucleotide #100003 and #100004 and Gen 2 is oligonucleotide #100005 and #100006.

TABLE 2

| The phosphorothioate configurations below, with editing site located at any site within the internal phosphodiester region. 5' phosphorothioates | Being realized that there can optionally be about 1, 2, 3, 4, 5, 6, 7, 8, 9, 10, 11, 12, 13, 14, 15, 16, 17, 18, 19, 20, 21, 22, 23, 24 to about 25% of the phosphorothioates switched to phosphodiester, and 1, 2, 3, 4, 5, 6, 7, 8, 9, 10, 11, 12, 13, 14, 15, 16, 17, 18, 19, 20, 21, 22, 23, 24 to about 25% phosphodiesters switched to phosphorothioates internal phosphodiesters | In a preferred emobodiment all the sugars are DNA. In another embodiment up to about 1, 5, 10, 15, 20, 30, 40 or 50, 60 or 70% of the sugars are RNA or 2' RNA, in each case where 1, 5, 10, 15, 20 or 30% of the bases are optionally modified, preferable with a methylation. 3' phosphorothioates |
|---|---|---|
| 1 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 2 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 3 | 1, 2, 3, 4, 5, 6, 7, 8, 9, 10, 11, 12, 13, 14, 15, 16, 17, 18, 19, 20, 21, 22, 23, 24, 25, 26, 27, | 1, 2, 3, 4, 5, 6, 7, 8, 9, 10, 11, 12, 13, 14, 15, 16, 17, 18, 19, 20, 21, 22, 23, 24, |

TABLE 2-continued

| The phosphorothioate configurations below, with editing site located at any site within the internal phosphodiester region. 5' phosphorothioates | Being realized that there can optionally be about 1, 2, 3, 4, 5, 6, 7, 8, 9, 10, 11, 12, 13, 14, 15, 16, 17, 18, 19, 20, 21, 22, 23, 24 to about 25% of the phosphorothioates switched to phosphodiester, and 1, 2, 3, 4, 5, 6, 7, 8, 9, 10, 11, 12, 13, 14, 15, 16, 17, 18, 19, 20, 21, 22, 23, 24 to about 25% phosphodiesters switched to phosphorothioates internal phosphodiesters | In a preferred emobodiment all the sugars are DNA. In another embodiment up to about 1, 5, 10, 15, 20, 30, 40 or 50, 60 or 70% of the sugars are RNA or 2' RNA, in each case where 1, 5, 10, 15, 20 or 30% of the bases are optionally modified, preferable with a methylation. 3' phosphorothioates |
|---|---|---|
| | 28, 29, 30, 31, 32, 33, 34, 35, 36, 37, 38, 39, 40, 41, 42, 42, 43, 44, 45, 46, 47, 48, 49 or 50 | 25, 26, 27, 28, 29, 30, 31, 32, 33, 34, 35, 36, 37, 38, 39, 40, 41, 42, 42, 43, 44, 45, 46, 47, 48, 49 or 50 |
| 4 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 5 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 6 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 7 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 8 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 9 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 10 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 11 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 12 | 1, 2, 3, 4, 5, 6, 7, 8, 9, 10, 11, 12, 13, 14, 15, 16, 17, 18, 19, 20, 21, 22, 23, 24, 25, 26, 27, | 1, 2, 3, 4, 5, 6, 7, 8, 9, 10, 11, 12, 13, 14, 15, 16, 17, 18, 19, 20, 21, 22, 23, 24, |

TABLE 2-continued

| The phosphorothioate configurations below, with editing site located at any site within the internal phosphodiester region. 5' phosphorothioates | Being realized that there can optionally be about 1, 2, 3, 4, 5, 6, 7, 8, 9, 10, 11, 12, 13, 14, 15, 16, 17, 18, 19, 20, 21, 22, 23, 24 to about 25% of the phosphorothioates switched to phosphodiester, and 1, 2, 3, 4, 5, 6, 7, 8, 9, 10, 11, 12, 13, 14, 15, 16, 17, 18, 19, 20, 21, 22, 23, 24 to about 25% phosphodiesters switched to phosphorothioates internal phosphodiesters | In a preferred emobodiment all the sugars are DNA. In another embodiment up to about 1, 5, 10, 15, 20, 30, 40 or 50, 60 or 70% of the sugars are RNA or 2' RNA, in each case where 1, 5, 10, 15, 20 or 30% of the bases are optionally modified, preferable with a methylation. 3' phosphorothioates |
|---|---|---|
| | 28, 29, 30, 31, 32, 33, 34, 35, 36, 37, 38, 39, 40, 41, 42, 42, 43, 44, 45, 46, 47, 48, 49 or 50 | 25, 26, 27, 28, 29, 30, 31, 32, 33, 34, 35, 36, 37, 38, 39, 40, 41, 42, 42, 43, 44, 45, 46, 47, 48, 49 or 50 |
| 13 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 14 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 15 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 16 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 17 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 18 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 19 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 20 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 21 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, |

TABLE 2-continued

| The phosphorothioate configurations below, with editing site located at any site within the internal phosphodiester region. 5' phosphorothioates | Being realized that there can optionally be about 1, 2, 3, 4, 5, 6, 7, 8, 9, 10, 11, 12, 13, 14, 15, 16, 17, 18, 19, 20, 21, 22, 23, 24 to about 25% of the phosphorothioates switched to phosphodiester, and 1, 2, 3, 4, 5, 6, 7, 8, 9, 10, 11, 12, 13, 14, 15, 16, 17, 18, 19, 20, 21, 22, 23, 24 to about 25% phosphodiesters switched to phosphorothioates internal phosphodiesters | In a preferred emobodiment all the sugars are DNA. In another embodiment up to about 1, 5, 10, 15, 20, 30, 40 or 50, 60 or 70% of the sugars are RNA or 2' RNA, in each case where 1, 5, 10, 15, 20 or 30% of the bases are optionally modified, preferable with a methylation. 3' phosphorothioates |
|---|---|---|
| | 43, 44, 45, 46, 47, 48, 49 or 50 | 39, 40, 41, 42, 42, 43, 44, 45, 46, 47, 48, 49 or 50 |
| 22 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 23 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 24 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 25 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 26 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 27 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 28 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 29 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 30 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |

TABLE 2-continued

| The phosphorothioate configurations below, with editing site located at any site within the internal phosphodiester region. 5' phosphorothioates | Being realized that there can optionally be about 1, 2, 3, 4, 5, 6, 7, 8, 9, 10, 11, 12, 13, 14, 15, 16, 17, 18, 19, 20, 21, 22, 23, 24 to about 25% of the phosphorothioates switched to phosphodiester, and 1, 2, 3, 4, 5, 6, 7, 8, 9, 10, 11, 12, 13, 14, 15, 16, 17, 18, 19, 20, 21, 22, 23, 24 to about 25% phosphodiesters switched to phosphorothioates internal phosphodiesters | In a preferred emobodiment all the sugars are DNA. In another embodiment up to about 1, 5, 10, 15, 20, 30, 40 or 50, 60 or 70% of the sugars are RNA or 2' RNA, in each case where 1, 5, 10, 15, 20 or 30% of the bases are optionally modified, preferable with a methylation. 3' phosphorothioates |
|---|---|---|
| 31 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 32 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 33 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 34 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 35 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 36 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 37 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 38 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 39 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |

TABLE 2-continued

| The phosphorothioate configurations below, with editing site located at any site within the internal phosphodiester region. 5' phosphorothioates | Being realized that there can optionally be about 1, 2, 3, 4, 5, 6, 7, 8, 9, 10, 11, 12, 13, 14, 15, 16, 17, 18, 19, 20, 21, 22, 23, 24 to about 25% of the phosphorothioates switched to phosphodiester, and 1, 2, 3, 4, 5, 6, 7, 8, 9, 10, 11, 12, 13, 14, 15, 16, 17, 18, 19, 20, 21, 22, 23, 24 to about 25% phosphodiesters switched to phosphorothioates internal phosphodiesters | In a preferred emobodiment all the sugars are DNA. In another embodiment up to about 1, 5, 10, 15, 20, 30, 40 or 50, 60 or 70% of the sugars are RNA or 2' RNA, in each case where 1, 5, 10, 15, 20 or 30% of the bases are optionally modified, preferable with a methylation. 3' phosphorothioates |
|---|---|---|
| 40 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 41 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 42 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 43 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 44 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 45 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 46 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 47 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 48 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
| 49 | 1, 2, 3, 4, 5, 6, 7, 8, 9, 10, 11, 12, 13, 14, 15, 16, 17, 18, 19, | 1, 2, 3, 4, 5, 6, 7, 8, 9, 10, 11, 12, 13, 14, 15, 16, 17, |

TABLE 2-continued

| The phosphorothioate configurations below, with editing site located at any site within the internal phosphodiester region. 5' phosphorothioates | Being realized that there can optionally be about 1, 2, 3, 4, 5, 6, 7, 8, 9, 10, 11, 12, 13, 14, 15, 16, 17, 18, 19, 20, 21, 22, 23, 24 to about 25% of the phosphorothioates switched to phosphodiester, and 1, 2, 3, 4, 5, 6, 7, 8, 9, 10, 11, 12, 13, 14, 15, 16, 17, 18, 19, 20, 21, 22, 23, 24 to about 25% phosphodiesters switched to phosphorothioates internal phosphodiesters | In a preferred emobodiment all the sugars are DNA. In another embodiment up to about 1, 5, 10, 15, 20, 30, 40 or 50, 60 or 70% of the sugars are RNA or 2' RNA, in each case where 1, 5, 10, 15, 20 or 30% of the bases are optionally modified, preferable with a methylation. 3' phosphorothioates |
|---|---|---|
| 50 | 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |
|  | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 42, 43, 44, 45, 46, 47, 48, 49 or 50 |

Methods Employed for Experiments in FIG. 2 and Table 1

A. Cell Line and Culture Conditions

HCT116 cells were acquired from ATCC (American Type Cell Culture, Manassas, VA). HCT116-19 was created by integrating a pEGFP-N3 vector (Clontech, Palo Alto, CA) containing a mutated eGFP gene. The mutated eGFP gene has a nonsense mutation at position 167 resulting in a nonfunctional eGFP protein. For these experiments, HCT116-19 cells were cultured in McCoy's 5A Modified medium (Thermo Scientific, Pittsburgh, PA) supplemented with 10% fetal bovine serum, 2 mM L-Glutamine, and 1% Penicillin/Streptomycin. Cells were maintained at 37° C. and 5% carbon dioxide.

B. Transfection of HCT116-19 Cells

For experiments utilizing synchronized cells, HCT116-19 cells were seeded at $2.5 \times 10^6$ cells in a 100 mm dish and synchronized with 6 mM aphidicolin for 24 hours prior to targeting. Cells were released for 4 hours (or indicated time) prior to trypsinization and transfection by washing with PBS (2/2) and adding complete growth media. Synchronized and unsynchronized HCT116-19 cells were transfected at a concentration of $5 \times 10^5$ cells/100 ul in 4 mm gap cuvette (BioExpress, Kaysville, UT). Single-stranded oligonucleotides were electroporated (250V, LV, 13 ms pulse length, 2 pulses, is interval) using a Bio-Rad Gene Pulser XCell™ Electroporation System (Bio-Rad Laboratories, Hercules, CA). Cells were then recovered in 6-well plates with complete growth media at 37° C. for the indicated time prior to analysis. Analysis of gene edited cells. Fluorescence (eGFP) was measured by a Guava EasyCyte 5 HT™ Flow Cytometer (Millipore, Temecula, CA). Cells were harvested by trypsinization, washed once with PBS and resuspended in buffer (0.5% BSA, 2 mM EDTA, 2 mg/mL Propidium Iodide (PI) in PBS). Propidium iodide was used to measure cell viability as such, viable cells stain negative for PI (uptake). Correction efficiency was calculated as the percentage of the total live eGFP positive cells over the total live cells in each sample. Error bars are produced from three sets of data points using calculations of Standard Error.

Example 1

Figure 3:
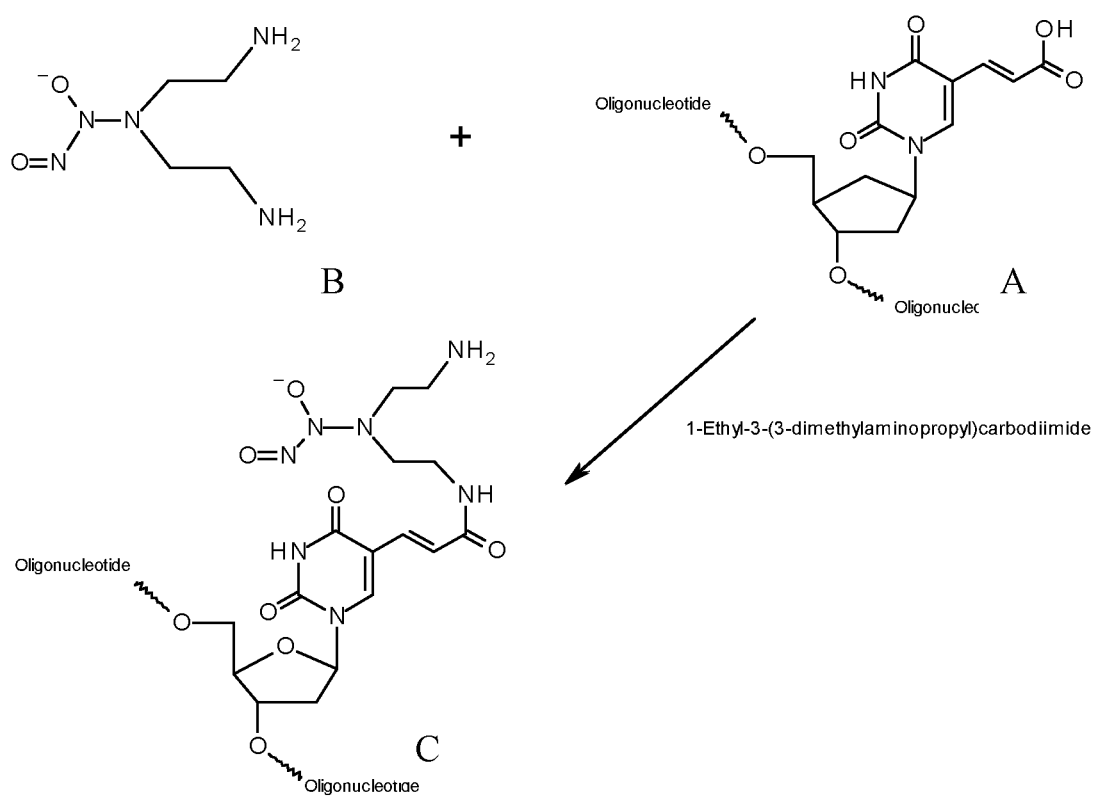
FIG. 3: Synthesis of editing oligonucleotides with 2'-deoxyuridine-NOC-18 conjugate for Adenosine to Inosine conversion, (A) oligonucleotide containing 5-carboxyvinyl-2'-deoxyuridine residue, (B) 1-Hydroxy-2-oxo-3,3-bis(2-aminoethyl)-1-triazene (NOC-18) and (C) 2'-deoxyuridine-NOC-18 conjugate.

Synthesis of Editing Oligonucleotides with 2'-deoxyuridine-NOC-18 Conjugate for A to I Conversion (G Mimic, FIG. 3A-C)

5'-dimethoxytrityl-(E)-5-(carbomethoxyvinyl)-2'-deoxyuridine-3'-phosphoramidite is prepared as described in WO2013150902. An oligonucleotide containing 5-carboxyvinyl-2'-deoxyuridine residue (FIG. 3A) is prepared by standard automated oligonucleotide synthesis using nucleoside phosphoramidite building blocks. The 5'-dimethoxytrityl-(E)-5-(carbomethoxyvinyl)-2'-deoxyuridine-3'-phosphoramidite is incorporated into the oligonucleotide at one or more desired locations. The oligonucleotide is deprotected by treatment with 0.5M aqueous sodium hydroxide for 1 hour at room temperature followed by treatment with concentrated ammonium hydroxide at 50° C. for 3 hours. Crude oligonucleotide is isolated and purified by a combination of anion exchange and reverse phase HPLC. The sequence and structure is confirmed by Mass Spectrometry.

1-Hydroxy-2-oxo-3,3-bis(2-aminoethyl)-1-triazene (NOC-18) (Aldrich; Cat #A5581, FIG. 1B) is conjugated to the one or more 5'-dimethoxytrityl-(E)-5-(carbomethoxyvinyl)-2'-deoxyuridine residues in the oligonucleotide by incubation of 1 μmol of oligonucleotide with 20 μmol of 1-ethyl-3-(3-dimethylaminopropyl)carbodiimide (EDAC) and 20 μmol of NOC-18 in 0.1 M sodium bicarbonate buffer (pH 9.5-10.0). The EDAC is added by 2 μmol portions every 10 minutes. After the reaction is complete, the 2'-deoxyuridine-NOC-18 conjugate (FIG. 3C) is isolated and purified by a combination of anion exchange and reverse phase HPLC. The sequence and structure is confirmed by Mass Spectrometry.

Example 2

Synthesis of Oligonucleotides with 3,5-pentanoic acid-NOC-18 Conjugate for A to I Conversion (G Mimic) and for C to U Conversion

Figure 4:
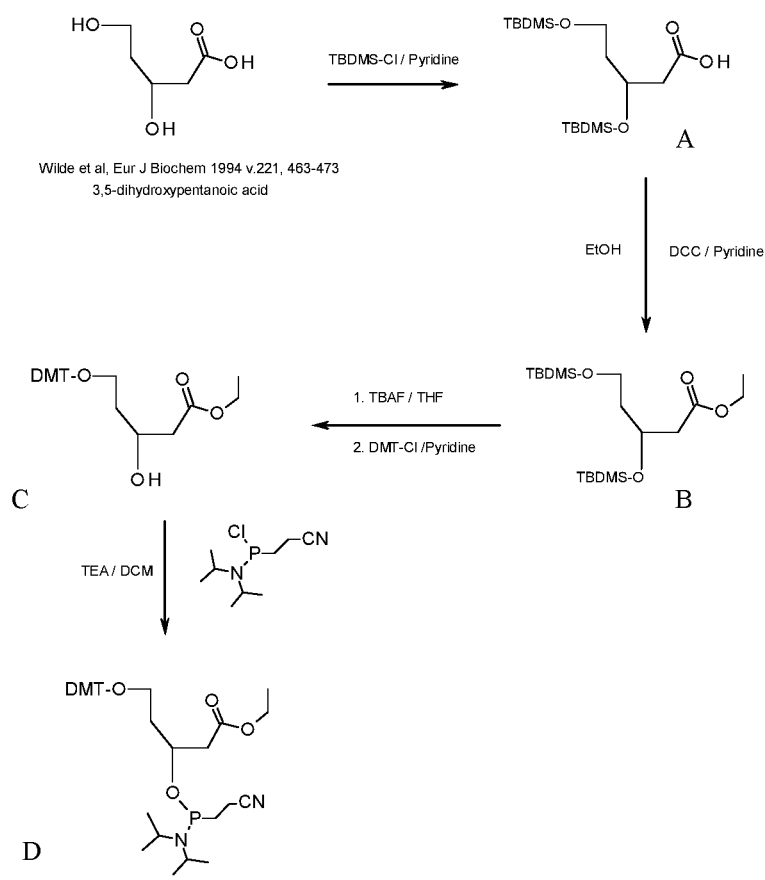
FIG. 4: Synthesis of 5-(4,4'-dimethoxytrityl)-pentanoic acid ethyl ester 3-phosphoramidite. (A) Preparation of 3,5-bis-O,O-(tert-butyldimethylsilyl) pentanoic acid, (B) preparation of 3,5-bis-O,O-(Cert-butyldimethylsilyl)pentanoic acid ethyl ester, (C) preparation of 3-hydroxy-5-(4,4'-dimethoxytrityl)-pentanoic acid ethyl ester, and (D) preparation of 5-(4,4'-dimethoxytrityl)-pentanoic acid ethyl ester 3-phosphoramidite.

A. Synthesis of 5-(4,4'-dimethoxytrityl)-pentanoic acid ethyl ester 3-phosphoramidite (FIG. 4)

1. Preparation of 3,5-bis-O,O-(tert-butyldimethylsilyl) pentanoic acid (FIG. 4A)

3,5-dihydroxypentanoic acid is treated with 2.2 equivalents of Cert-butyldimethylsilyl chloride (TBDMS-Cl) in pyridine for 12 hours at room temperature. The mixture is evaporated at reduced pressure. The residue is used in next step without purification.

2. Preparation of 3,5-bis-O,O-(tert-butyldimethylsilyl) pentanoic acid ethyl ester (FIG. 4B)

Crude 3,5-bis-O,O-(tert-butyldimethylsilyl)pentanoic acid is dissolved in a mixture of anhydrous pyridine and absolute ethanol (9:1). Five molar equivalents of N,N'-dicyclohexyl carbodiimide are added and the mixture is stirred for 4 hours at room temperature. The solution is filtered and the filtrate is evaporated. The crude product is used in the next step.

3. Preparation of 3-hydroxy-5-(4,4'-dimethoxytrityl)-pentanoic acid ethyl ester (FIG. 4C)

3,5-bis-O,O-(tert-butyldimethylsilyl)pentanoic acid ethyl ester is dissolved in 1M tetrabutylammonium fluoride (TBAF) in tetrahydrofuran and stirred for 24 hours at room temperature. The mixture is evaporated and dissolved in anhydrous pyridine. 4,4'-dimethoxyytrityl chloride (DMT-Cl, 1.2 equivalents) is added and the mixture is stirred for 12 hours. The product is extracted with dichloromethane (DCM)/1M sodium chloride and the organic layer is dried with anhydrous sodium sulfate. The 3-hydroxy-5-(4,4'-dimethoxytrityl)-pentanoic acid ethyl ester is purified by silica gel chromatography in DCM-methanol (0.1% pyridine). Fractions containing pure product are combined, evaporated and dried at high vacuum. The structure of the compound is confirmed by NMR and Mass Spectrometry.

4. Preparation of 5-(4,4'-dimethoxytrityl)-pentanoic acid ethyl ester 3-phosphoramidite (FIG. 4D)

3-hydroxy-5-(4,4'-dimethoxytrityl)-pentanoic acid ethyl ester is dissolved in DCM and 1 equivalent of triethylamine and 1.1 equivalent of 2-cyanoethyl N,N-diisopropylchlorophosphoramidite is added. After 2 hours the mixture is evaporated and the residue is dissolved in ethyl acetate. Crude 1-(4,4-dimethoxytrityl)-2-[2-rifluoroacet-amido] ethyl-3-phosphoramidite is purified by silica gel chromatography in hexane-ethyl acetate containing 0.1% pyridine. Fractions containing pure product are combined, evaporated and dried at high vacuum. The structure of the compound is confirmed by NMR and Mass Spectrometry.

B. Synthesis of Oligonucleotide Containing Carboxylic Group Attached to Internal Pentanoic Acid Residue An oligonucleotide containing one or more internal pentanoic acid residues is prepared by standard automated oligonucleotide synthesis using nucleoside phosphoramidite building blocks. The 5-(4,4'-dimethoxytrityl)-pentanoic acid ethyl ester 3-phosphoramidite is used for incorporation at one or more desired locations in the oligonucleotide. The oligonucleotide is deprotected by treatment with 0.5M aqueous sodium hydroxide for 1 hour at room temperature followed by treatment with concentrated ammonium hydroxide at 50° C. for 3 hours. Crude oligonucleotide is isolated and purified by a combination of anion exchange and reverse phase HPLC. The sequence and structure is confirmed by Mass spectrometry.

Figure 5:
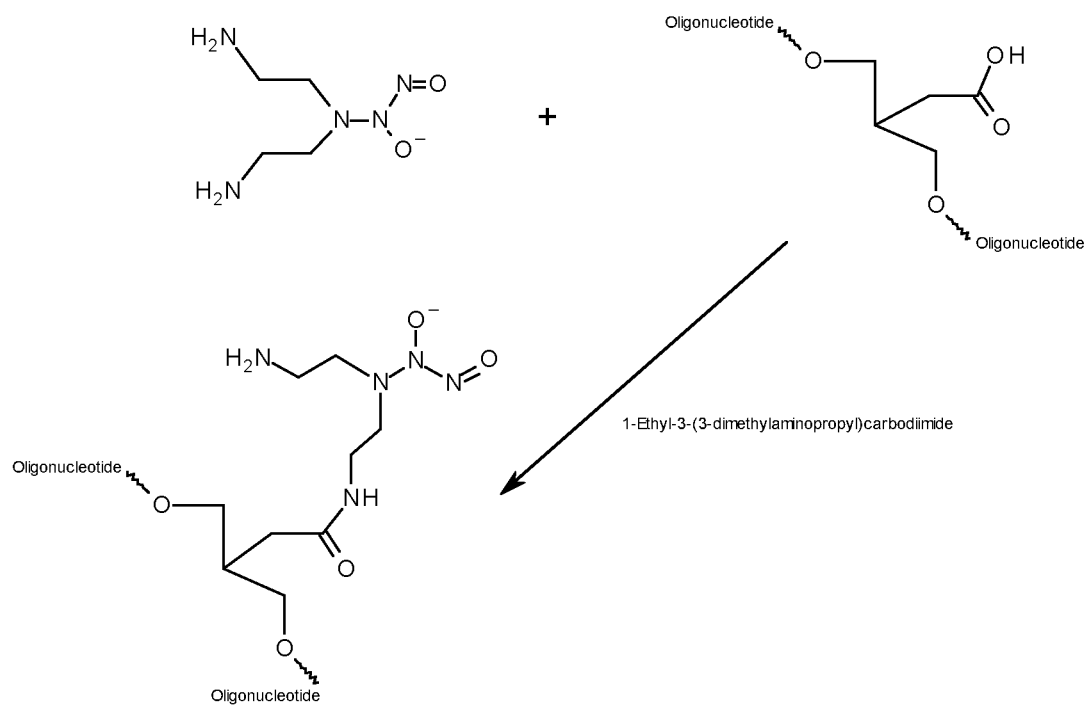
FIG. 5: Conjugation of NOC-18 to an oligonucleotide containing carboxylic group of internal pentanoic acid residue.

C. Conjugation of NOC-18 to an Oligonucleotide Containing Carboxylic Group of Internal Pentanoic Acid Residue (FIG. 5)

Conjugation of NOC-18 to an oligonucleotide is performed by incubation of 1 µmol of oligonucleotide containing pentanoic acid residue with 20 µmol of 1-ethyl-3-(3-dimethylaminopropyl)carbodiimide (EDAC) and 20 µmol of NOC-18 in 0.1 M sodium bicarbonate buffer (pH 9.5-10.0). EDAC is added in 2 µmol portions every 10 minutes. The NOC-18-Oligonucleotide conjugate is isolated and purified by a combination of anion exchange and reverse phase HPLC. The sequence and structure is confirmed by Mass Spectrometry.

Example 3

Synthesis of Editing Oligonucleotides with L-Cysteic Acid Conjugate for C to U Conversion

A. Synthesis of $N^2$-isobutyryl-7-deaza-7-aminomethyl-2'-deoxyguanosine

Figure 6:
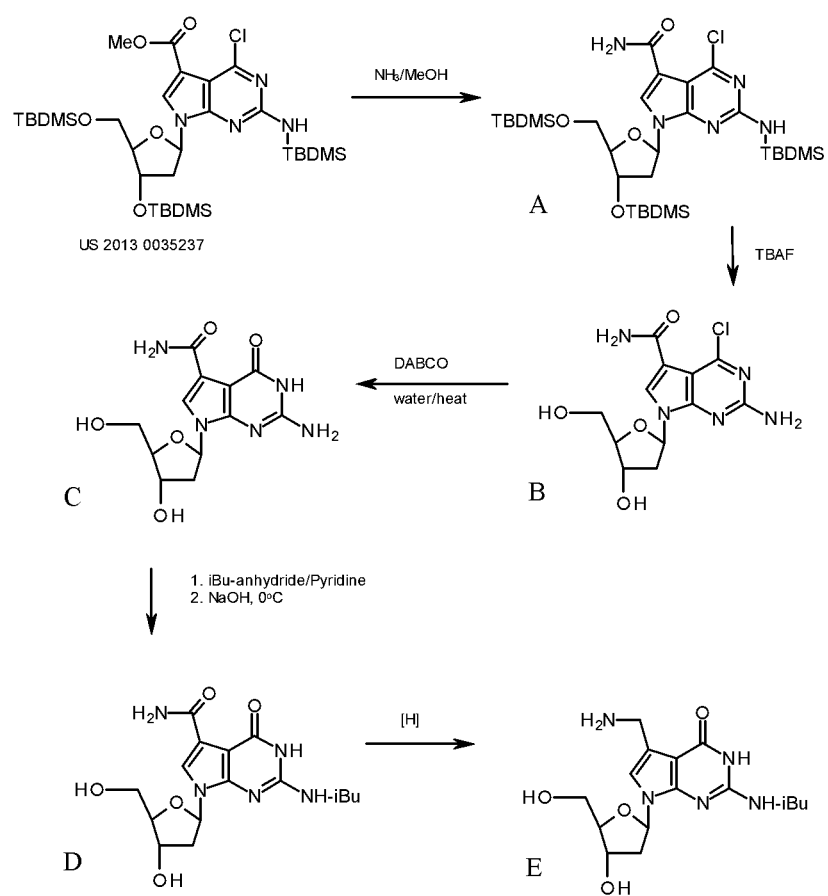
FIG. 6: Synthesis of $N^2$-isobutyryl-7-deaza-7-aminomethyl-2'-deoxyguanosine. (A) Preparation of 9-[3',5',$N^2$-tri(tert-butyl-dimethylsilyl)-β-D-2'-deoxyribofuranosyl]-7-deaza-7-carbamido-6-chloropurine, (B) preparation of 9-β-D-2'-deoxyribofuranosyl-7-deaza-7-carbamido-6-chloropurine, (C) preparation of 7-deaza-7-carbamido-2'-deoxyguanosine, (D) preparation of 7-deaza-7-carbamido-$N^2$-isobutyryl-2'-deoxyguanosine, and (E) preparation of 7-deaza-7-aminomethyl-$N^2$-isobutyryl-2'-deoxyguanosine.

1. Preparation of 9-[3',5',$N^2$-tri(tert-butyl-dimethyl-silyl)-β-D-2'-deoxyribofuranosyl]-7-deaza-7-carbamido-6-chloropurine (FIG. 6A)

9-[3',5',$N^2$-tri (tert-butyl-dimethylsilyl)-deoxyribofuranosyl]-7-deaza-7-carbomethoxy-6-chloropurine (U.S. patent publication no. 2013/0035237) is treated with 7M ammonia solution in methanol for 24 hours at room temperature. The solution is evaporated and the crude solid is used in the next step without purification.

2. Preparation of 9-β-D-2'-deoxyribofuranosyl-7-deaza-7-carbamido-6-chloropurine (FIG. 6B)

9-[3',5',$N^2$-tri(tert-butyl-dimethylsilyl)-β-D-2'-deoxyribofuranosyl]-7-deaza-7-carbamido-6-chloropurine is treated with 1M TBAF in tetrahydrofuran for 24 hours. The mixture is evaporated and the crude nucleoside is purified by reverse phase HPLC. The structure of the compound is confirmed by NMR and Mass Spectrometry.

3. Preparation of 7-deaza-7-carbamido-2'-deoxyguanosine (FIG. 6C)

9-β-D-2'-deoxyribofuranosyl-7-deaza-7-carbamido-6-chloropurine is dissolved in water containing 5 molar equivalents of 1,4-diazabicyclo[2.2.2]octane (DABCO). The solution is refluxed overnight and the crude nucleoside is purified by reverse phase HPLC. The structure of compound is confirmed by NMR and Mass Spectrometry.

4. Preparation of 7-deaza-7-carbamido-$N^2$-isobutyryl-2'-deoxyguanosine (FIG. 6D)

7-deaza-7-carbamido-2'-deoxyguanosine is co-evaporated 3 times with anhydrous pyridine. The residue is dissolved in a mixture of pyridine and isobutyric acid anhydride (3:1) and the resulting mixture is stirred for 24 hours at room temperature. The flask is cooled in an ice-water bath and an equal volume of methanol is slowly added. After 4 hours the mixture is evaporated and the residue is dissolved in pyridine, cooled to 0° C. in an ice-water bath and an equal volume of 1M sodium hydroxide is added. After 20 minutes an excess of a pyridinium form of Dowex resin is added. The mixture is filtered and the Dowex resin washed with 50% aqueous pyridine. The solution is evaporated and the crude 7-deaza-7-carbamido-$N^2$-isobutyryl-2'-deoxyguanosine is used in the next step without purification.

5. Preparation of 7-deaza-7-aminomethyl-$N^2$-isobutyryl-2'-deoxyguanosine (FIG. 6E)

Crude 7-deaza-7-carbamido-$N^2$-isobutyryl-2'-deoxyguanosine is dissolved in methanol and placed in a thick wall glass vial. Powder of 10% palladium on carbon is added. The mixture is stirred for 24 hours at 40 psi of hydrogen pressure. The solution is filtered and 7-deaza-7-aminomethyl-$N^2$-isobutyryl-2'-deoxyguanosine is purified by reverse phase HPLC. The structure of the compound is confirmed by NMR and Mass Spectrometry.

Figure 7:
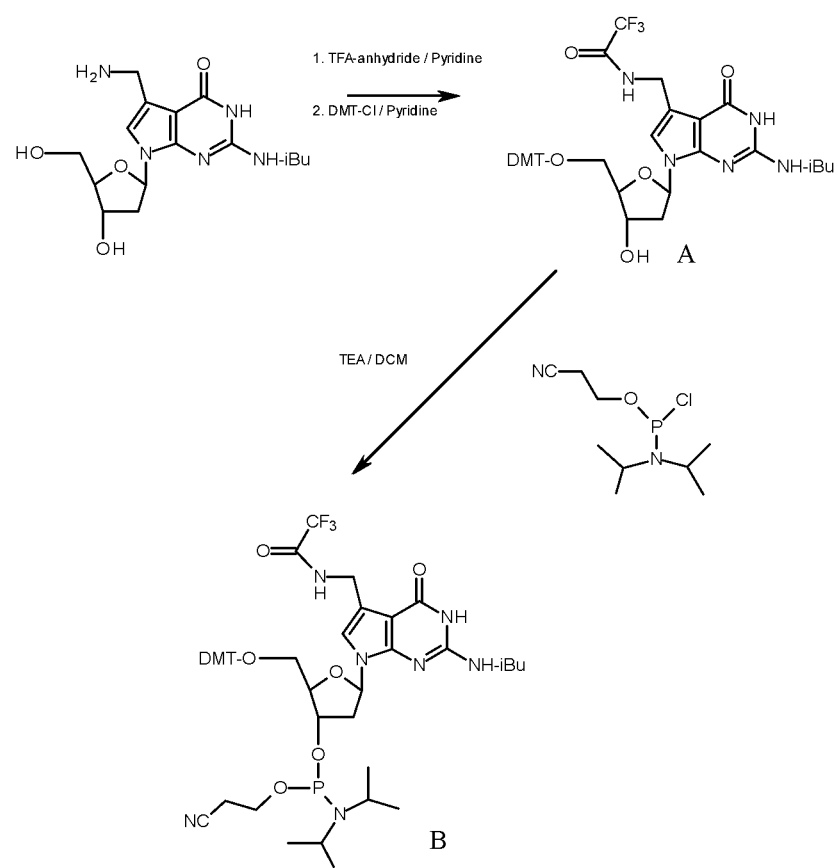
FIG. 7: Synthesis of 5'-Dimethoxytrityl-$N^2$-isobutyryl-7-deaza-7-(trifluoroacetamido)methyl-2'-deoxyguanosine 3'-phosphoramidite. (A) Preparation of 5'-Dimethoxytrityl-$N^2$-isobutyryl-7-deaza-7-(trifluoroacetamido)methyl-2' deoxyguanosine and (B) and preparation of 5'-Dimethoxytrityl-$N^2$-isobutyryl-7-deaza-7-(trifluoroacetamido)methyl-2'-deoxyguanosine 3'-phosphoramidite.

B. Synthesis of 5'-Dimethoxytrityl-$N^2$-isobutyryl-7-deaza-7-(trifluoroacetamido)methyl-2'-deoxyguanosine 3'-phosphoramidite 1. Preparation of 5'-Dimethoxytrityl-$N^2$-isobutyryl-7-deaza-7-(trifluoroacetamido)methyl-2'-deoxyguanosine (FIG. 7A)

7-deaza-7-aminomethyl-$N^2$-isobutyryl-2'-deoxyguanosine is dissolved in anhydrous pyridine and 10 molar equivalents of trifluoroacetic anhydride are added. Mixture is stirred for 1 hour at room temperature. The flask is cooled to 0° C. in an ice-water bath, an equal volume of methanol is added and after 30 minutes the mixture is evaporated under reduced pressure. The mixture is co-evaporated three additional times with methanol and twice with anhydrous pyridine. The resulting residue is dissolved in pyridine.

DMT-chloride (1.2 equivalents) is added and the mixture is stirred for 6 hours at room temperature. The mixture is evaporated under reduced pressure and the residue dissolved in DCM. 5'-Dimethoxytrityl-$N^2$-isobutyryl-7-deaza-7-(trifluoroacetamido)methyl-2'-deoxyguanosine is purified by silica gel chromatography using a stepwise gradient of methanol in DCM. Fractions containing pure product are combined, evaporated and dried at high vacuum. The structure of compound is confirmed by NMR and Mass Spectrometry.

2. Preparation of 5'-Dimethoxytrityl-$N^2$-isobutyryl-7-deaza-7-(trifluoroacetamido)methyl-2'-deoxyguanosine 3'-phosphoramidite (FIG. 7B)

Dimethoxytrityl-$N^2$-isobutyryl-7-deaza-7-(trifluoroacetamido)methyl-2'-deoxyguanosine is dissolved in DCM and 1 equivalent of triethylamine and 1.1 equivalent of 2-cyanoethyl N,N-diisopropylchlorophosphoramidite is added. After 2 hours the mixture is evaporated on a rotary evaporator and the residue is dissolved in ethyl acetate. Crude 5'-Dimethoxytrityl-$N^2$-isobutyryl-7-deaza-7-(trifluoroacetamido)methyl-2'-deoxyguanosine 3'-phosphoramidite is purified by silica gel chromatography in hexane-ethyl acetate containing 0.1% of pyridine. Fractions containing pure product are combined, evaporated and dried on high vacuum. The structure of compound is confirmed by NMR and Mass Spectrometry.

Figure 8:
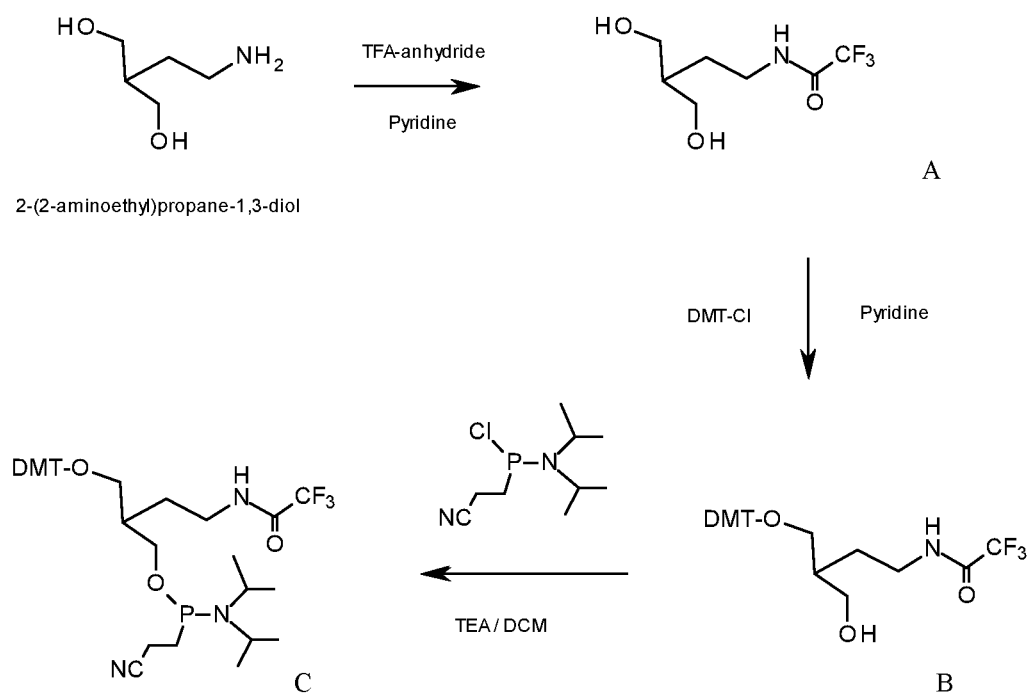
FIG. 8: Synthesis of 1-(4,4-dimethoxytrityl)-2-d2-trifluoroacetamido]ethyl-3-phosphoramidite. (A) Preparation of 2,2,2-trifluoro-N-[4-hydroxy-3-(hydroxymethyl)butyl]acetamide, (B) preparation of 2,2,2-trifluoro-N-[4-dimethoxytrityl-3-(hydroxymethyl)butyl]acetamide, and (C) preparation of 1-(4,4-dimethoxytrityl)-2-[2-trifluoroacetamido]ethyl-3-phosphoramidite.

C. Synthesis of 1-(4,4-dimethoxytrityl)-2-[2-trifluoroacetamido]ethyl-3-phosphoramidite 1. Preparation of 2,2,2-trifluoro-N-[4-hydroxy-3-(hydroxymethyl)butyl]acetamide (FIG. 8A)

2-(2-aminoethyl)propane-1,3-diol is treated with excess of trifluoroacetic acid anhydride in pyridine for 1 hour at room temperature. Equal volume of methanol is added and after 2 hours the mixture is evaporated at reduced pressure and co-evaporated twice with anhydrous pyridine. The residue is used in next step without purification.

2. Preparation of 2,2,2-trifluoro-N-[4-dimethoxytrityl-3-(hydroxymethyl)butyl]acetamide (FIG. 8B)

Crude 2,2,2-trifluoro-N-[4-hydroxy-3-(hydroxymethyl)butyl]acetamide is dissolved in pyridine and 1.1 molar equivalent of 4,4-dimethoxytrityl chloride is added to the solution. The mixture is stirred for 4 hours at room temperature. The solution is evaporated and the product is purified by silica gel chromatography in DCM-methanol containing 0.1% pyridine. Fractions containing pure product are combined, evaporated and dried at high vacuum. The structure of compound is confirmed by NMR and Mass Spectrometry.

3. Preparation of 1-(4,4-dimethoxytrityl)-2-[2-trifluoroacetamido]ethyl-3-phosphoramidite (FIG. 8C)

2,2,2-Trifluoro-N-[4-dimethoxytrityl-3-(hydroxymethyl)butyl]acetamide is dissolved in DCM and 1 equivalent of triethylamine and 1.1 equivalent of 2-cyanoethyl N,N-diisopropylchlorophosphoramidite is added. After 2 hours the mixture is evaporated and the residue is dissolved in ethyl acetate. Crude 1-(4,4-dimethoxytrityl)-2-[2-rifluoroacetamido]ethyl-3-phosphoramidite is purified by silica gel chromatography in hexane-ethyl acetate containing 0.1% of pyridine. Fractions containing pure product are combined, evaporated and dried on high vacuum. The structure of compound is confirmed by NMR and Mass Spectrometry.

Figure 9:
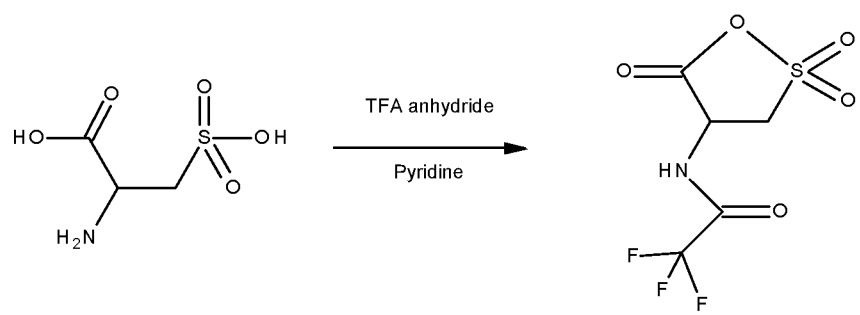
FIG. 9: Synthesis of 2,2,2-trifluoro-N-(2,2,5-trioxooxathiolan-4-yl)acetamide.

D. Synthesis of 2,2,2-trifluoro-N-(2,2,5-trioxooxathiolan-4-yl)acetamide (FIG. 9)

L-Cysteic acid (J. Mass Spectrometry, 2012, V. 47, pp. 529-538) is treated with large excess of trifluoroacetic anhydride in pyridine for several hours. The mixture is evaporated and co-evaporated twice with pyridine and twice with toluene. The crude product is used without purification E. Synthesis of Oligonucleotides with Internal Primary Amino Group for C to U Conversion Oligonucleotide containing 7-deaza-7-aminomethyl-2'-deoxyguanosine residue or 2-(2-aminoethyl)-1,3-propylene residue is prepared by standard automated oligonucleotide synthesis using nucleoside phosphoramidite building blocks. The 5'-dimethoxytrityl-$N^2$-isobutyryl-7-deaza-7-(trifluoroacetamido)methyl-2'-deoxyguanosine 3'-phosphoramidite or 1-(4,4-dimethoxytrityl)-2-[2-trifluoroacetamido]ethyl-3-phosphoramidite are used for incorporation at one or more specific locations in the oligonucleotide. The oligonucleotide is deprotected by treatment with concentrated ammonium hydroxide at 50° C. for 3 hours. Crude oligonucleotide is isolated and purified by combination of anion exchange and reverse phase HPLC. The structure and sequence is confirmed by Mass Spectrometry.

F. Conjugation of 2,2,2-trifluoro-N-(2,2,5-trioxooxathiolan-4-yl)acetamide to an Oligonucleotide with Primary Amino Group (FIG. 10)

The triethylammonium salt of the oligonucleotide containing a primary amino group is dissolved in dry DMF and a 10 molar excess of 2,2,2-trifluoro-N-(2,2,5-trioxooxathiolan-4-yl)acetamide is added. The mixture is stirred overnight at 50° C. The mixture is diluted with 5 volumes of 100 mM TEAB and purified by combination of anion exchange and reverse phase chromatography.

Example 4

Figure 11:
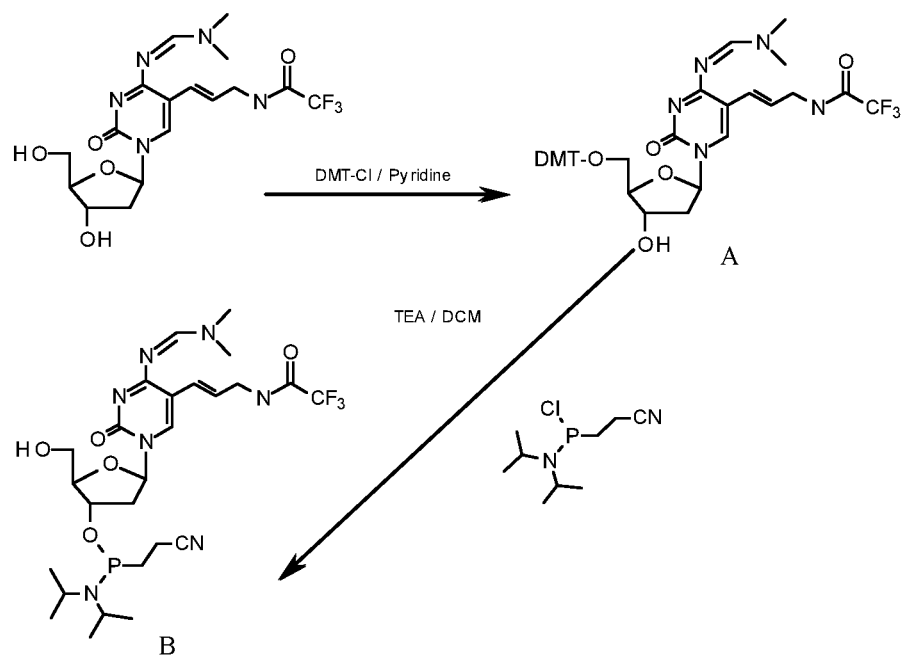
FIG. 11: Synthesis of oligonucleotides with 2-deoxycytidine-nitrosoalkyl conjugate for G to $O^6$-Me-G conversion. Preparation of 5'-Dimethoxytrityl-5-(E)-(3-trifluoroacetamidoallyl)-$N^4$-formamidine-2'-deoxycytidine (A) and preparation of 5'-Dimethoxytrityl-5-(E)-(3-trifluoroacetamidoallyl)-$N^4$-formamidine-2'-deoxycytidine 3'-phosphoramidite (B).

Synthesis of Oligonucleotides with 2-deoxycytidine-nitrosoalkyl Conjugate for G to $O^6$-Me-G Conversion A Mimic 1. Preparation of 5'-Dimethoxytrityl-5-(E)-(3-trifluoroacetamidoallyl)-$N^4$-formamidine-2'-deoxycytidine (FIG. 11A)

5-(E)-(3-trifluoroacetamidoallyl)-$N^4$-formamidine-2' deoxycytidine (Tetrahedron Letters, 2011, V. 52, pp. 181-183) is dissolved in anhydrous pyridine and DMT-chloride (1.2 equivalents) is added. The mixture is stirred for 6 hours at room temperature. The mixture is evaporated under reduced pressure and the residue is dissolved in DCM. The crude 5'-Dimethoxytrityl-5-(E)-(3-trifluoroacetamidoallyl)-$N^4$-formamidine-2'-deoxycytidine is purified by silica gel chromatography using stepwise gradient of methanol in DCM. Fractions containing pure product are combined, evaporated and dried at high vacuum. The structure of nucleoside is confirmed by NMR and Mass Spectrometry.

2. Preparation of 5'-Dimethoxytrityl-5-(E)-(3'-trifluoroacetamidoallyl)-$N^4$-formamidine-2-deoxyoytidine 3'-phosphoramidite (FIG. 11B)

5'-Dimethoxytrityl-5-(E)-(3-trifluoroacetamidoallyl)-$N^4$-formamidine-2'-deoxycytidine is dissolved in DCM and 1 equivalent of triethylamine and 1.1 equivalent of 2-cyanoethyl N,N-diisopropylchlorophosphoramidite are added. After 2 hours the mixture is evaporated on rotary evaporator and the residue is dissolved in ethyl acetate. The crude 5'-dimethoxytrityl-E-5-(2-carbethoxyvinyl)-$N^4$-benzoyl-2'-deoxycytidine 3'-phosphoramidite is purified by silica gel chromatography in hexane-ethyl acetate containing 0.1% of pyridine. Fractions containing pure product are combined, evaporated and dried at high vacuum. The structure of nucleoside is confirmed by NMR and Mass Spectrometry.

3. Synthesis of 4-[[methyl(nitroso)amino]methoxy]-4-oxo-butanoic acid

Hydroxymethylmethylnitrosamine (Kingston Chemistry Cat #KST-14259951) is dissolved in pyridine and 1.1 equivalent of succinic acid anhydride is added. The mixture is stirred for 4 hours. The crude product is precipitated with hexane and used in the next step.

Figure 12:
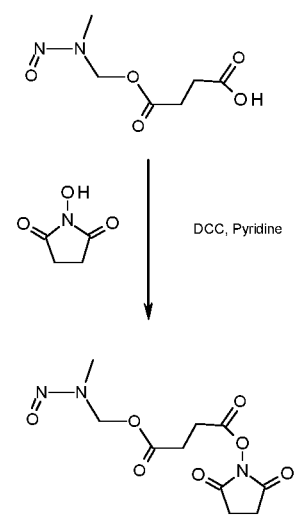
FIG. 12: Synthesis of N-hydroxysuccinimide ("NHS") ester of 4-{[methyl(nitroso)amino]methoxy}-4-oxo-butanoic acid.

4. Synthesis of NHS ester of 4-[[methyl(nitroso)amino]methoxy]-4-oxo-butanoic acid (FIG. 12)

4-[[methyl(nitroso)amino]methoxy]-4-oxo-butanoic acid is dissolved in pyridine and 1 equivalent of N-hydroxysuccinimide is added. To that mixture 3 equivalents of N,N'-dicyclohexylcarbodiamide is added. The mixture is stirred for 8 hours at room temperature. The mixture is filtered and crude product is precipitated with hexane and used in next step.

5. Synthesis of Oligonucleotides with Internal Primary Amino Group for G to $O^6$-MeG Conversion The oligonucleotide containing the 5-aminoallyl-2'-deoxycytidine residue or the 2-(2-aminoethyl)-1,3-propylene residue is prepared by standard automated oligonucleotide synthesis using nucleoside phosphoramidite building blocks. The 5'-dimethoxytrityl-5-(E)-(3-trifluoroacetamidoallyl)-$N^4$-formamidine-2'-deoxycytidine 3'-phosphoramidite or 1-(4,4-dimethoxytrityl)-2-[2-trifluoroacetamido]ethyl-3-phosphoramidite are used for incorporation at one or more specific locations in the oligonucleotide. The oligonucleotide is deprotected by treatment with concentrated ammonium hydroxide at 50° C. for 3 hours. Crude oligonucleotide is isolated and purified by combination of anion exchange and reverse phase HPLC. The structure and sequence is confirmed by Mass Spectrometry.

6. Conjugation of NHS ester of 4-{[methyl(nitroso) amino]methoxy}-4-oxo-butanoic acid to the Oligonucleotide with Primary Amino Group (FIG. 13)

The modified oligonucleotide containing a primary amino group is dissolved in a DMF-0.1M sodium bicarbonate (1:3) mixture and a 10 molar excess of NHS ester of 4-[[methyl(nitroso)amino]methoxy]-4-oxo-butanoic acid is added. Mixture is stirred for 2 hours at room temperature. The mixture is diluted with 5 volumes of 100 mM TEAB and oligonucleotide-4-[[methyl(nitroso)amino]methoxy]-4-oxo-butanoic acid conjugate is purified by combination of anion exchange and reverse phase chromatography. The oligonucleotide with the non-nucleoside unit can be used for G to $O^6$-MeG conversion Adenosine mimic) or for U to $O^4$-MeU conversion (Cytidine mimic).

Example 5

Synthesis of Editing Oligonucleotides with 2'-deoxyadenosine-nitroso-N-methyl Conjugate for U to $O^4$-Me-U Conversion (Cytidine Mimic)

A. Synthesis of 7-deaza-7-aminomethyl-N-benzoyl-5'-DMT-dA-phosphoramidite

Figure 14:
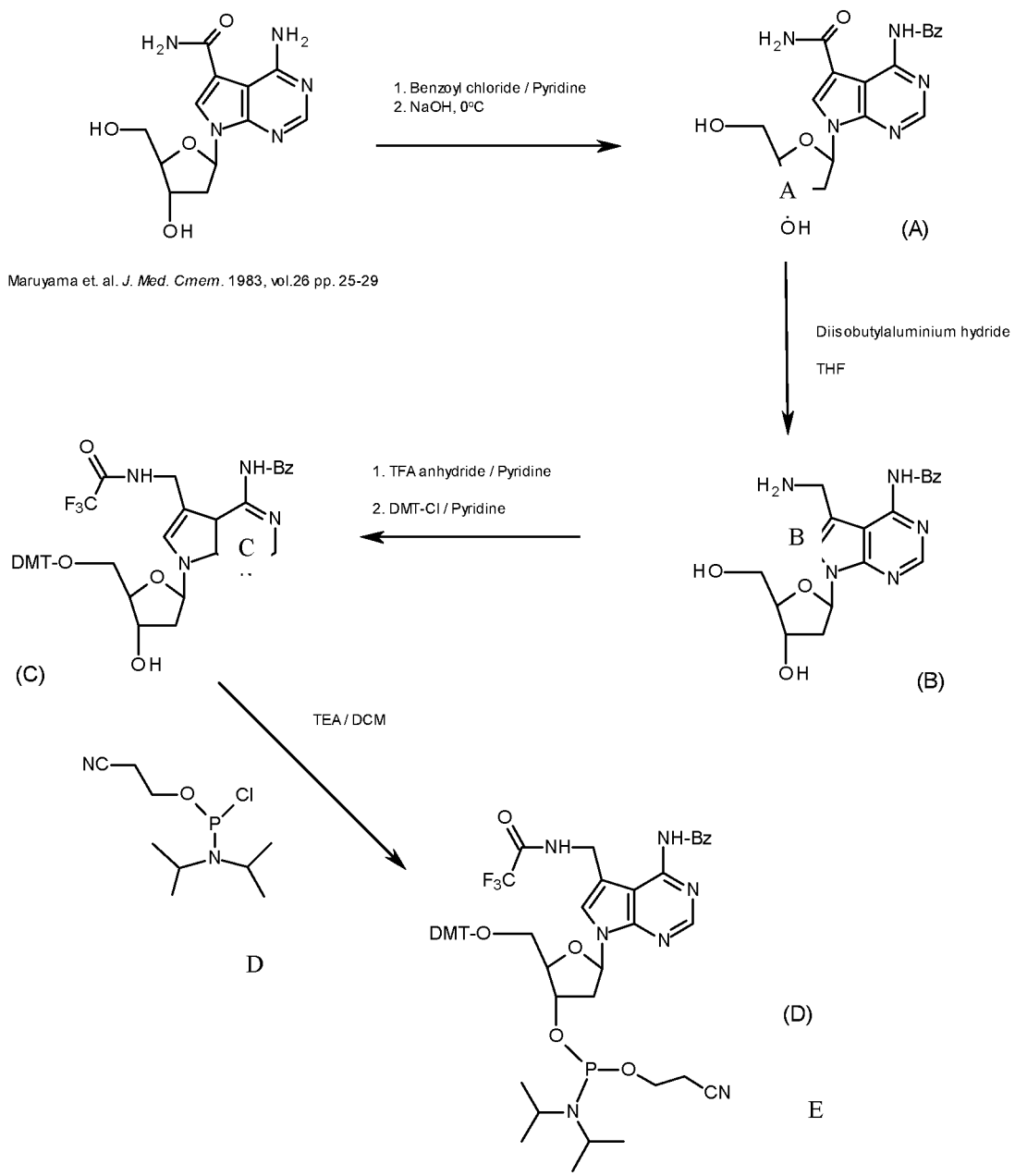
FIG. 14: Synthesis of editing oligonucleotides with 2'-deoxyadenosine-nitroso-N-methyl conjugate for U to $O^4$-Me-U conversion. (A) Preparation of 7-deaza-7-methoxycarbonyl-$N^6$-benzoyl-2'-deoxyadenosine, (B) preparation of 7-deaza-7-aminomethyl-$N^6$-benzoyl-2'-deoxyadenosine, (C) preparation of 5'-Dimethoxytrityl-$N^6$-benzoyl-7-deaza-7-(trifluoroacetamido)methyl-2'-deoxyadenosine, and (D) preparation of 5'-Dimethoxytrityl-$N^6$-benzoyl-7-deaza-7-(trifluoroacetamido)methyl-2'-deoxyadenosine 3'-phosphoramidite.

1. Preparation of 7-deaza-7-carboxamido-$N^6$-benzoyl-2'-deoxyadenosine (FIG. 14A)

2'-deoxysangivamycin (Maruyama et. al. *J. Med. Cmem.* 1983, vol. 26 pp. 25-29) is co-evaporated 3 times with anhydrous pyridine. The residue is then dissolved in mixture of pyridine and benzoyl chloride (9:1) and the resulting mixture is stirred for 24 hours at room temperature. The flask is cooled in an ice-water bath and an equal volume of methanol is added slowly. Once the methanol is added the mixture is allowed to stand for 1 hour. The solution is evaporated and the crude 7-deaza-7-carboxamido-$N^6$-benzoyl-2'-deoxyadenosine is purified by silica gel chromatography using a stepwise gradient of methanol in DCM or, alternatively, by reverse-phase HPLC in gradient of acetonitrile in 100 mM triethylammonium bicarbonate. Fractions containing pure product are combined, evaporated and dried at high vacuum. The structure of the nucleoside is confirmed by NMR and Mass Spectrometry.

2. Preparation of 7-deaza-7-aminomethyl-$N^6$-benzoyl-2-deoxyadenosine (FIG. 14B)

7-deaza-7-carboxamido-$N^6$-benzoyl-2'-deoxyadenosine is treated with a 1M solution of diisobutylaluminum hydride (3 molar equivalents) in THF at room temperature for 12 hours. The mixture is poured into a vigorously stirred solution of Rochelle's salt (1.2M aqueous potassium sodium tartrate). The solution is stirred vigorously for 2 hours and the mixture is extracted with DCM. The organic layer is dried with sodium sulfate and evaporated. Crude 7-deaza-7-aminomethyl-$N^6$-benzoyl-2'-deoxyadenosine is purified by reverse phase chromatography in a gradient of acetonitrile in 100 mM triethylammonium bicarbonate. Fractions containing pure 7-deaza-7-aminomethyl-$N^6$-benzoyl-2'-deoxyadenosine are combined, evaporated, co-evaporated with methanol and twice with anhydrous pyridine.

3. Preparation of 5'-Dimethoxytrityl-$N^6$-benzoyl-7-deaza-7-(trifluoroacetamido)methyl-2'-deoxyadenosine (FIG. 14C)

7-deaza-7-aminomethyl-$N^6$-benzoyl-2'-deoxyadenosine is dissolved in anhydrous pyridine and 10 molar equivalents of trifluoroacetic anhydride are added. Mixture is stirred for 1 hour at room temperature. The flask is cooled to 0° C. in an ice-water bath, an equal volume of methanol is added and after 30 minutes the mixture is evaporated under reduced pressure. The mixture is co-evaporated three times with methanol and twice with anhydrous pyridine. The residue is dissolved in pyridine.

DMT-chloride (1.2 equivalents) is added and the mixture is stirred for 6 hours at room temperature. The mixture is then evaporated under reduced pressure and the residue is dissolved in DCM. 5'-Dimethoxytrityl-$N^6$-benzoyl-7-deaza-7-(trifluoroacetamido)methyl-2'-deoxyadenosine is purified by silica gel chromatography using stepwise gradient of methanol in DCM. Fractions containing pure product are combined, evaporated and dried on high vacuum. The structure of the nucleoside is confirmed by NMR and Mass Spectrometry.

4. Preparation of 5'-Dimethoxytrityl-$N^6$-benzoyl-7-deaza-7-(trifluoroacetamido)methyl-2f-deoxyadenosine 3'-phosphoramidite (FIG. 14D)

5'-Dimethoxytrityl-$N^6$-benzoyl-7-deaza-7-(trifluoroacetamido)methyl-2'-deoxyadenosine is dissolved in DCM and 1 equivalent of triethylamine and 1.1 equivalent of 2-cyanoethyl N,N-diisopropylchlorophosphoramidite are added. After 2 hours the mixture is evaporated on a rotary evaporator and the residue is dissolved in ethyl acetate. Crude 5'-Dimethoxytrityl-$N^6$-benzoyl-7-deaza-7-(trifluoroacetamido)methyl-2'-deoxyadenosine 3'-phosphoramidite is purified by silica gel chromatography in hexane-ethyl acetate containing 0.1% of pyridine. Fractions containing pure product are combined, evaporated and dried at high vacuum. The structure of the nucleoside is confirmed by NMR and Mass Spectrometry.

B. Synthesis of Oligonucleotides with Internal Primary Amino Group for U to $O^4$-Me-U Conversion The oligonucleotide containing 7-deaza-7-aminomethyl-2'-deoxyadenosine residue or 2-(2-aminoethyl)-1,3-propylene residue is prepared by standard automated oligonucleotide synthesis using nucleoside phosphoramidite building blocks. The 5'-dimethoxytrityl-$N^6$-benzoyl-7-deaza-7-(trifluoroacetamido)methyl-2'-deoxyadenosine 3'-phosphoramidite or 1-(4,4-dimethoxytrityl)-2-[2-trifluoroacetamido]ethyl-3-phosphoramidite are used for incorporation at one or more specific locations in the oligonucleotide. The oligonucleotide is deprotected by treatment with concentrated ammonium hydroxide at 50° C. for 3 hours. The crude oligonucleotide is isolated and purified by combination of anion exchange and reverse phase HPLC. The structure and sequence is confirmed by Mass Spectrometry.

Figure 15:
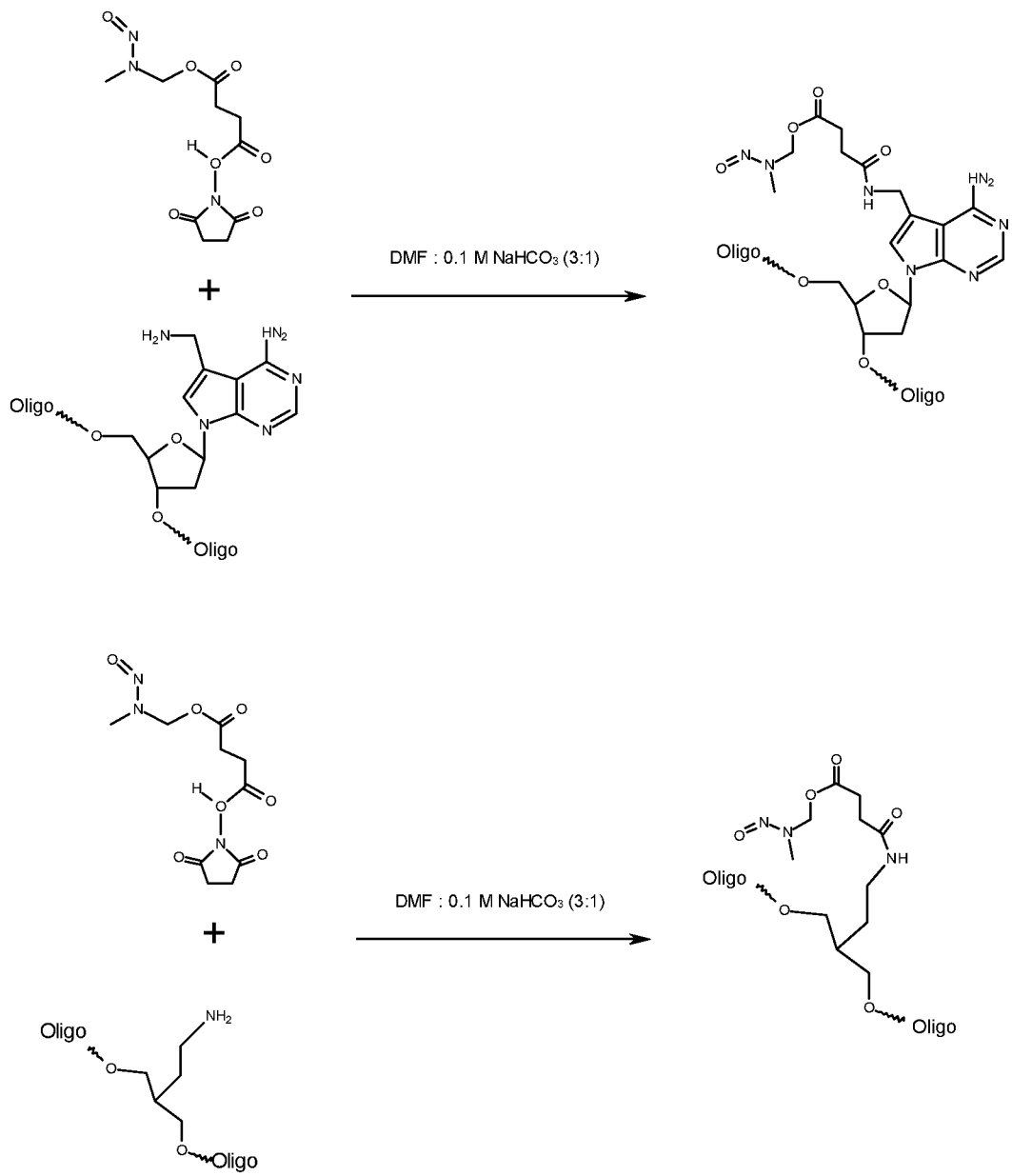
FIG. 15: Conjugation of NHS ester of 4-{[methyl(nitroso)amino]methoxy}-4-oxo-butanoic acid to modified oligonucleotides containing primary amino group.

C. Conjugation of NHS Ester of 4-[[methyl(nitroso)amino]methoxy]-4-oxo-butanoic acid to an Oligonucleotide with Primary Amino Group (FIG. 15)

The modified oligonucleotide containing primary amino group is dissolved in DMF-0.1M sodium bicarbonate (1:3) mixture and 10 molar excess of ester of 4-[[methyl(nitroso)amino]methoxy]-4-oxo-butanoic acid is added. The mixture is stirred for 2 hours at room temperature. The mixture is then diluted with 5 volumes of 100 mM triethylammonium bicarbonate and the oligonucleotide-4-[[methyl(nitroso)amino]methoxy]-4-oxo-butanoic acid conjugate is purified by combination of anion exchange and reverse phase chromatography.

Example 6

Figure 16:
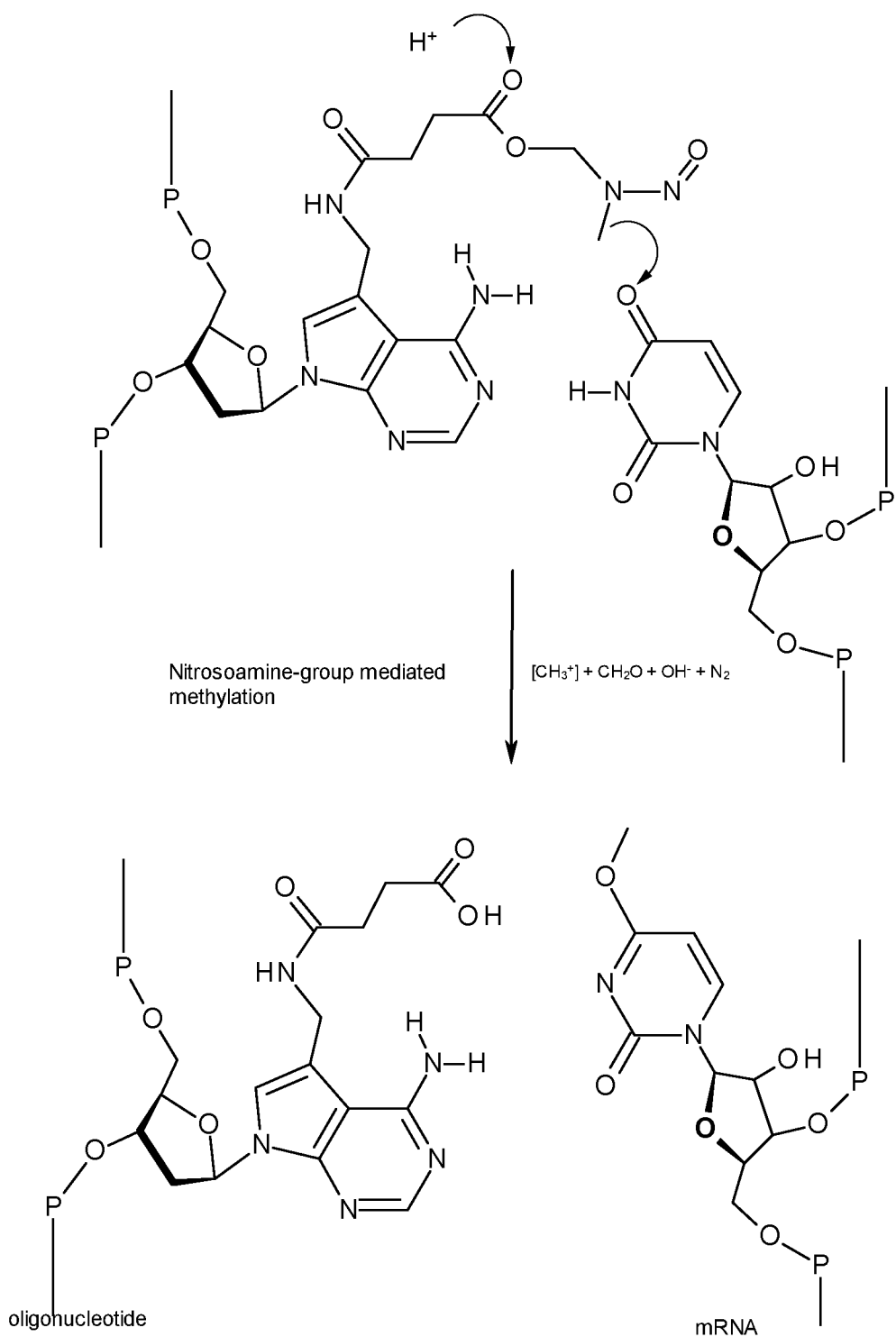
FIG. 16: Conversion of U to $O^4$-Me-U in mRNA using editing oligonucleotide containing nitrosoamine methylating group.

Scheme of U to $O^4$-Me-U Conversion in mRNA Using Editing Oligonucleotide Containing Nitrosoamine Methylating Group (FIG. 16)

An example of one schematic synthesis method is shown in FIG. 16.

Example 7

Figure 17:
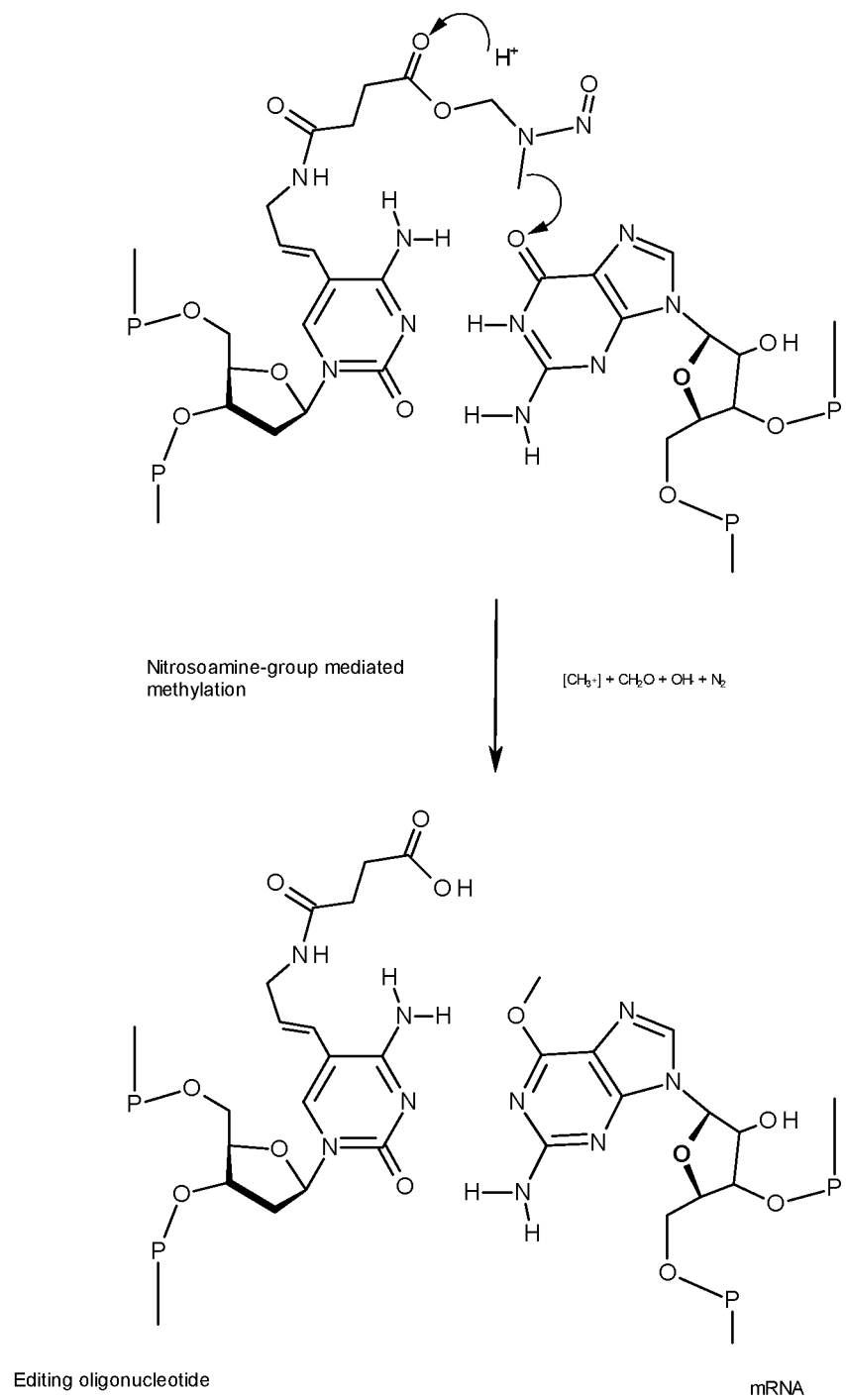
FIG. 17: Conversion of G to $O^6$-Me-G in mRNA using editing oligonucleotide containing nitrosoamine methylating group.

Scheme of G to $O^6$-Me-G Conversion in mRNA Using Editing Oligonucleotide Containing Nitrosoamine Methylating Group (FIG. 17)

An example of one schematic synthesis method is shown in FIG. 17.

Example 8

Figure 18:
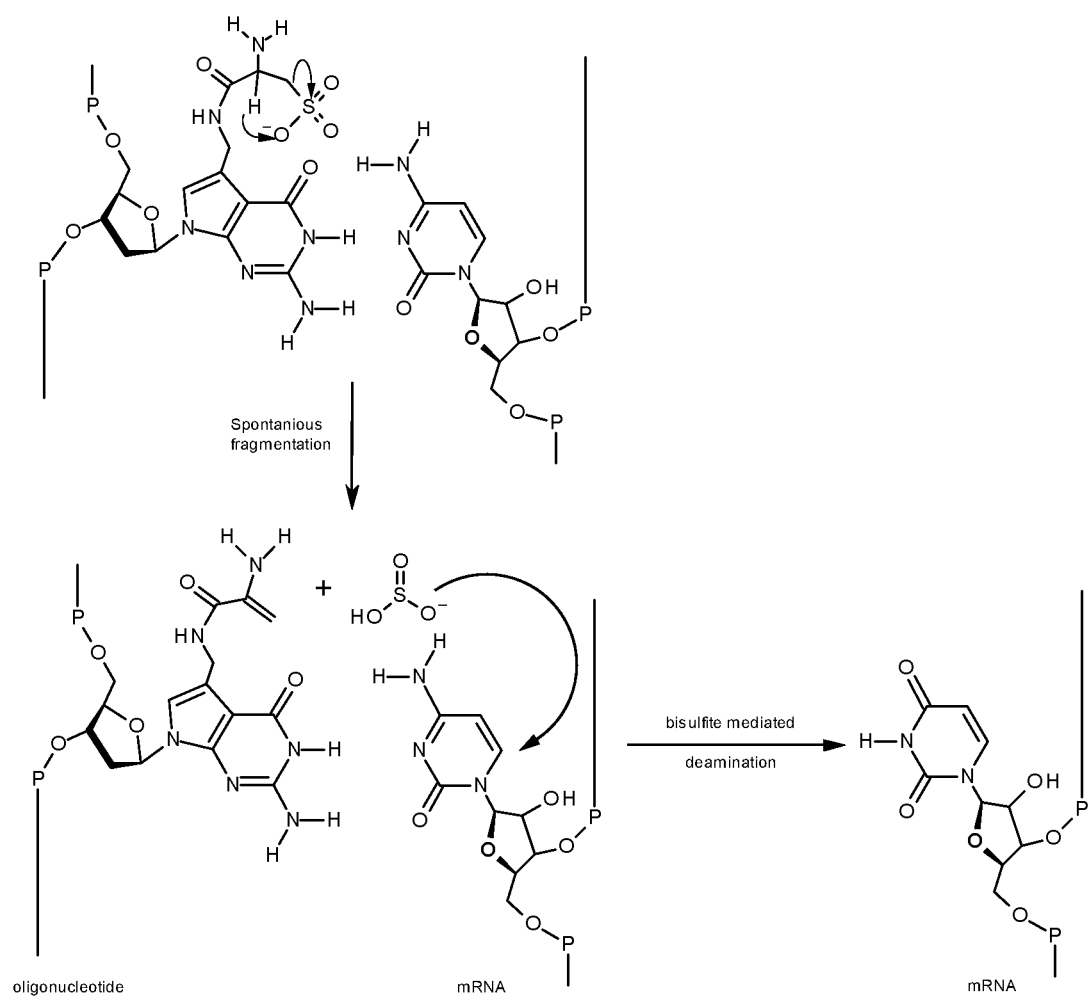
FIG. 18: Conversion of C to U in mRNA using editing oligonucleotide containing bisulfite generating group.

Scheme of C to U Conversion in mRNA Using Editing Oligonucleotide Containing Bisulfite Generating Group (FIG. 18)

An example of one schematic synthesis method is shown in FIG. 18.

Example 9

Process for Optimizing Length and Positioning of Editing Oligonucleotide

While positioning an editing oligonucleotide wherein the editing oligonucleotide is approximately centered (editing site in the middle) on the editing site typically results in some level of editing efficiency, it is not necessarily optimal. When targeting a mutation correction, or other target sequence change (e.g. creating a particular protective allele), the overall targeted site is determined by the location of the desired sequence change. In this case the optional optimization of the length and 5'-3' positioning of the editing oligonucleotides along the target site is somewhat constrained, and can be performed as follows. In the case of a DNA target, an editing oligonucleotide can be designed to target the sense or antisense strand of the targeted DNA. In the case of an RNA target, the editing oligonucleotide can only be designed complementary to the targeted RNA. Both in the case of targeting DNA or targeting RNA, optimization can begin with a parent editing oligonucleotide that is approximately centered on the targeted mutation. The editing oligonucleotide can have one of the chemical modification patterns described herein. Preferably, the initial editing oligonucleotide used for screening sites has a simple end-blocked modification pattern, that can simply be varied in the length and 5' and 3' positioning. In the case of editing oligonucleotides that function by chemical modification of a targeted nucleobase, the base modifying activity would have to remain positioned in the proximity of the targeted nucleobase.

In the case of targeting a gene for full or partial inactivation, the target site selection along the gene is much less constrained, and one or many target sites can be selected along the gene for use and screening. For example, most genes will be fully or partly inactivated by creating a pre-mature stop codon at one of a variety of sequences along the coding sequence. Editing oligonucleotides can be generated against one or more of these target sites, and tested in cells or organisms for relative editing efficiency and possibly specificity. A number of the editing oligonucleotides that have the most desirable properties based on this initial screen can be subjected to position and length optimization as described below.

With DNA targets, it is preferred to begin with an editing oligonucleotide having a length of about 40 to about 72 nucleotides. When targeting RNA, it is preferred to begin with 18-25 nucleotide editing oligonucleotide. The editing oligonucleotide can then be shifted in 1 to about 10 nucleotide increments to the 5' and to the 3' direction. Each resulting sequence can be tested for activity in cells or organisms to determine the editing efficiency and also potential editing specificity. Based on these results, the optimal position, or positions, can be determined. Beginning with an editing oligonucleotide sequence of the desired editing efficiency range from this first round of optimization, the editing oligonucleotide sequence can be modified in length by adding or removing bases complementary to the target on the 5' termini, 3' termini, or both the 5' and 3' termini in increments of 1 to about 20 nucleotides. Additional testing in cells or organisms for efficacy and potential specificity will yield a lead or multiple lead editing oligonucleotide sequences. Alternatively, the length can first be optimized beginning with the parent sequence, and then the resulting lead, or leads, can be further optimized by shifting the editing oligonucleotide to the 5' and/or 3' direction.

Once an optimized length, strand (antisense or sense) and 5'-3' positioning have been determined (or in the case where this process is not performed, the non-optimized oligonucleotide sequence can be used as a starting point), any editing oligonucleotide sequence with the desired efficacy can be varied with respect to the chemical modification pattern and tested in cells or organisms. When increasing or decreasing the length of a parent editing oligonucleotide during optimization, preferably the 5' editing segment, editing site and 3' editing segment will remain the same or substantially the same length and positioning relative to the editing site, while the 5' proximal segment and 3' proximal segment will increase or decrease in length. Alternatively, the 5' terminal segment, 5' proximal segment, 3' proximal segment and 3' terminal segment will remain the same or substantially the same length and position relative to the termini of the editing oligonucleotide, and the 5' editing segment and 3' editing segment will increase or decrease in length.

We claim:

1. A method of modifying a human genomic sequence within a human cell or a human individual comprising the steps of:
   introducing into said human cell or said human individual a single-stranded chemically modified oligonucleotide without additional exogenous proteins or nucleic acids to assist in editing said human genomic sequence, wherein said chemically modified oligonucleotide comprises one or more 2' sugar modification(s), one or more backbone modification(s), and one or more nucleobase modification(s), wherein the one or more 2' sugar modification(s) is selected from 2'-O-methyl, 2'-fluoro, or a combination of 2'-O-methyl and 2'-fluoro, wherein said oligonucleotide comprises, in 5' to 3' order, a 5' arm, an editing site, and a 3' arm, wherein said oligonucleotide is substantially complementary to a target sequence in said human genomic sequence with the exception of one or more mismatches in the editing site that modify the target sequence, wherein the chemically modified oligonucleotide is conjugated to GalNAc or a lipophilic group, wherein the human genomic sequence comprises a disease-causing mutation, and wherein:
   a) one of the 3' arm or the 5' arm does not comprise a 2'-sugar modification, and/or
   b) the chemically modified oligonucleotide comprises a methylphosphonate end-block.

2. The method of claim 1, wherein the 3' arm comprises one or more 2'-fluoro sugar modifications and the 5' arm does not comprise a 2'-sugar modification.

3. The method of claim 1, wherein the 5' arm comprises one or more 2'-O-methyl sugar modifications and the 3' arm does not comprise a 2'-sugar modification.

4. The method of claim 1, wherein the 5' arm comprises one or more 2'-O-methyl sugar modifications or one or more 2'-fluoro sugar modifications and the 3' arm comprises one or more 2'-fluoro sugar modifications.

5. The method of claim 1, wherein the one or more backbone modifications is selected from phosphorothioate, methyl phosphonate or a combination of phosphorothioate and methyl phosphonate.

6. The method of claim 5, wherein the chemically modified oligonucleotide comprises one or more phosphorothioates at a 5' terminus of the 5' arm and one or more phosphorothioates at a 3' terminus of the 3' arm.

7. The method of claim 5, wherein the chemically modified oligonucleotide comprises one or more methyl phosphonates at a 5' terminus of the 5' arm and one or more phosphorothioates at a 3' terminus of the 3' arm.

8. The method of claim 1, wherein the nucleobase modification is one or more 5'-methyl-cytosine.

9. The method of claim 1, wherein the chemically modified oligonucleotide is formulated into a pharmaceutically acceptable composition additionally comprising a pharmaceutically acceptable carrier.

10. The method of claim 1 wherein the modification to the human genomic sequence reverts a mutated nucleotide to a wild-type nucleotide.

11. The method of claim 1 wherein the modification to the human genomic sequence modifies a codon in a mutated-disease-causing protein to produce a non-wild-type protein that is a non-disease-causing protein.

12. The method of claim 1, wherein the modification to the human genomic sequence modifies a human CFTR mutant protein to suppress its disease-causing effects.

13. The method of claim 12, wherein the human CFTR mutant protein causes cystic fibrosis.

14. The method of claim 13, wherein cystic fibrosis caused by a delta 508 mutation.

15. The method of claim 1, wherein the chemically modified oligonucleotide further comprises a phosphorothiate modification at the 5' terminus.

16. The method of claim 15, wherein the chemically modified oligonucleotide comprises a phosphorothiate modification at the first three nucleotides of the 5' terminus.

17. The method of claim 1, wherein the chemically modified oligonucleotide comprises a methylphosphonate end-block.

18. The method of claim 1, wherein the 2'-O-methyl modifications are 5' of the editing site and the 2'-fluoro modifications are 3' of the editing site.

* * * * *